(12) United States Patent
Inoue

(10) Patent No.: US 11,866,472 B2
(45) Date of Patent: Jan. 9, 2024

(54) PEPTIDE FOR TREATING RETINITIS PIGMENTOSA

(71) Applicant: DAIICHI SANKYO COMPANY, LIMITED, Tokyo (JP)

(72) Inventor: Tatsuya Inoue, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 229 days.

(21) Appl. No.: 17/254,115

(22) PCT Filed: Jun. 21, 2019

(86) PCT No.: PCT/JP2019/024620
§ 371 (c)(1),
(2) Date: Dec. 18, 2020

(87) PCT Pub. No.: WO2019/245012
PCT Pub. Date: Dec. 26, 2019

(65) Prior Publication Data
US 2021/0347836 A1    Nov. 11, 2021

(30) Foreign Application Priority Data
Jun. 21, 2018 (JP) ................................. 2018-117875

(51) Int. Cl.
| | | |
|---|---|---|
| *C07K 14/47* | (2006.01) | |
| *A61K 47/62* | (2017.01) | |
| *A61P 27/02* | (2006.01) | |
| *A61K 45/06* | (2006.01) | |
| *C12Q 1/37* | (2006.01) | |
| *A61K 38/00* | (2006.01) | |

(52) U.S. Cl.
CPC .......... *C07K 14/4703* (2013.01); *A61K 45/06* (2013.01); *A61K 47/62* (2017.08); *A61P 27/02* (2018.01); *C12Q 1/37* (2013.01); *A61K 38/00* (2013.01)

(58) Field of Classification Search
CPC ............ C07K 14/4703; C07K 14/8135; A61K 45/06; A61K 47/62; A61K 38/00; A61K 38/57; A61K 35/12; A61K 31/7088; A61K 38/16; A61K 48/005; A61P 27/02; A61P 43/00; C12Q 1/37; C12N 9/6421
See application file for complete search history.

(56) References Cited

U.S. PATENT DOCUMENTS

| | | | |
|---|---|---|---|
| 9,738,727 B2 | 8/2017 | Wu et al. | |
| 2014/0323413 A1 | 10/2014 | Hageman et al. | |
| 2015/0197546 A1 | 7/2015 | Nishimiya et al. | |
| 2017/0260228 A1* | 9/2017 | Kasuya | A61K 9/204 |
| 2020/0377573 A1* | 12/2020 | Nishimiya | A61P 43/00 |

FOREIGN PATENT DOCUMENTS

| | | |
|---|---|---|
| CN | 103917556 A | 7/2014 |
| JP | 2014515012 A | 6/2014 |
| WO | 2014/024914 A1 | 2/2014 |
| WO | 2017/121766 A1 | 7/2017 |
| WO | 2018/117244 A1 | 6/2018 |

OTHER PUBLICATIONS

International Search Report dated Aug. 27, 2019, issued in corresponding Application No. PCT/JP2019/024620, filed Jun. 21, 2019, 2 pages.
Chinese First Office Action and Search Report dated Aug. 19, 2023, in corresponding Chinese Application No. 2019800418352, filed Jun. 21, 2019, 12 pages.

* cited by examiner

*Primary Examiner* — Marcela M Cordero Garcia
(74) *Attorney, Agent, or Firm* — Christensen O'Connor Johnson Kindness PLLC

(57) ABSTRACT

To provide a novel pharmaceutical use of a peptide. A pharmaceutical composition for the treatment or prevention of retinitis pigmentosa, comprising a peptide which comprises the amino acid sequence shown in SEQ ID NO: 30 and inhibits the protease activity.

45 Claims, 49 Drawing Sheets
Specification includes a Sequence Listing.

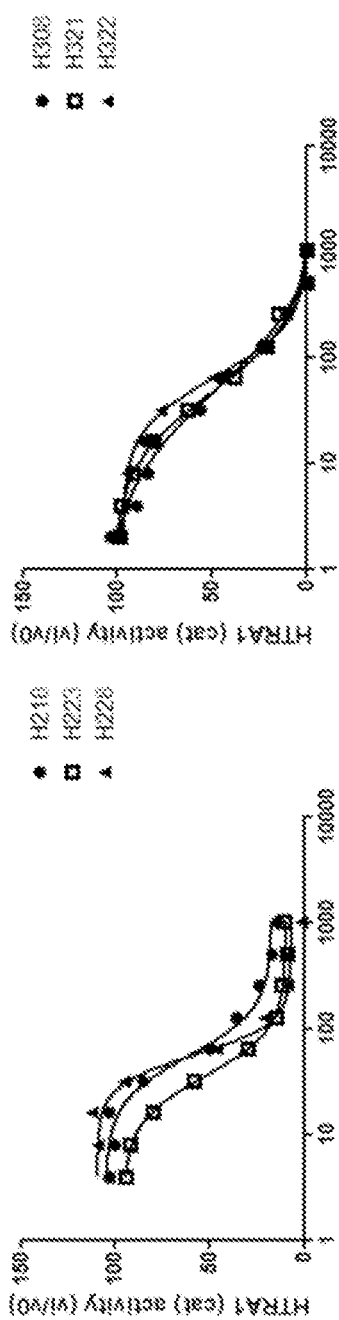
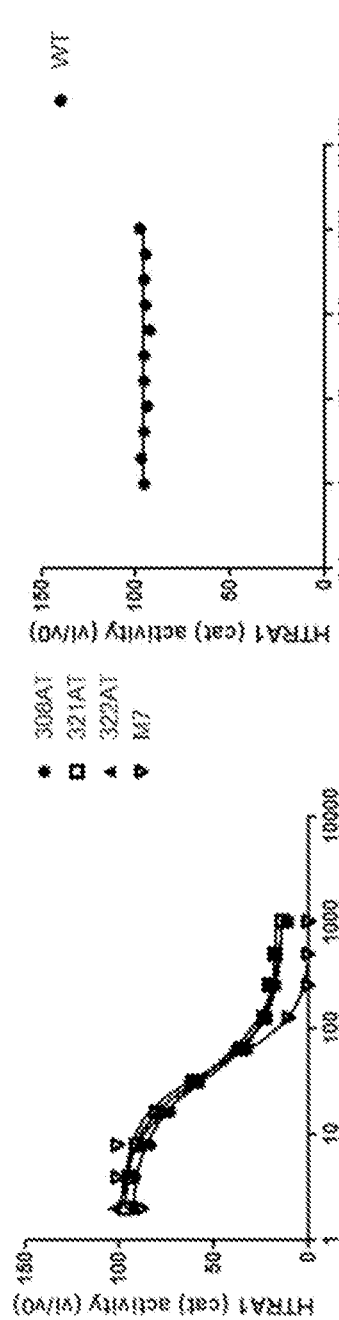
Figure 2A
Figure 2B
Figure 2C
Figure 2D

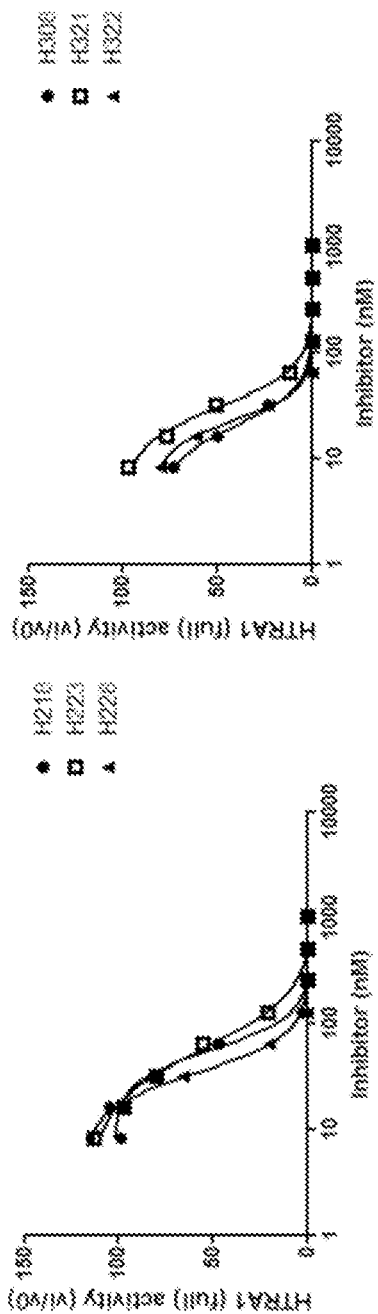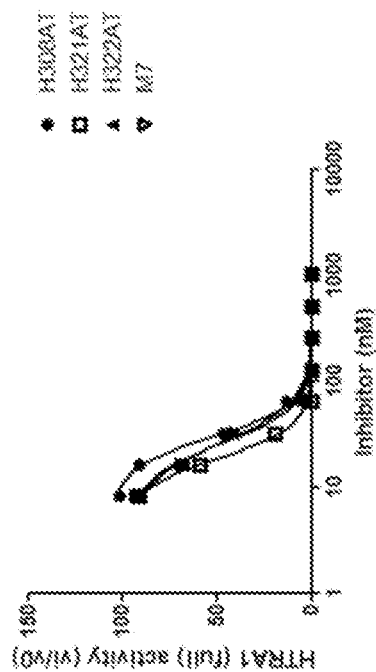
Figure 3A
Figure 3B
Figure 3C

[Figure 8]

H2-Opt

Mca-IRRVSYSFK(Dnp)K (SEQ ID NO: 54)

[Figure 13]

HUMAN SPINK2

DPQFGLFSKYRTPNCSQYRLPGCPRHFNPVCGSDMSTYANECTLCMKIREGGHNIKI
IRNGPC (SEQ ID NO: 1)

[Figure 14]

HUMAN SPINK2

GATCCGCAGTTTGGTCTGTTTAGCAAATATCGTACCCCGAATTGTAGCCAGTATCGT
CTGCCTGGTTGTCCGCGTCATTTTAATCCGGTTTGTGGTAGCGATATGAGCACCTAT
GCAAATGAATGTACCCTGTGCATGAAAATTCGTGAAGGTGGCCATAATATTAAAATT
ATTCGCAATGGTCCGTGCTAA (SEQ ID NO: 2)

[Figure 15]

HTRA1-INHIBITING PEPTIDE H218

DPQFGLFSKYRTPNCLKSEGMACYAYYEPVCGSDMSTYANECTLCMKIREGGHNIKI
IRNGPCGG (SEQ ID NO: 3)

[Figure 16]

HTRA1-INHIBITING PEPTIDE H218

GATCCGCAGTTTGGTCTGTTTAGCAAATATCGTACCCCGAATTGTCTGAAATCTGAA

GGTATGGCTTGTTACGCTTACTACGAACCGGTTTGTGGTAGCGATATGAGCACCTAT

GCAAATGAATGTACCCTGTGCATGAAAATTCGTGAAGGTGGCCATAATATTAAAATT

ATTCGCAATGGTCCGTGCGGCGGCTAA (SEQ ID NO: 4)

[Figure 17]

HTRA1-INHIBITING PEPTIDE H223

DPQFGLFSKYRTPNCTMDMGMACWAFYEPVCGSDMSTYANECTLCMKIREGGHNIKI

IRNGPCGG (SEQ ID NO: 5)

[Figure 18]

HTRA1-INHIBITING PEPTIDE H223

GATCCGCAGTTTGGTCTGTTTAGCAAATATCGTACCCCGAATTGTACTATGGACATG

GGTATGGCTTGTTGGGCTTTCTACGAACCGGTTTGTGGTAGCGATATGAGCACCTAT

GCAAATGAATGTACCCTGTGCATGAAAATTCGTGAAGGTGGCCATAATATTAAAATT

ATTCGCAATGGTCCGTGCGGCGGCTAA (SEQ ID NO: 6)

[Figure 19]

HTRA1-INHIBITING PEPTIDE H228

DPQFGLFSKYRTPNCGHYNGWACQAFFEPVCGSDMSTYANECTLCMKIREGGHNIKI

IRNGPCGG (SEQ ID NO: 7)

[Figure 20]

HTRA1-INHIBITING PEPTIDE H228

GATCCGCAGTTTGGTCTGTTTAGCAAATATCGTACCCCGAATTGTGGTCATTACAAC

GGTTGGGCTTGTCAGGCTTTCTTCGAACCGGTTTGTGGTAGCGATATGAGCACCTAT

GCAAATGAATGTACCCTGTGCATGAAAATTCGTGAAGGTGGCCATAATATTAAAATT

ATTCGCAATGGTCCGTGCGGCGGCTAA (SEQ ID NO: 8)

[Figure 21]

HTRA1-INHIBITING PEPTIDE H308

DPQFGLFSKYRTPNCSDHAGMACVALYEPVCGSDMSTYENECVLCMKIREGGHNIKI

IRNGPCGG (SEQ ID NO: 9)

[Figure 22]

HTRA1-INHIBITING PEPTIDE H308

GATCCGCAGTTTGGTCTGTTTAGCAAATATCGTACCCCGAATTGTAGCGACCATGCT

GGTATGGCATGTGTTGCTCTGTATGAACCGGTTTGTGGTAGCGATATGAGCACCTAT

GAAAATGAATGTGTTCTGTGCATGAAAATTCGTGAAGGTGGCCATAATATTAAAATT

ATTCGCAATGGTCCGTGCGGCGGCTAA (SEQ ID NO: 10)

[Figure 23]

HTRA1-INHIBITING PEPTIDE H321

DPQFGLFSKYRTPNCSDFDGMACYAFYEPVCGSDMSTYMNECALCMKIREGGHNIKI

IRNGPCGG (SEQ ID NO: 11)

[Figure 24]

HTRA1-INHIBITING PEPTIDE H321

GATCCGCAGTTTGGTCTGTTTAGCAAATATCGTACCCCGAATTGTAGCGACTTCGAC
GGTATGGCATGTTACGCTTTCTATGAACCGGTTTGTGGTAGCGATATGAGCACCTAT
ATGAATGAATGTGCTCTGTGCATGAAAATTCGTGAAGGTGGCCATAATATTAAAATT
ATTCGCAATGGTCCGTGCGGCGGCTAA (SEQ ID NO: 12)

[Figure 25]

HTRA1-INHIBITING PEPTIDE H322

DPQFGLFSKYRTPNCSQHEGMACYALYEPVCGSDMSTYVNECALCMKIREGGHNIKI
IRNGPCGG (SEQ ID NO: 13)

[Figure 26]

HTRA1-INHIBITING PEPTIDE H322

GATCCGCAGTTTGGTCTGTTTAGCAAATATCGTACCCCGAATTGTAGCCAGCATGAA
GGTATGGCATGTTACGCTCTGTATGAACCGGTTTGTGGTAGCGATATGAGCACCTAT
GTTAATGAATGTGCTCTGTGCATGAAAATTCGTGAAGGTGGCCATAATATTAAAATT
ATTCGCAATGGTCCGTGCGGCGGCTAA (SEQ ID NO: 14)

[Figure 27]

HTRA1-INHIBITING PEPTIDE H308AT

DPQFGLFSKYRTPNCSDHAGMACVALYEPVCGSDMSTYANECTLCMKIREGGHNIKI
IRNGPCGG (SEQ ID NO: 15)

[Figure 28]

HTRA1-INHIBITING PEPTIDE H308AT

GATCCGCAGTTTGGTCTGTTTAGCAAATATCGTACCCCGAATTGTAGCGACCATGCT
GGTATGGCATGTGTTGCTCTGTATGAACCGGTTTGTGGTAGCGATATGAGCACCTAT
GCAAATGAATGTACCCTGTGCATGAAAATTCGTGAAGGTGGCCATAATATTAAAATT
ATTCGCAATGGTCCGTGCGGCGGCTAA (SEQ ID NO: 16)

[Figure 29]

HTRA1-INHIBITING PEPTIDE H321AT

DPQFGLFSKYRTPNCSDFDGMACYAFYEPVCGSDMSTYANECTLCMKIREGGHNIKI
IRNGPCGG (SEQ ID NO: 17)

[Figure 30]

HTRA1-INHIBITING PEPTIDE H321AT

GATCCGCAGTTTGGTCTGTTTAGCAAATATCGTACCCCGAATTGTAGCGACTTCGAC
GGTATGGCATGTTACGCTTTCTATGAACCGGTTTGTGGTAGCGATATGAGCACCTAT
GCAAATGAATGTACCCTGTGCATGAAAATTCGTGAAGGTGGCCATAATATTAAAATT
ATTCGCAATGGTCCGTGCGGCGGCTAA (SEQ ID NO: 18)

[Figure 31]

HTRA1-INHIBITING PEPTIDE H322AT

DPQFGLFSKYRTPNCSQHEGMACYALYEPVCGSDMSTYANECTLCMKIREGGHNIKI
IRNGPCGG (SEQ ID NO: 19)

[Figure 32]

HTRA1-INHIBITING PEPTIDE H322AT

GATCCGCAGTTTGGTCTGTTTAGCAAATATCGTACCCCGAATTGTAGCCAGCATGAA
GGTATGGCATGTTACGCTCTGTATGAACCGGTTTGTGGTAGCGATATGAGCACCTAT
GCAAATGAATGTACCCTGTGCATGAAAATTCGTGAAGGTGGCCATAATATTAAAATT
ATTCGCAATGGTCCGTGCGGCGGCTAA (SEQ ID NO: 20)

[Figure 33]

HTRA1-INHIBITING PEPTIDE M7

DPQFGLFSKYRTPNCSDHAGMACVAFYEPVCGSDMSTYANECTLCMKIREGGHNIKI
IRNGPCGG (SEQ ID NO: 21)

[Figure 34]

HTRA1-INHIBITING PEPTIDE M7

GATCCGCAGTTTGGTCTGTTTAGCAAATATCGTACCCCGAATTGTAGCGACCATGCT
GGTATGGCATGTGTTGCTTTTTATGAACCGGTTTGTGGTAGCGATATGAGCACCTAT
GCAAATGAATGTACCCTGTGCATGAAAATTCGTGAAGGTGGCCATAATATTAAAATT
ATTCGCAATGGTCCGTGCGGCGGCTAA (SEQ ID NO: 22)

[Figure 35]

HTRA1-INHIBITING PEPTIDE H308_S16A

DPQFGLFSKYRTPNCADHAGMACVALYEPVCGSDMSTYENECVLCMKIREGGHNIKI
IRNGPCGG (SEQ ID NO: 23)

[Figure 36]

HTRA1-INHIBITING PEPTIDE H308_D1G_S16A

GPQFGLFSKYRTPNCADHAGMACVALYEPVCGSDMSTYENECVLCMKIREGGHNIKI
IRNGPCGG (SEQ ID NO: 24)

[Figure 37]

HTRA1-INHIBITING PEPTIDE H308_D1S_S16A

SPQFGLFSKYRTPNCADHAGMACVALYEPVCGSDMSTYENECVLCMKIREGGHNIKI
IRNGPCGG (SEQ ID NO: 25)

[Figure 38]

HTRA1-INHIBITING PEPTIDE H308_D1E_S16A

EPQFGLFSKYRTPNCADHAGMACVALYEPVCGSDMSTYENECVLCMKIREGGHNIKI
IRNGPCGG (SEQ ID NO: 26)

[Figure 39]

HTRA1-INHIBITING PEPTIDE H308_D1SLI_S16A

SLIPQFGLFSKYRTPNCADHAGMACVALYEPVCGSDMSTYENECVLCMKIREGGHNI
KIIRNGPCGG (SEQ ID NO: 27)

GPQFGLFSKYRTPNCADFDGMACYAFYEPVCGSDMSTYANECTLCMKIREGGHNIKI

IRNGPCGG (SEQ ID NO: 28)

GPQFGLFSKYRTPNCAQHEGMACYALYEPVCGSDMSTYANECTLCMKIREGGHNIKI

IRNGPCGG (SEQ ID NO: 29)

[Figure 42]

FORMULA FOR HTRA1-INHIBITING PEPTIDE $X_1$PQFGLFSKYRTPNC$X_2$$X_3$$X_4$$X_5$G$X_6$AC$X_7$A$X_8$$X_9$EPVCGSDMSTY$X_{10}$NEC$X_{11}$LCMKI

REGGHNIKIIRNGPC (SEQ ID NO: 30)

[Figure 43]

Stag + LINKER

GSGMKETAAAKFERQHMDSPDLGTDDDDKAMADIGSANS (SEQ ID NO: 31)

[Figure 44]

C-TERMINAL HEXAMER

GASAAA (SEQ ID NO: 32)

[Figure 45]

PRIMER 1

AAAAGAATTCTGATCCGCAGTTTGGTCTGTTTAG (SEQ ID NO: 33)

[Figure 46]

PRIMER 2

AAAACTCGAGTTATGCGGCCGCAGACGCGCCGCACGGACC (SEQ ID NO: 34)

[Figure 47]

PRIMER 3

AAAAGGATCCCTGGACAAACGTGATCCGCAGTTTGGTCTGTTTAG (SEQ ID NO: 35)

[Figure 48]

PRIMER 4

AAAACTCGAGTTAGCCGCCGCACGGACCATTGCGAATAATTTTA (SEQ ID NO: 36)

[Figure 49]

PRIMER 5

AAACATATGGGGCAGGAAGATCCCAACAGTTTGC (SEQ ID NO: 37)

[Figure 50]

PRIMER 6

AAACTCGAGTTTGGCCTGTCGGTCATGGGACTC (SEQ ID NO: 38)

[Figure 51]

PRIMER 7

AAAAGAATTCGCCACCATGCAGATTCCTAGAGCCG (SEQ ID NO: 39)

[Figure 52]

PRIMER 8

AAAACTCGAGTCAGTGGTGATGGTGGTGGTGGCCGG (SEQ ID NO: 40)

[Figure 53]

PRIMER 9

CTTGTCGTCATCGTCCTTGTAGTCGCCGGGGTCGATTTCCTC (SEQ ID NO: 41)

[Figure 54]

PRIMER 10

GCGACTACAAGGACGATGACGACAAGCACCACCACCATCATCAC (SEQ ID NO: 42)

[Figure 55]

PRIMER 11

AAAAACTCGAGCTAGTGATGATGGTGGTGGTGCTTGTCGTC (SEQ ID NO: 43)

[Figure 56]

PRIMER 12

CCGCAGTTTGGTCTGTTTAGCAAATATCGTACCCCGAATTGT (SEQ ID NO: 44)

[Figure 57]

PRIMER 13

GCCATACCAGCATGGTCCGCACAATTCGGGGTACGATATTTGC (SEQ ID NO: 45)

[Figure 58]

PRIMER 14

GCGGACCATGCTGGTATGGCATGTGTTGCTCTGTATGAAC (SEQ ID NO: 46)

[Figure 59]

PRIMER 15

AAAACTCGAGTTAGCCGCCGCACGGACCATTGCGAATAA (SEQ ID NO: 47)

[Figure 60]

PRIMER 16

AAAAGGATCCCTGGACAAACGTGATCCGCAGTTTGGTCTGTTTAG (SEQ ID NO: 48)

[Figure 61]

PRIMER 17

AAAAGGATCCCTGGACAAACGTGGCCCGCAGTTTGGTCTGTTTAG (SEQ ID NO: 49)

[Figure 62]

PRIMER 18

AAAAGGATCCCTGGACAAACGTAGCCCGCAGTTTGGTCTGTTTAG (SEQ ID NO: 50)

[Figure 63]

PRIMER 19

AAAAGGATCCCTGGACAAACGTGAACCGCAGTTTGGTCTGTTTAG (SEQ ID NO: 51)

[Figure 64]

PRIMER 20

AAAAGGATCCCTGGACAAACGTAGCCTGATTCCGCAGTTTGGTCTGTTTAG (SEQ ID NO: 52)

[Figure 65]

HUMAN HTRA1(full)

QLSRAGRSAPLAAGCPDRCEPARCPPQPEHCEGGRARDACGCCEVCGAPEGAACGLQ
EGPCGEGLQCVVPFGVPASATVRRRAQAGLCVCASSEPVCGSDANTYANLCQLRAAS
RRSERLHRPPVIVLQRGACGQGQEDPNSLRHKYNFIADVVEKIAPAVVHIELFRKLP
FSKREVPVASGSGFIVSEDGLIVTNAHVVTNKHRVKVELKNGATYEAKIKDVDEKAD
IALIKIDHQGKLPVLLLGRSSELRPGEFVVAIGSPFSLQNTVTTGIVSTTQRGGKEL
GLRNSDMDYIQTDAIINYGNSGGPLVNLDGEVIGINTLKVTAGISFAIPSDKIKKFL
TESHDRQAKGKAITKKKYIGIRMMSLTSSKAKELKDRHRDFPDVISGAYIIEVIPDT
PAEAGGLKENDVIISINGQSVVSANDVSDVIKRESTLNMVVRRGNEDIMITVIPEEI
DP (SEQ ID NO: 53)

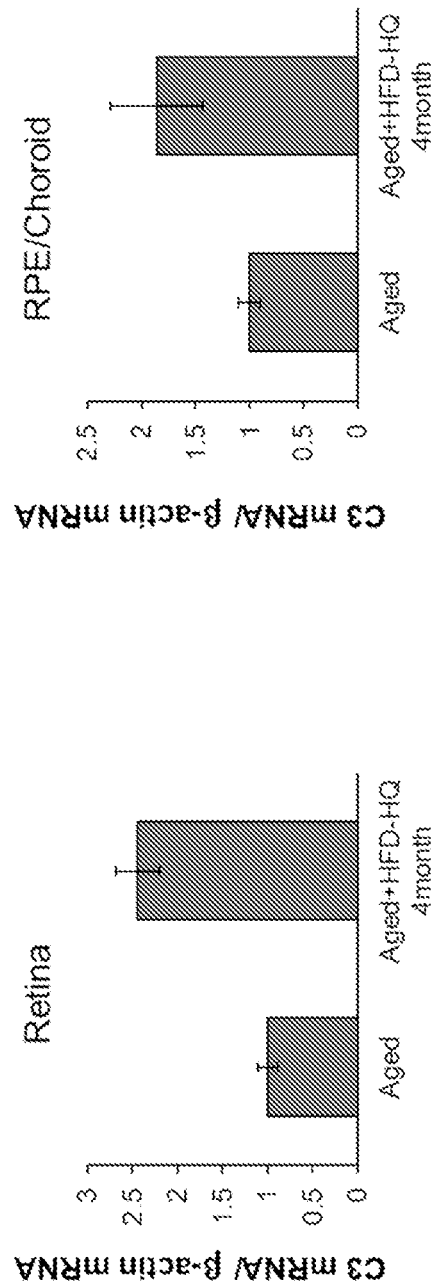
Figure 71C
Figure 71D
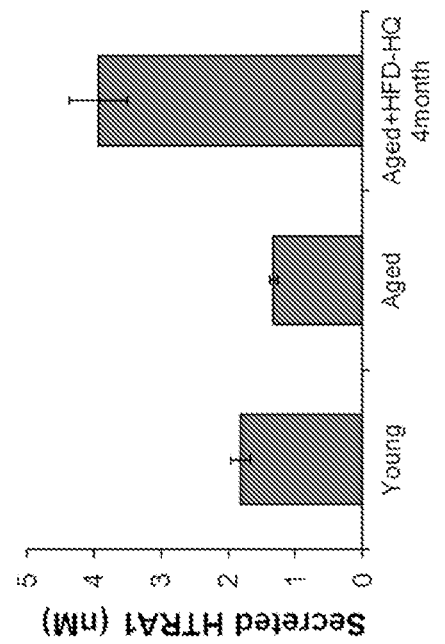
Figure 71E

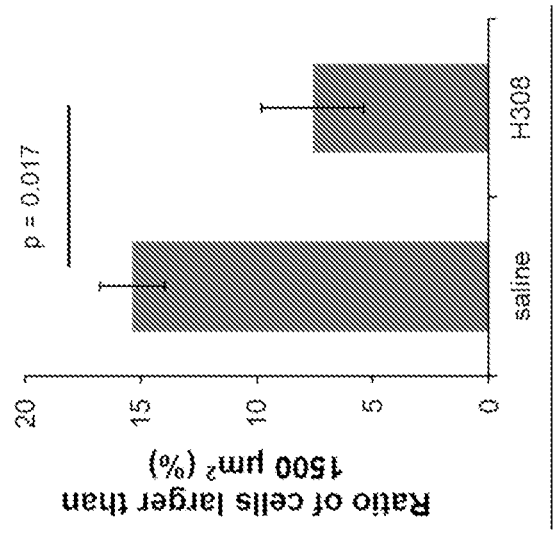
Figure 72B
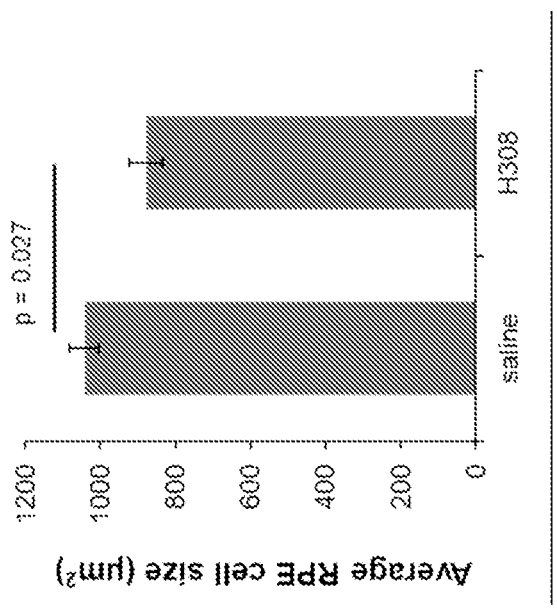
Figurre 72A

```
human   1  GSGFIVSEDGLIVTNAHVVTNK RVKVELKNGATYEAKIKDVDEKADIALIKIDHQGKLP  60
cyno.   1  GSGFIVSEDGLIVTNAHVVTNK RVKVELKNGATYEAKIKDVDEKADIALIKIDHQGKLP  60
rabbit  1  GSGFIVSEDGLIVTNAHVVTNK RVKVELKNGATYEAKIKDVDEKADIALIKIDHQGKLP  60
mouse   1  GSGFIVSEDGLIVTNAHVVTNK RVKVELKNGATYEAKIKDVDEKADIALIKIDHQGKLP  60
rat     1  GSGFIVSEDGLIVTNAHVVTNHNRVKVELKNGATYEAKIKDVDEKADIALIKIDHQGKLP  60 human   61 VLLLGRSSELRPGEFVVAIGSPFSLQNTVTTGIVSTTQRGGKELGLRNSDMDYIQTDAII 120
cyno.   61 VLLLGRSSELRPGEFVVAIGSPFSLQNTVTTGIVSTTQRGGKELGLRNSDMDYIQTDAII 120
rabbit  61 VLLLGRSSELRPGEFVVAIGSPFSLQNTVTTGIVSTTQRGGKELGLRNSDMDYIQTDAII 120
mouse   61 VLLLGRSSELRPGEFVVAIGSPFSLQNTVTTGIVSTTQRGGKELGLRNSDMDYIQTDAII 120
rat     61 VLLLGRSSELRPGEFVVAIGSPFSLQNTVTTGIVSTTQRGGKELGLRNSDMDYIQTDAII 120 human   121 NYGNSGGPLVNLDGEVIGINTLKVTAGISFAIPSDKIKKFL 161
cyno.   121 NYGNSGGPLVNLDGEVIGINTLKVTAGISFAIPSDKIKKFL 161
rabbit  121 NYGNSGGPLVNLDGEVIGINTLKVTAGISFAIPSDKIKKFL 161
mouse   121 NYGNSGGPLVNLDGEVIGINTLKVTAGISFAIPSDKIKKFL 161
rat     121 NYGNSGGPLVNLDGEVIGINTLKVTAGISFAIPSDKIKKFL 161
```

PRIMER 21

CCATCATCAACTACGGCAACGCGGGCGGACCCCTCGTGAACC (SEQ ID NO: 55)

[Figure 77]

PRIMER 22

GGTTCACGAGGGGTCCGCCCGCGTTGCCGTAGTTGATGATGG (SEQ ID NO: 56)

SEQUENCE LISTING

```
<160> NUMBER OF SEQ ID NOS: 69

<210> SEQ ID NO 1
<211> LENGTH: 63
<212> TYPE: PRT
<213> ORGANISM: Homo sapiens

<400> SEQUENCE: 1

Asp Pro Gln Phe Gly Leu Phe Ser Lys Tyr Arg Thr Pro Asn Cys Ser
1               5                   10                  15

Gln Tyr Arg Leu Pro Gly Cys Pro Arg His Phe Asn Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys
    50                  55                  60

<210> SEQ ID NO 2
<211> LENGTH: 192
<212> TYPE: DNA
<213> ORGANISM: Homo sapiens

<400> SEQUENCE: 2
gatccgcagt ttggtctgtt tagcaaatat cgtaccccga attgtagcca gtatcgtctg     60
cctggttgtc cgcgtcattt taatccggtt tgtggtagcg atatgagcac ctatgcaaat    120
gaatgtaccc tgtgcatgaa aattcgtgaa ggtggccata atattaaaat tattcgcaat    180
ggtccgtgct aa                                                       192

<210> SEQ ID NO 3
<211> LENGTH: 65
<212> TYPE: PRT
<213> ORGANISM: Artificial Sequence
<220> FEATURE:
<223> OTHER INFORMATION: Synthetic

<400> SEQUENCE: 3
```

```
Asp Pro Gln Phe Gly Leu Phe Ser Lys Tyr Arg Thr Pro Asn Cys Leu
1               5                   10                  15

Lys Ser Glu Gly Met Ala Cys Tyr Ala Tyr Tyr Glu Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 4
<211> LENGTH: 198
<212> TYPE: DNA
<213> ORGANISM: Artificial Sequence
<220> FEATURE:
<223> OTHER INFORMATION: Synthetic

<400> SEQUENCE: 4
gatccgcagt ttggtctgtt tagcaaatat cgtaccccga attgtctgaa atctgaaggt    60
atggcttgtt acgcttacta cgaaccggtt tgtggtagcg atatgagcac ctatgcaaat   120
gaatgtaccc tgtgcatgaa aattcgtgaa ggtggccata atattaaaat tattcgcaat   180
ggtccgtgcg gcggctaa                                                 198

<210> SEQ ID NO 5
<211> LENGTH: 65
<212> TYPE: PRT
<213> ORGANISM: Artificial Sequence
<220> FEATURE:
<223> OTHER INFORMATION: Synthetic

<400> SEQUENCE: 5

Asp Pro Gln Phe Gly Leu Phe Ser Lys Tyr Arg Thr Pro Asn Cys Thr
1               5                   10                  15

Met Asp Met Gly Met Ala Cys Trp Ala Phe Tyr Glu Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 6
<211> LENGTH: 198
<212> TYPE: DNA
<213> ORGANISM: Artificial Sequence
<220> FEATURE:
<223> OTHER INFORMATION: Synthetic

<400> SEQUENCE: 6
gatccgcagt ttggtctgtt tagcaaatat cgtaccccga attgtactat ggacatgggt    60
atggcttgtt gggcttttcta cgaaccggtt tgtggtagcg atatgagcac ctatgcaaat   120
gaatgtaccc tgtgcatgaa aattcgtgaa ggtggccata atattaaaat tattcgcaat   180
ggtccgtgcg gcggctaa                                                 198

<210> SEQ ID NO 7
```

<211> LENGTH: 65
<212> TYPE: PRT
<213> ORGANISM: Artificial Sequence
<220> FEATURE:
<223> OTHER INFORMATION: Synthetic

<400> SEQUENCE: 7

```
Asp Pro Gln Phe Gly Leu Phe Ser Lys Tyr Arg Thr Pro Asn Cys Gly
1               5                   10                  15
His Tyr Asn Gly Trp Ala Cys Gln Ala Phe Phe Glu Pro Val Cys Gly
            20                  25                  30
Ser Asp Met Ser Thr Tyr Ala Asn Glu Cys Thr Leu Cys Met Lys Ile
        35                  40                  45
Arg Glu Gly Gly His Asn Ile Lys Ile Ile Arg Asn Gly Pro Cys Gly
    50                  55                  60
Gly
65
```

<210> SEQ ID NO 8
<211> LENGTH: 198
<212> TYPE: DNA
<213> ORGANISM: Artificial Sequence
<220> FEATURE:
<223> OTHER INFORMATION: Synthetic

<400> SEQUENCE: 8

```
gatccgcagt tggtctgtt tagcaaatat cgtaccccga attgtggtca ttacaacggt      60
tgggcttgtc aggctttctt cgaaccggtt tgtggtagcg atatgagcac ctatgcaaat    120
gaatgtaccc tgtgcatgaa aattcgtgaa ggtggccata atattaaaat tattcgcaat    180
ggtccgtgcg gcggctaa                                                  198
```

<210> SEQ ID NO 9
<211> LENGTH: 65
<212> TYPE: PRT
<213> ORGANISM: Artificial Sequence
<220> FEATURE:
<223> OTHER INFORMATION: Synthetic

<400> SEQUENCE: 9

```
Asp Pro Gln Phe Gly Leu Phe Ser Lys Tyr Arg Thr Pro Asn Cys Ser
1               5                   10                  15
Asp His Ala Gly Met Ala Cys Val Ala Leu Tyr Glu Pro Val Cys Gly
            20                  25                  30
Ser Asp Met Ser Thr Tyr Glu Asn Glu Cys Val Leu Cys Met Lys Ile
        35                  40                  45
Arg Glu Gly Gly His Asn Ile Lys Ile Ile Arg Asn Gly Pro Cys Gly
    50                  55                  60
Gly
65
```

<210> SEQ ID NO 10
<211> LENGTH: 198
<212> TYPE: DNA
<213> ORGANISM: Artificial Sequence
<220> FEATURE:
<223> OTHER INFORMATION: Synthetic

<400> SEQUENCE: 10

```
gatccgcagt tggtctgtt tagcaaatat cgtaccccga attgtagcga ccatgctggt      60
atggcatgtg ttgctctgta tgaaccggtt tgtggtagcg atatgagcac ctatgaaaat    120
```

```
gaatgtgttc tgtgcatgaa aattcgtgaa ggtggccata atattaaaat tattcgcaat    180
ggtccgtgcg gcggctaa                                                  198
```

<210> SEQ ID NO 11
<211> LENGTH: 65
<212> TYPE: PRT
<213> ORGANISM: Artificial Sequence
<220> FEATURE:
<223> OTHER INFORMATION: Synthetic

<400> SEQUENCE: 11

Asp Pro Gln Phe Gly Leu Phe Ser Lys Tyr Arg Thr Pro Asn Cys Ser
1               5                   10                  15

Asp Phe Asp Gly Met Ala Cys Tyr Ala Phe Tyr Glu Pro Val Cys Gly
            20                  25                  30

Ser Asp Met Ser Thr Tyr Met Asn Glu Cys Ala Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 12
<211> LENGTH: 198
<212> TYPE: DNA
<213> ORGANISM: Artificial Sequence
<220> FEATURE:
<223> OTHER INFORMATION: Synthetic

<400> SEQUENCE: 12

```
gatccgcagt ttggtctgtt tagcaaatat cgtaccccga attgtagcga cttcgacggt    60
atggcatgtt acgctttcta tgaaccggtt tgtggtagcg atatgagcac ctatatgaat    120
gaatgtgctc tgtgcatgaa aattcgtgaa ggtggccata atattaaaat tattcgcaat    180
ggtccgtgcg gcggctaa                                                  198
```

<210> SEQ ID NO 13
<211> LENGTH: 65
<212> TYPE: PRT
<213> ORGANISM: Artificial Sequence
<220> FEATURE:
<223> OTHER INFORMATION: Synthetic

<400> SEQUENCE: 13

Asp Pro Gln Phe Gly Leu Phe Ser Lys Tyr Arg Thr Pro Asn Cys Ser
1               5                   10                  15

Gln His Glu Gly Met Ala Cys Tyr Ala Leu Tyr Glu Pro Val Cys Gly
            20                  25                  30

Ser Asp Met Ser Thr Tyr Val Asn Glu Cys Ala Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 14
<211> LENGTH: 198
<212> TYPE: DNA
<213> ORGANISM: Artificial Sequence
<220> FEATURE:

<223> OTHER INFORMATION: Synthetic

<400> SEQUENCE: 14

```
gatccgcagt ttggtctgtt tagcaaatat cgtaccccga attgtagcca gcatgaaggt    60
atggcatgtt acgctctgta tgaaccggtt tgtggtagcg atatgagcac ctatgttaat   120
gaatgtgctc tgtgcatgaa aattcgtgaa ggtggccata atattaaaat tattcgcaat   180
ggtccgtgcg gcggctaa                                                 198
```

<210> SEQ ID NO 15
<211> LENGTH: 65
<212> TYPE: PRT
<213> ORGANISM: Artificial Sequence
<220> FEATURE:
<223> OTHER INFORMATION: Synthetic

<400> SEQUENCE: 15

```
Asp Pro Gln Phe Gly Leu Phe Ser Lys Tyr Arg Thr Pro Asn Cys Ser
1               5                   10                  15

Asp His Ala Gly Met Ala Cys Val Ala Leu Tyr Glu Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65
```

<210> SEQ ID NO 16
<211> LENGTH: 198
<212> TYPE: DNA
<213> ORGANISM: Artificial Sequence
<220> FEATURE:
<223> OTHER INFORMATION: Synthetic

<400> SEQUENCE: 16

```
gatccgcagt ttggtctgtt tagcaaatat cgtaccccga attgtagcga ccatgctggt    60
atggcatgtg ttgctctgta tgaaccggtt tgtggtagcg atatgagcac ctatgcaaat   120
gaatgtaccc tgtgcatgaa aattcgtgaa ggtggccata atattaaaat tattcgcaat   180
ggtccgtgcg gcggctaa                                                 198
```

<210> SEQ ID NO 17
<211> LENGTH: 65
<212> TYPE: PRT
<213> ORGANISM: Artificial Sequence
<220> FEATURE:
<223> OTHER INFORMATION: Synthetic

<400> SEQUENCE: 17

```
Asp Pro Gln Phe Gly Leu Phe Ser Lys Tyr Arg Thr Pro Asn Cys Ser
1               5                   10                  15

Asp Phe Asp Gly Met Ala Cys Tyr Ala Phe Tyr Glu Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65
```

<210> SEQ ID NO 18
<211> LENGTH: 198
<212> TYPE: DNA
<213> ORGANISM: Artificial Sequence
<220> FEATURE:
<223> OTHER INFORMATION: Synthetic

<400> SEQUENCE: 18

```
gatccgcagt ttggtctgtt tagcaaatat cgtaccccga attgtagcga cttcgacggt      60
atggcatgtt acgctttcta tgaaccggtt tgtggtagcg atatgagcac ctatgcaaat     120
gaatgtaccc tgtgcatgaa aattcgtgaa ggtggccata atattaaaat tattcgcaat     180
ggtccgtgcg gcggctaa                                                   198
```

<210> SEQ ID NO 19
<211> LENGTH: 65
<212> TYPE: PRT
<213> ORGANISM: Artificial Sequence
<220> FEATURE:
<223> OTHER INFORMATION: Synthetic

<400> SEQUENCE: 19

Asp Pro Gln Phe Gly Leu Phe Ser Lys Tyr Arg Thr Pro Asn Cys Ser
1               5                   10                  15

Gln His Glu Gly Met Ala Cys Tyr Ala Leu Tyr Glu Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 20
<211> LENGTH: 198
<212> TYPE: DNA
<213> ORGANISM: Artificial Sequence
<220> FEATURE:
<223> OTHER INFORMATION: Synthetic

<400> SEQUENCE: 20

```
gatccgcagt ttggtctgtt tagcaaatat cgtaccccga attgtagcca gcatgaaggt      60
atggcatgtt acgctctgta tgaaccggtt tgtggtagcg atatgagcac ctatgcaaat     120
gaatgtaccc tgtgcatgaa aattcgtgaa ggtggccata atattaaaat tattcgcaat     180
ggtccgtgcg gcggctaa                                                   198
```

<210> SEQ ID NO 21
<211> LENGTH: 65
<212> TYPE: PRT
<213> ORGANISM: Artificial Sequence
<220> FEATURE:
<223> OTHER INFORMATION: Synthetic

<400> SEQUENCE: 21

Asp Pro Gln Phe Gly Leu Phe Ser Lys Tyr Arg Thr Pro Asn Cys Ser
1               5                   10                  15

Asp His Ala Gly Met Ala Cys Val Ala Phe Tyr Glu Pro Val Cys Gly
            20                  25                  30

Ser Asp Met Ser Thr Tyr Ala Asn Glu Cys Thr Leu Cys Met Lys Ile

```
            35                  40                  45

Arg Glu Gly Gly His Asn Ile Lys Ile Ile Arg Asn Gly Pro Cys Gly
    50                  55                  60

Gly
65

<210> SEQ ID NO 22
<211> LENGTH: 198
<212> TYPE: DNA
<213> ORGANISM: Artificial Sequence
<220> FEATURE:
<223> OTHER INFORMATION: Synthetic

<400> SEQUENCE: 22
gatccgcagt tggtctgtt tagcaaatat cgtaccccga attgtagcga ccatgctggt      60
atggcatgtg ttgcttttta tgaaccggtt tgtggtagcg atatgagcac ctatgcaaat    120
gaatgtaccc tgtgcatgaa aattcgtgaa ggtggccata atattaaaat tattcgcaat    180
ggtccgtgcg gcggctaa                                                  198

<210> SEQ ID NO 23
<211> LENGTH: 65
<212> TYPE: PRT
<213> ORGANISM: Artificial Sequence
<220> FEATURE:
<223> OTHER INFORMATION: Synthetic

<400> SEQUENCE: 23

Asp Pro Gln Phe Gly Leu Phe Ser Lys Tyr Arg Thr Pro Asn Cys Ala
1               5                   10                  15

Asp His Ala Gly Met Ala Cys Val Ala Leu Tyr Glu Pro Val Cys Gly
            20                  25                  30

Ser Asp Met Ser Thr Tyr Glu Asn Glu Cys Val Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 24
<211> LENGTH: 65
<212> TYPE: PRT
<213> ORGANISM: Artificial Sequence
<220> FEATURE:
<223> OTHER INFORMATION: Synthetic

<400> SEQUENCE: 24

Gly Pro Gln Phe Gly Leu Phe Ser Lys Tyr Arg Thr Pro Asn Cys Ala
1               5                   10                  15

Asp His Ala Gly Met Ala Cys Val Ala Leu Tyr Glu Pro Val Cys Gly
            20                  25                  30

Ser Asp Met Ser Thr Tyr Glu Asn Glu Cys Val Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 25
<211> LENGTH: 65
```

<212> TYPE: PRT
<213> ORGANISM: Artificial Sequence
<220> FEATURE:
<223> OTHER INFORMATION: Synthetic

<400> SEQUENCE: 25

```
Ser Pro Gln Phe Gly Leu Phe Ser Lys Tyr Arg Thr Pro Asn Cys Ala
1               5                   10                  15
Asp His Ala Gly Met Ala Cys Val Ala Leu Tyr Glu Pro Val Cys Gly
            20                  25                  30
Ser Asp Met Ser Thr Tyr Glu Asn Glu Cys Val Leu Cys Met Lys Ile
        35                  40                  45
Arg Glu Gly Gly His Asn Ile Lys Ile Ile Arg Asn Gly Pro Cys Gly
    50                  55                  60
Gly
65
```

<210> SEQ ID NO 26
<211> LENGTH: 65
<212> TYPE: PRT
<213> ORGANISM: Artificial Sequence
<220> FEATURE:
<223> OTHER INFORMATION: Synthetic

<400> SEQUENCE: 26

```
Glu Pro Gln Phe Gly Leu Phe Ser Lys Tyr Arg Thr Pro Asn Cys Ala
1               5                   10                  15
Asp His Ala Gly Met Ala Cys Val Ala Leu Tyr Glu Pro Val Cys Gly
            20                  25                  30
Ser Asp Met Ser Thr Tyr Glu Asn Glu Cys Val Leu Cys Met Lys Ile
        35                  40                  45
Arg Glu Gly Gly His Asn Ile Lys Ile Ile Arg Asn Gly Pro Cys Gly
    50                  55                  60
Gly
65
```

<210> SEQ ID NO 27
<211> LENGTH: 67
<212> TYPE: PRT
<213> ORGANISM: Artificial Sequence
<220> FEATURE:
<223> OTHER INFORMATION: Synthetic

<400> SEQUENCE: 27

```
Ser Leu Ile Pro Gln Phe Gly Leu Phe Ser Lys Tyr Arg Thr Pro Asn
1               5                   10                  15
Cys Ala Asp His Ala Gly Met Ala Cys Val Ala Leu Tyr Glu Pro Val
            20                  25                  30
Cys Gly Ser Asp Met Ser Thr Tyr Glu Asn Glu Cys Val Leu Cys Met
        35                  40                  45
Lys Ile Arg Glu Gly Gly His Asn Ile Lys Ile Ile Arg Asn Gly Pro
    50                  55                  60
Cys Gly Gly
65
```

<210> SEQ ID NO 28
<211> LENGTH: 65
<212> TYPE: PRT
<213> ORGANISM: Artificial Sequence
<220> FEATURE:
<223> OTHER INFORMATION: Synthetic

<400> SEQUENCE: 28

Gly Pro Gln Phe Gly Leu Phe Ser Lys Tyr Arg Thr Pro Asn Cys Ala
1               5                   10                  15

Asp Phe Asp Gly Met Ala Cys Tyr Ala Phe Tyr Glu Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 29
<211> LENGTH: 65
<212> TYPE: PRT
<213> ORGANISM: Artificial Sequence
<220> FEATURE:
<223> OTHER INFORMATION: Synthetic

<400> SEQUENCE: 29

Gly Pro Gln Phe Gly Leu Phe Ser Lys Tyr Arg Thr Pro Asn Cys Ala
1               5                   10                  15

Gln His Glu Gly Met Ala Cys Tyr Ala Leu Tyr Glu Pro Val Cys Gly
            20                  25                  30

Ser Asp Met Ser Thr Tyr Ala Asn Glu Cys Thr Leu Cys Met Lys Ile
        35                  40                  45

Arg Glu Gly Gly His Asn Ile Lys Ile Ile Arg Asn Gly Pro Cys Gly
    50                  55                  60

Gly
65

<210> SEQ ID NO 30
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Wherein X at position 1 is defined as any amino
    acid
<220> FEATURE:
<221> NAME/KEY: MISC_FEATURE
<222> LOCATION: (16)..(19)
<223> OTHER INFORMATION: Wherein X at positions 16 through 19 is defined
    as any amino acid
<220> FEATURE:
<221> NAME/KEY: MISC_FEATURE
<222> LOCATION: (21)..(21)
<223> OTHER INFORMATION: Wherein X at position 21 is defined as any
    amino acid
<220> FEATURE:
<221> NAME/KEY: MISC_FEATURE
<222> LOCATION: (24)..(24)
<223> OTHER INFORMATION: Wherein X at position 24 is defined as any
    amino acid
<220> FEATURE:
<221> NAME/KEY: MISC_FEATURE
<222> LOCATION: (26)..(26)
<223> OTHER INFORMATION: Wherein X at position 26 is defined as any
    amino acid
<220> FEATURE:
<221> NAME/KEY: MISC_FEATURE
<222> LOCATION: (27)..(27)
<223> OTHER INFORMATION: Wherein X at position 27 is defined as any

```
              amino acid
<220> FEATURE:
<221> NAME/KEY: MISC_FEATURE
<222> LOCATION: (39)..(39)
<223> OTHER INFORMATION: Wherein X at position 39 is defined as any
              amino acid
<220> FEATURE:
<221> NAME/KEY: MISC_FEATURE
<222> LOCATION: (43)..(43)
<223> OTHER INFORMATION: Wherein X at position 43 is defined as any
              amino acid

<400> SEQUENCE: 30

Xaa Pro Gln Phe Gly Leu Phe Ser Lys Tyr Arg Thr Pro Asn Cys Xaa
1               5                   10                  15

Xaa Xaa Xaa Gly Xaa Ala Cys Xaa Ala Xaa Xaa Glu Pro Val Cys Gly
            20                  25                  30

Ser Asp Met Ser Thr Tyr Xaa Asn Glu Cys Xaa Leu Cys Met Lys Ile
        35                  40                  45

Arg Glu Gly Gly His Asn Ile Lys Ile Ile Arg Asn Gly Pro Cys
    50                  55                  60

<210> SEQ ID NO 31
<211> LENGTH: 39
<212> TYPE: PRT
<213> ORGANISM: Artificial Sequence
<220> FEATURE:
<223> OTHER INFORMATION: Synthetic

<400> SEQUENCE: 31

Gly Ser Gly Met Lys Glu Thr Ala Ala Ala Lys Phe Glu Arg Gln His
1               5                   10                  15

Met Asp Ser Pro Asp Leu Gly Thr Asp Asp Asp Lys Ala Met Ala
            20                  25                  30

Asp Ile Gly Ser Ala Asn Ser
        35

<210> SEQ ID NO 32
<211> LENGTH: 6
<212> TYPE: PRT
<213> ORGANISM: Artificial Sequence
<220> FEATURE:
<223> OTHER INFORMATION: Synthetic

<400> SEQUENCE: 32

Gly Ala Ser Ala Ala Ala
1               5

<210> SEQ ID NO 33
<211> LENGTH: 34
<212> TYPE: DNA
<213> ORGANISM: Artificial Sequence
<220> FEATURE:
<223> OTHER INFORMATION: Synthetic

<400> SEQUENCE: 33
aaaagaattc tgatccgcag tttggtctgt ttag                         34

<210> SEQ ID NO 34
<211> LENGTH: 40
<212> TYPE: DNA
<213> ORGANISM: Artificial Sequence
<220> FEATURE:
<223> OTHER INFORMATION: Synthetic

<400> SEQUENCE: 34
```

```
aaaactcgag ttatgcggcc gcagacgcgc cgcacggacc                    40
```

<210> SEQ ID NO 35
<211> LENGTH: 45
<212> TYPE: DNA
<213> ORGANISM: Artificial Sequence
<220> FEATURE:
<223> OTHER INFORMATION: Synthetic

<400> SEQUENCE: 35

```
aaaaggatcc ctggacaaac gtgatccgca gtttggtctg tttag             45
```

<210> SEQ ID NO 36
<211> LENGTH: 44
<212> TYPE: DNA
<213> ORGANISM: Artificial Sequence
<220> FEATURE:
<223> OTHER INFORMATION: Synthetic

<400> SEQUENCE: 36

```
aaaactcgag ttagccgccg cacggaccat tgcgaataat ttta              44
```

<210> SEQ ID NO 37
<211> LENGTH: 34
<212> TYPE: DNA
<213> ORGANISM: Artificial Sequence
<220> FEATURE:
<223> OTHER INFORMATION: Synthetic

<400> SEQUENCE: 37

```
aaacatatgg ggcaggaaga tcccaacagt ttgc                         34
```

<210> SEQ ID NO 38
<211> LENGTH: 33
<212> TYPE: DNA
<213> ORGANISM: Artificial Sequence
<220> FEATURE:
<223> OTHER INFORMATION: Synthetic

<400> SEQUENCE: 38

```
aaactcgagt ttggcctgtc ggtcatggga ctc                          33
```

<210> SEQ ID NO 39
<211> LENGTH: 35
<212> TYPE: DNA
<213> ORGANISM: Artificial Sequence
<220> FEATURE:
<223> OTHER INFORMATION: Synthetic

<400> SEQUENCE: 39

```
aaaagaattc gccaccatgc agattcctag agccg                        35
```

<210> SEQ ID NO 40
<211> LENGTH: 36
<212> TYPE: DNA
<213> ORGANISM: Artificial Sequence
<220> FEATURE:
<223> OTHER INFORMATION: Synthetic

<400> SEQUENCE: 40

```
aaaactcgag tcagtggtga tggtggtggt ggccgg                       36
```

<210> SEQ ID NO 41
<211> LENGTH: 42
<212> TYPE: DNA

<213> ORGANISM: Artificial Sequence
<220> FEATURE:
<223> OTHER INFORMATION: Synthetic

<400> SEQUENCE: 41
cttgtcgtca tcgtccttgt agtcgccggg gtcgatttcc tc            42

<210> SEQ ID NO 42
<211> LENGTH: 44
<212> TYPE: DNA
<213> ORGANISM: Artificial Sequence
<220> FEATURE:
<223> OTHER INFORMATION: Synthetic

<400> SEQUENCE: 42
gcgactacaa ggacgatgac gacaagcacc accaccatca tcac          44

<210> SEQ ID NO 43
<211> LENGTH: 41
<212> TYPE: DNA
<213> ORGANISM: Artificial Sequence
<220> FEATURE:
<223> OTHER INFORMATION: Synthetic

<400> SEQUENCE: 43
aaaaactcga gctagtgatg atggtggtgg tgcttgtcgt c             41

<210> SEQ ID NO 44
<211> LENGTH: 42
<212> TYPE: DNA
<213> ORGANISM: Artificial Sequence
<220> FEATURE:
<223> OTHER INFORMATION: Synthetic

<400> SEQUENCE: 44
ccgcagtttg gtctgtttag caaatatcgt accccgaatt gt            42

<210> SEQ ID NO 45
<211> LENGTH: 43
<212> TYPE: DNA
<213> ORGANISM: Artificial Sequence
<220> FEATURE:
<223> OTHER INFORMATION: Synthetic

<400> SEQUENCE: 45
gccataccag catggtccgc acaattcggg gtacgatatt tgc           43

<210> SEQ ID NO 46
<211> LENGTH: 40
<212> TYPE: DNA
<213> ORGANISM: Artificial Sequence
<220> FEATURE:
<223> OTHER INFORMATION: Synthetic

<400> SEQUENCE: 46
gcggaccatg ctggtatggc atgtgttgct ctgtatgaac               40

<210> SEQ ID NO 47
<211> LENGTH: 39
<212> TYPE: DNA
<213> ORGANISM: Artificial Sequence
<220> FEATURE:
<223> OTHER INFORMATION: Synthetic

<400> SEQUENCE: 47
aaaactcgag ttagccgccg cacggaccat tgcgaataa                39

<210> SEQ ID NO 48
<211> LENGTH: 45
<212> TYPE: DNA
<213> ORGANISM: Artificial Sequence
<220> FEATURE:
<223> OTHER INFORMATION: Synthetic

<400> SEQUENCE: 48
aaaaggatcc ctggacaaac gtgatccgca gtttggtctg tttag    45

<210> SEQ ID NO 49
<211> LENGTH: 45
<212> TYPE: DNA
<213> ORGANISM: Artificial Sequence
<220> FEATURE:
<223> OTHER INFORMATION: Synthetic

<400> SEQUENCE: 49
aaaaggatcc ctggacaaac gtggcccgca gtttggtctg tttag    45

<210> SEQ ID NO 50
<211> LENGTH: 45
<212> TYPE: DNA
<213> ORGANISM: artificial Sequence
<220> FEATURE:
<223> OTHER INFORMATION: Synthetic

<400> SEQUENCE: 50
aaaaggatcc ctggacaaac gtagcccgca gtttggtctg tttag    45

<210> SEQ ID NO 51
<211> LENGTH: 45
<212> TYPE: DNA
<213> ORGANISM: Artificial Sequence
<220> FEATURE:
<223> OTHER INFORMATION: Synthetic

<400> SEQUENCE: 51
aaaaggatcc ctggacaaac gtgaaccgca gtttggtctg tttag    45

<210> SEQ ID NO 52
<211> LENGTH: 51
<212> TYPE: DNA
<213> ORGANISM: Artificial Sequence
<220> FEATURE:
<223> OTHER INFORMATION: Synthetic

<400> SEQUENCE: 52
aaaaggatcc ctggacaaac gtagcctgat tccgcagttt ggtctgttta g    51

<210> SEQ ID NO 53
<211> LENGTH: 458
<212> TYPE: PRT
<213> ORGANISM: Homo sapiens

<400> SEQUENCE: 53

Gln Leu Ser Arg Ala Gly Arg Ser Ala Pro Leu Ala Ala Gly Cys Pro
1               5                   10                  15

Asp Arg Cys Glu Pro Ala Arg Cys Pro Pro Gln Pro Glu His Cys Glu
                20                  25                  30

Gly Gly Arg Ala Arg Asp Ala Cys Gly Cys Cys Glu Val Cys Gly Ala
            35                  40                  45

Pro Glu Gly Ala Ala Cys Gly Leu Gln Glu Gly Pro Cys Gly Glu Gly

```
            50                  55                  60
Leu Gln Cys Val Val Pro Phe Gly Val Pro Ala Ser Ala Thr Val Arg
 65                  70                  75                  80

Arg Arg Ala Gln Ala Gly Leu Cys Val Cys Ala Ser Ser Glu Pro Val
                 85                  90                  95

Cys Gly Ser Asp Ala Asn Thr Tyr Ala Asn Leu Cys Gln Leu Arg Ala
            100                 105                 110

Ala Ser Arg Arg Ser Glu Arg Leu His Arg Pro Pro Val Ile Val Leu
            115                 120                 125

Gln Arg Gly Ala Cys Gly Gln Gly Gln Glu Asp Pro Asn Ser Leu Arg
            130                 135                 140

His Lys Tyr Asn Phe Ile Ala Asp Val Val Glu Lys Ile Ala Pro Ala
145                 150                 155                 160

Val Val His Ile Glu Leu Phe Arg Lys Leu Pro Phe Ser Lys Arg Glu
                165                 170                 175

Val Pro Val Ala Ser Gly Ser Gly Phe Ile Val Ser Glu Asp Gly Leu
            180                 185                 190

Ile Val Thr Asn Ala His Val Val Thr Asn Lys His Arg Val Lys Val
            195                 200                 205

Glu Leu Lys Asn Gly Ala Thr Tyr Glu Ala Lys Ile Lys Asp Val Asp
    210                 215                 220

Glu Lys Ala Asp Ile Ala Leu Ile Lys Ile Asp His Gln Gly Lys Leu
225                 230                 235                 240

Pro Val Leu Leu Leu Gly Arg Ser Ser Glu Leu Arg Pro Gly Glu Phe
                245                 250                 255

Val Val Ala Ile Gly Ser Pro Phe Ser Leu Gln Asn Thr Val Thr Thr
            260                 265                 270

Gly Ile Val Ser Thr Thr Gln Arg Gly Gly Lys Glu Leu Gly Leu Arg
            275                 280                 285

Asn Ser Asp Met Asp Tyr Ile Gln Thr Asp Ala Ile Ile Asn Tyr Gly
    290                 295                 300

Asn Ser Gly Gly Pro Leu Val Asn Leu Asp Gly Glu Val Ile Gly Ile
305                 310                 315                 320

Asn Thr Leu Lys Val Thr Ala Gly Ile Ser Phe Ala Ile Pro Ser Asp
                325                 330                 335

Lys Ile Lys Lys Phe Leu Thr Glu Ser His Asp Arg Gln Ala Lys Gly
            340                 345                 350

Lys Ala Ile Thr Lys Lys Tyr Ile Gly Ile Arg Met Met Ser Leu
            355                 360                 365

Thr Ser Ser Lys Ala Lys Glu Leu Lys Asp Arg His Arg Asp Phe Pro
    370                 375                 380

Asp Val Ile Ser Gly Ala Tyr Ile Ile Glu Val Ile Pro Asp Thr Pro
385                 390                 395                 400

Ala Glu Ala Gly Gly Leu Lys Glu Asn Asp Val Ile Ile Ser Ile Asn
                405                 410                 415

Gly Gln Ser Val Val Ser Ala Asn Asp Val Ser Asp Val Ile Lys Arg
            420                 425                 430

Glu Ser Thr Leu Asn Met Val Arg Arg Gly Asn Glu Asp Ile Met
            435                 440                 445

Ile Thr Val Ile Pro Glu Glu Ile Asp Pro
    450                 455

<210> SEQ ID NO 54
```

```
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: BINDING
<222> LOCATION: (1)..(1)
<223> OTHER INFORMATION: Wherein X at position 1 is defined as
      N-(4-methylcoumaryl-7-amide)-isoleucine
<220> FEATURE:
<221> NAME/KEY: BINDING
<222> LOCATION: (10)..(10)
<223> OTHER INFORMATION: Wherein X at position 10 is defined as N
      epsilon-(2,4-dinitrophenyl)-lysine

<400> SEQUENCE: 54

Xaa Arg Arg Val Ser Tyr Ser Phe Lys Xaa
1               5                   10

<210> SEQ ID NO 55
<211> LENGTH: 42
<212> TYPE: DNA
<213> ORGANISM: Artificial Sequence
<220> FEATURE:
<223> OTHER INFORMATION: Synthetic

<400> SEQUENCE: 55
ccatcatcaa ctacggcaac gcgggcggac ccctcgtgaa cc                       42

<210> SEQ ID NO 56
<211> LENGTH: 42
<212> TYPE: DNA
<213> ORGANISM: Artificial Sequence
<220> FEATURE:
<223> OTHER INFORMATION: Synthetic

<400> SEQUENCE: 56
ggttcacgag gggtccgccc gcgttgccgt agttgatgat gg                       42

<210> SEQ ID NO 57
<211> LENGTH: 480
<212> TYPE: PRT
<213> ORGANISM: Homo sapiens

<400> SEQUENCE: 57

Met Gln Ile Pro Arg Ala Ala Leu Leu Pro Leu Leu Leu Leu Leu Leu
1               5                   10                  15

Ala Ala Pro Ala Ser Ala Gln Leu Ser Arg Ala Gly Arg Ser Ala Pro
            20                  25                  30

Leu Ala Ala Gly Cys Pro Asp Arg Cys Glu Pro Ala Arg Cys Pro Pro
        35                  40                  45

Gln Pro Glu His Cys Glu Gly Gly Arg Ala Arg Asp Ala Cys Gly Cys
    50                  55                  60

Cys Glu Val Cys Gly Ala Pro Glu Gly Ala Ala Cys Gly Leu Gln Glu
65                  70                  75                  80

Gly Pro Cys Gly Glu Gly Leu Gln Cys Val Val Pro Phe Gly Val Pro
                85                  90                  95

Ala Ser Ala Thr Val Arg Arg Arg Ala Gln Ala Gly Leu Cys Val Cys
            100                 105                 110

Ala Ser Ser Glu Pro Val Cys Gly Ser Asp Ala Asn Thr Tyr Ala Asn
        115                 120                 125

Leu Cys Gln Leu Arg Ala Ala Ser Arg Arg Ser Glu Arg Leu His Arg
    130                 135                 140
```

Pro Pro Val Ile Val Leu Gln Arg Gly Ala Cys Gly Gln Gly Gln Glu
145                 150                 155                 160

Asp Pro Asn Ser Leu Arg His Lys Tyr Asn Phe Ile Ala Asp Val Val
                165                 170                 175

Glu Lys Ile Ala Pro Ala Val Val His Ile Glu Leu Phe Arg Lys Leu
            180                 185                 190

Pro Phe Ser Lys Arg Glu Val Pro Val Ala Ser Gly Ser Gly Phe Ile
        195                 200                 205

Val Ser Glu Asp Gly Leu Ile Val Thr Asn Ala His Val Val Thr Asn
    210                 215                 220

Lys His Arg Val Lys Val Glu Leu Lys Asn Gly Ala Thr Tyr Glu Ala
225                 230                 235                 240

Lys Ile Lys Asp Val Asp Glu Lys Ala Asp Ile Ala Leu Ile Lys Ile
                245                 250                 255

Asp His Gln Gly Lys Leu Pro Val Leu Leu Leu Gly Arg Ser Ser Glu
                260                 265                 270

Leu Arg Pro Gly Glu Phe Val Val Ala Ile Gly Ser Pro Phe Ser Leu
        275                 280                 285

Gln Asn Thr Val Thr Thr Gly Ile Val Ser Thr Gln Arg Gly Gly
    290                 295                 300

Lys Glu Leu Gly Leu Arg Asn Ser Asp Met Asp Tyr Ile Gln Thr Asp
305                 310                 315                 320

Ala Ile Ile Asn Tyr Gly Asn Ser Gly Gly Pro Leu Val Asn Leu Asp
                325                 330                 335

Gly Glu Val Ile Gly Ile Asn Thr Leu Lys Val Thr Ala Gly Ile Ser
                340                 345                 350

Phe Ala Ile Pro Ser Asp Lys Ile Lys Lys Phe Leu Thr Glu Ser His
            355                 360                 365

Asp Arg Gln Ala Lys Gly Lys Ala Ile Thr Lys Lys Lys Tyr Ile Gly
        370                 375                 380

Ile Arg Met Met Ser Leu Thr Ser Ser Lys Ala Lys Glu Leu Lys Asp
385                 390                 395                 400

Arg His Arg Asp Phe Pro Asp Val Ile Ser Gly Ala Tyr Ile Ile Glu
                405                 410                 415

Val Ile Pro Asp Thr Pro Ala Glu Ala Gly Gly Leu Lys Glu Asn Asp
                420                 425                 430

Val Ile Ile Ser Ile Asn Gly Gln Ser Val Val Ser Ala Asn Asp Val
            435                 440                 445

Ser Asp Val Ile Lys Arg Glu Ser Thr Leu Asn Met Val Val Arg Arg
        450                 455                 460

Gly Asn Glu Asp Ile Met Ile Thr Val Ile Pro Glu Glu Ile Asp Pro
465                 470                 475                 480

<210> SEQ ID NO 58
<211> LENGTH: 480
<212> TYPE: PRT
<213> ORGANISM: Mus musculus

<400> SEQUENCE: 58

Met Gln Ser Leu Arg Thr Thr Leu Leu Ser Leu Leu Leu Leu Leu Leu
1               5                   10                  15

Ala Ala Pro Ser Leu Ala Leu Pro Ser Gly Thr Gly Arg Ser Ala Pro
            20                  25                  30

Ala Ala Thr Val Cys Pro Glu His Cys Asp Pro Thr Arg Cys Ala Pro

```
            35                  40                  45
Pro Pro Thr Asp Cys Glu Gly Gly Arg Val Arg Asp Ala Cys Gly Cys
 50                  55                  60

Cys Glu Val Cys Gly Ala Leu Glu Gly Ala Ala Cys Gly Leu Gln Glu
 65              70                  75                  80

Gly Pro Cys Gly Glu Gly Leu Gln Cys Val Pro Phe Gly Val Pro
                 85                  90                  95

Ala Ser Ala Thr Val Arg Arg Ala Gln Ala Gly Leu Cys Val Cys
             100                 105                 110

Ala Ser Ser Glu Pro Val Cys Gly Ser Asp Ala Lys Thr Tyr Thr Asn
             115                 120                 125

Leu Cys Gln Leu Arg Ala Ala Ser Arg Arg Ser Glu Lys Leu Arg Gln
         130                 135                 140

Pro Pro Val Ile Val Leu Gln Arg Gly Ala Cys Gly Gln Gly Gln Glu
145                 150                 155                 160

Asp Pro Asn Ser Leu Arg His Lys Tyr Asn Phe Ile Ala Asp Val Val
                 165                 170                 175

Glu Lys Ile Ala Pro Ala Val Val His Ile Glu Leu Tyr Arg Lys Leu
             180                 185                 190

Pro Phe Ser Lys Arg Glu Val Pro Val Ala Ser Gly Ser Gly Phe Ile
         195                 200                 205

Val Ser Glu Asp Gly Leu Ile Val Thr Asn Ala His Val Val Thr Asn
210                 215                 220

Lys Asn Arg Val Lys Val Glu Leu Lys Asn Gly Ala Thr Tyr Glu Ala
225                 230                 235                 240

Lys Ile Lys Asp Val Asp Glu Lys Ala Asp Ile Ala Leu Ile Lys Ile
                 245                 250                 255

Asp His Gln Gly Lys Leu Pro Val Leu Leu Gly Arg Ser Ser Glu
             260                 265                 270

Leu Arg Pro Gly Glu Phe Val Val Ala Ile Gly Ser Pro Phe Ser Leu
         275                 280                 285

Gln Asn Thr Val Thr Thr Gly Ile Val Ser Thr Thr Gln Arg Gly Gly
    290                 295                 300

Lys Glu Leu Gly Leu Arg Asn Ser Asp Met Asp Tyr Ile Gln Thr Asp
305                 310                 315                 320

Ala Ile Ile Asn Tyr Gly Asn Ser Gly Gly Pro Leu Val Asn Leu Asp
                 325                 330                 335

Gly Glu Val Ile Gly Ile Asn Thr Leu Lys Val Thr Ala Gly Ile Ser
             340                 345                 350

Phe Ala Ile Pro Ser Asp Lys Ile Lys Lys Phe Leu Thr Glu Ser His
         355                 360                 365

Asp Arg Gln Ala Lys Gly Lys Ala Val Thr Lys Lys Tyr Ile Gly
    370                 375                 380

Ile Arg Met Met Ser Leu Thr Ser Ser Lys Ala Lys Glu Leu Lys Asp
385                 390                 395                 400

Arg His Arg Asp Phe Pro Asp Val Leu Ser Gly Ala Tyr Ile Ile Glu
                 405                 410                 415

Val Ile Pro Asp Thr Pro Ala Glu Ala Gly Gly Leu Lys Glu Asn Asp
             420                 425                 430

Val Ile Ile Ser Ile Asn Gly Gln Ser Val Val Thr Ala Asn Asp Val
         435                 440                 445

Ser Asp Val Ile Lys Lys Glu Asn Thr Leu Asn Met Val Val Arg Arg
    450                 455                 460
```

Gly Asn Glu Asp Ile Val Ile Thr Val Ile Pro Gly Glu Ile Asp Pro
465                 470                 475                 480

<210> SEQ ID NO 59
<211> LENGTH: 480
<212> TYPE: PRT
<213> ORGANISM: Rattus norvegicus

<400> SEQUENCE: 59

Met Gln Phe Leu Arg Thr Ala Leu Leu Ser Leu Leu Leu Leu Leu Leu
1               5                   10                  15

Ala Ala Pro Ser Leu Ala Leu Pro Ser Gly Ile Ser Arg Ser Ala Pro
            20                  25                  30

Ala Ala Thr Val Cys Pro Glu His Cys Asp Pro Thr Arg Cys Ala Pro
        35                  40                  45

Pro Pro Thr Asp Cys Glu Gly Gly Arg Val Arg Asp Ala Cys Gly Cys
    50                  55                  60

Cys Glu Val Cys Gly Ala Leu Glu Gly Ala Val Cys Gly Leu Gln Glu
65                  70                  75                  80

Gly Pro Cys Gly Glu Gly Leu Gln Cys Val Val Pro Phe Gly Val Pro
                85                  90                  95

Ala Ser Ala Thr Val Arg Arg Arg Ala Gln Ala Gly Leu Cys Val Cys
            100                 105                 110

Ala Ser Ser Glu Pro Val Cys Gly Ser Asp Ala Lys Thr Tyr Thr Asn
        115                 120                 125

Leu Cys Gln Leu Arg Ala Ala Ser Arg Arg Ser Glu Lys Leu Arg Gln
    130                 135                 140

Pro Pro Val Ile Val Leu Gln Arg Gly Ala Cys Gly Gln Gly Gln Glu
145                 150                 155                 160

Asp Pro Asn Ser Leu Arg His Lys Tyr Asn Phe Ile Ala Asp Val Val
                165                 170                 175

Glu Lys Ile Ala Pro Ala Val Val His Ile Glu Leu Tyr Arg Lys Leu
            180                 185                 190

Pro Phe Ser Lys Arg Glu Val Pro Val Ala Ser Gly Ser Gly Phe Ile
        195                 200                 205

Val Ser Glu Asp Gly Leu Ile Val Thr Asn Ala His Val Val Thr Asn
    210                 215                 220

Lys Asn Arg Val Lys Val Glu Leu Lys Asn Gly Ala Thr Tyr Glu Ala
225                 230                 235                 240

Lys Ile Lys Asp Val Asp Glu Lys Ala Asp Ile Ala Leu Ile Lys Ile
                245                 250                 255

Asp His Gln Gly Lys Leu Pro Val Leu Leu Leu Gly Arg Ser Ser Glu
            260                 265                 270

Leu Arg Pro Gly Glu Phe Val Val Ala Ile Gly Ser Pro Phe Ser Leu
        275                 280                 285

Gln Asn Thr Val Thr Thr Gly Ile Val Ser Thr Gln Arg Gly Gly
    290                 295                 300

Lys Glu Leu Gly Leu Arg Asn Ser Asp Met Asp Tyr Ile Gln Thr Asp
305                 310                 315                 320

Ala Ile Ile Asn Tyr Gly Asn Ser Gly Pro Leu Val Asn Leu Asp
                325                 330                 335

Gly Glu Val Ile Gly Ile Asn Thr Leu Lys Val Thr Ala Gly Ile Ser
            340                 345                 350

Phe Ala Ile Pro Ser Asp Lys Ile Lys Lys Phe Leu Thr Glu Ser His

```
                355                 360                 365
Asp Arg Gln Ala Lys Gly Lys Thr Val Thr Lys Lys Tyr Ile Gly
370                 375                 380

Ile Arg Met Met Ser Leu Thr Ser Ser Lys Ala Lys Glu Leu Lys Asp
385                 390                 395                 400

Arg His Arg Asp Phe Pro Asp Val Ile Ser Gly Ala Tyr Ile Ile Glu
                    405                 410                 415

Val Ile Pro Asp Thr Pro Ala Glu Ala Gly Gly Leu Lys Glu Asn Asp
            420                 425                 430

Val Ile Ile Ser Ile Asn Gly Gln Ser Val Val Thr Ala Asn Asp Val
            435                 440                 445

Ser Asp Val Ile Lys Lys Glu Asn Thr Leu Asn Met Val Val Arg Arg
450                 455                 460

Gly Asn Glu Asp Ile Val Ile Thr Val Val Pro Glu Glu Ile Asp Pro
465                 470                 475                 480
```

<210> SEQ ID NO 60
<211> LENGTH: 481
<212> TYPE: PRT
<213> ORGANISM: Macaca fascicularis

<400> SEQUENCE: 60

```
Met Gln Ile Pro Arg Ala Ala Leu Leu Pro Leu Leu Leu Leu Leu
1               5                   10                  15

Leu Ala Ala Pro Ala Ser Ala Gln Leu Ser Arg Ala Gly Arg Ser Ala
                20                  25                  30

Pro Leu Ala Thr Gly Cys Pro Glu Arg Cys Glu Pro Ala Arg Cys Pro
            35                  40                  45

Pro Gln Pro Glu His Cys Glu Gly Gly Arg Ala Arg Asp Ala Cys Gly
        50                  55                  60

Cys Cys Glu Val Cys Gly Ala Pro Gly Glu Ala Cys Gly Leu Gln
65                  70                  75              80

Glu Gly Pro Cys Gly Glu Gly Leu Gln Cys Val Val Pro Phe Gly Val
                85                  90                  95

Pro Ala Ser Ala Thr Val Arg Arg Arg Ala Gln Ala Gly Leu Cys Val
            100                 105                 110

Cys Ala Ser Asn Glu Pro Val Cys Gly Ser Asp Ala Asn Thr Tyr Ala
        115                 120                 125

Asn Leu Cys Gln Leu Arg Ala Ala Ser Arg Arg Ser Glu Arg Leu His
    130                 135                 140

Arg Pro Pro Val Ile Val Leu Gln Arg Gly Ala Cys Gly Gln Gly Gln
145                 150                 155                 160

Glu Asp Pro Asn Ser Leu Arg His Lys Tyr Asn Phe Ile Ala Asp Val
                165                 170                 175

Val Glu Lys Ile Ala Pro Ala Val Val His Ile Glu Leu Phe Arg Lys
            180                 185                 190

Leu Pro Phe Ser Lys Arg Glu Val Pro Val Ala Ser Gly Ser Gly Phe
        195                 200                 205

Ile Val Ser Glu Asp Gly Leu Ile Val Thr Asn Ala His Val Val Thr
    210                 215                 220

Asn Lys His Arg Val Lys Val Glu Leu Lys Asn Gly Ala Thr Tyr Glu
225                 230                 235                 240

Ala Lys Ile Lys Asp Val Asp Glu Lys Ala Asp Ile Ala Leu Ile Lys
                245                 250                 255
```

```
Ile Asp His Gln Gly Lys Leu Pro Val Leu Leu Gly Arg Ser Ser
        260                 265                 270

Glu Leu Arg Pro Gly Glu Phe Val Val Ala Ile Gly Ser Pro Phe Ser
    275                 280                 285

Leu Gln Asn Thr Val Thr Thr Gly Ile Val Ser Thr Thr Gln Arg Gly
    290                 295                 300

Gly Lys Glu Leu Gly Leu Arg Asn Ser Asp Met Asp Tyr Ile Gln Thr
305                 310                 315                 320

Asp Ala Ile Ile Asn Tyr Gly Asn Ser Gly Gly Pro Leu Val Asn Leu
                325                 330                 335

Asp Gly Glu Val Ile Gly Ile Asn Thr Leu Lys Val Thr Ala Gly Ile
            340                 345                 350

Ser Phe Ala Ile Pro Ser Asp Lys Ile Lys Lys Phe Leu Thr Glu Ser
        355                 360                 365

His Asp Arg Gln Ala Lys Gly Lys Ala Ile Thr Lys Lys Lys Tyr Ile
    370                 375                 380

Gly Ile Arg Met Met Ser Leu Thr Ser Ser Lys Ala Lys Glu Leu Lys
385                 390                 395                 400

Asp Arg His Arg Asp Phe Pro Asp Val Ile Ser Gly Ala Tyr Ile Ile
                405                 410                 415

Glu Val Ile Pro Asp Thr Pro Ala Glu Ala Gly Gly Leu Lys Glu Asn
            420                 425                 430

Asp Val Ile Ile Ser Ile Asn Gly Gln Ser Val Val Ser Ala Asn Asp
        435                 440                 445

Val Ser Asp Val Ile Lys Arg Glu Ser Thr Leu Asn Met Val Val Arg
    450                 455                 460

Arg Gly Asn Glu Asp Ile Met Ile Thr Val Ile Pro Glu Glu Ile Asp
465                 470                 475                 480

Pro

<210> SEQ ID NO 61
<211> LENGTH: 161
<212> TYPE: PRT
<213> ORGANISM: Homo sapiens

<400> SEQUENCE: 61

Gly Ser Gly Phe Ile Val Ser Glu Asp Gly Leu Ile Val Thr Asn Ala
1               5                   10                  15

His Val Val Thr Asn Lys His Arg Val Lys Val Glu Leu Lys Asn Gly
            20                  25                  30

Ala Thr Tyr Glu Ala Lys Ile Lys Asp Val Asp Glu Lys Ala Asp Ile
        35                  40                  45

Ala Leu Ile Lys Ile Asp His Gln Gly Lys Leu Pro Val Leu Leu Leu
    50                  55                  60

Gly Arg Ser Ser Glu Leu Arg Pro Gly Glu Phe Val Val Ala Ile Gly
65                  70                  75                  80

Ser Pro Phe Ser Leu Gln Asn Thr Val Thr Thr Gly Ile Val Ser Thr
                85                  90                  95

Thr Gln Arg Gly Gly Lys Glu Leu Gly Leu Arg Asn Ser Asp Met Asp
            100                 105                 110

Tyr Ile Gln Thr Asp Ala Ile Ile Asn Tyr Gly Asn Ser Gly Gly Pro
        115                 120                 125

Leu Val Asn Leu Asp Gly Glu Val Ile Gly Ile Asn Thr Leu Lys Val
    130                 135                 140
```

Thr Ala Gly Ile Ser Phe Ala Ile Pro Ser Asp Lys Ile Lys Lys Phe
145                 150                 155                 160

Leu

<210> SEQ ID NO 62
<211> LENGTH: 161
<212> TYPE: PRT
<213> ORGANISM: Macaca fascicularis

<400> SEQUENCE: 62

Gly Ser Gly Phe Ile Val Ser Glu Asp Gly Leu Ile Val Thr Asn Ala
1               5                   10                  15

His Val Val Thr Asn Lys His Arg Val Lys Val Glu Leu Lys Asn Gly
            20                  25                  30

Ala Thr Tyr Glu Ala Lys Ile Lys Asp Val Asp Glu Lys Ala Asp Ile
        35                  40                  45

Ala Leu Ile Lys Ile Asp His Gln Gly Lys Leu Pro Val Leu Leu Leu
    50                  55                  60

Gly Arg Ser Ser Glu Leu Arg Pro Gly Glu Phe Val Val Ala Ile Gly
65                  70                  75                  80

Ser Pro Phe Ser Leu Gln Asn Thr Val Thr Thr Gly Ile Val Ser Thr
                85                  90                  95

Thr Gln Arg Gly Gly Lys Glu Leu Gly Leu Arg Asn Ser Asp Met Asp
            100                 105                 110

Tyr Ile Gln Thr Asp Ala Ile Ile Asn Tyr Gly Asn Ser Gly Gly Pro
        115                 120                 125

Leu Val Asn Leu Asp Gly Glu Val Ile Gly Ile Asn Thr Leu Lys Val
    130                 135                 140

Thr Ala Gly Ile Ser Phe Ala Ile Pro Ser Asp Lys Ile Lys Lys Phe
145                 150                 155                 160

Leu

<210> SEQ ID NO 63
<211> LENGTH: 161
<212> TYPE: PRT
<213> ORGANISM: Oryctolagus cuniculus

<400> SEQUENCE: 63

Gly Ser Gly Phe Ile Val Ser Glu Asp Gly Leu Ile Val Thr Asn Ala
1               5                   10                  15

His Val Val Thr Asn Lys His Arg Val Lys Val Glu Leu Lys Asn Gly
            20                  25                  30

Ala Thr Tyr Glu Ala Lys Ile Lys Asp Val Asp Glu Lys Ala Asp Ile
        35                  40                  45

Ala Leu Ile Lys Ile Asp His Gln Gly Lys Leu Pro Val Leu Leu Leu
    50                  55                  60

Gly Arg Ser Ser Glu Leu Arg Pro Gly Glu Phe Val Val Ala Ile Gly
65                  70                  75                  80

Ser Pro Phe Ser Leu Gln Asn Thr Val Thr Thr Gly Ile Val Ser Thr
                85                  90                  95

Thr Gln Arg Gly Gly Lys Glu Leu Gly Leu Arg Asn Ser Asp Met Asp
            100                 105                 110

Tyr Ile Gln Thr Asp Ala Ile Ile Asn Tyr Gly Asn Ser Gly Gly Pro
        115                 120                 125

Leu Val Asn Leu Asp Gly Glu Val Ile Gly Ile Asn Thr Leu Lys Val
    130                 135                 140

Thr Ala Gly Ile Ser Phe Ala Ile Pro Ser Asp Lys Ile Lys Lys Phe
145                 150                 155                 160

Leu

<210> SEQ ID NO 64
<211> LENGTH: 161
<212> TYPE: PRT
<213> ORGANISM: Mus musculus

<400> SEQUENCE: 64

Gly Ser Gly Phe Ile Val Ser Glu Asp Gly Leu Ile Val Thr Asn Ala
1               5                   10                  15

His Val Val Thr Asn Lys Asn Arg Val Lys Val Glu Leu Lys Asn Gly
                20                  25                  30

Ala Thr Tyr Glu Ala Lys Ile Lys Asp Val Asp Glu Lys Ala Asp Ile
            35                  40                  45

Ala Leu Ile Lys Ile Asp His Gln Gly Lys Leu Pro Val Leu Leu Leu
        50                  55                  60

Gly Arg Ser Ser Glu Leu Arg Pro Gly Glu Phe Val Val Ala Ile Gly
65                  70                  75                  80

Ser Pro Phe Ser Leu Gln Asn Thr Val Thr Thr Gly Ile Val Ser Thr
                85                  90                  95

Thr Gln Arg Gly Gly Lys Glu Leu Gly Leu Arg Asn Ser Asp Met Asp
            100                 105                 110

Tyr Ile Gln Thr Asp Ala Ile Ile Asn Tyr Gly Asn Ser Gly Gly Pro
        115                 120                 125

Leu Val Asn Leu Asp Gly Glu Val Ile Gly Ile Asn Thr Leu Lys Val
    130                 135                 140

Thr Ala Gly Ile Ser Phe Ala Ile Pro Ser Asp Lys Ile Lys Lys Phe
145                 150                 155                 160

Leu

<210> SEQ ID NO 65
<211> LENGTH: 161
<212> TYPE: PRT
<213> ORGANISM: Rattus norvegicus

<400> SEQUENCE: 65

Gly Ser Gly Phe Ile Val Ser Glu Asp Gly Leu Ile Val Thr Asn Ala
1               5                   10                  15

His Val Val Thr Asn Lys Asn Arg Val Lys Val Glu Leu Lys Asn Gly
                20                  25                  30

Ala Thr Tyr Glu Ala Lys Ile Lys Asp Val Asp Glu Lys Ala Asp Ile
            35                  40                  45

Ala Leu Ile Lys Ile Asp His Gln Gly Lys Leu Pro Val Leu Leu Leu
        50                  55                  60

Gly Arg Ser Ser Glu Leu Arg Pro Gly Glu Phe Val Val Ala Ile Gly
65                  70                  75                  80

Ser Pro Phe Ser Leu Gln Asn Thr Val Thr Thr Gly Ile Val Ser Thr
                85                  90                  95

Thr Gln Arg Gly Gly Lys Glu Leu Gly Leu Arg Asn Ser Asp Met Asp
            100                 105                 110

Tyr Ile Gln Thr Asp Ala Ile Ile Asn Tyr Gly Asn Ser Gly Gly Pro
        115                 120                 125

Leu Val Asn Leu Asp Gly Glu Val Ile Gly Ile Asn Thr Leu Lys Val

```
              130                 135                 140
Thr Ala Gly Ile Ser Phe Ala Ile Pro Ser Asp Lys Ile Lys Lys Phe
145                 150                 155                 160

Leu

<210> SEQ ID NO 66
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein X at postion 1 is defined as
      N-(4-methylcoumaryl-7-amide)-isoleucine
<220> FEATURE:
<221> NAME/KEY: MISC_FEATURE
<222> LOCATION: (10)..(10)
<223> OTHER INFORMATION: wherein X at postion 10 is defined as N
      epsilon-(2,4-dinitrophenyl)-lysine

<400> SEQUENCE: 66

Xaa Arg Arg Val Ser Tyr Ser Phe Lys Xaa
1               5                   10

<210> SEQ ID NO 67
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein X at position 1 is defined as
      N-succinyl-L-Leucine
<220> FEATURE:
<221> NAME/KEY: MISC_FEATURE
<222> LOCATION: (4)..(4)
<223> OTHER INFORMATION: wherein X at position 4 is defined as
      L-Tyrosine-(4-methylcoumaryl-7 amide)

<400> SEQUENCE: 67

Xaa Leu Val Xaa
1

<210> SEQ ID NO 68
<211> LENGTH: 4
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein X at position 1 is defined as
      tert-butyloxycarbonyl-L-leucine
<220> FEATURE:
<221> NAME/KEY: MISC_FEATURE
<222> LOCATION: (4)..(4)
<223> OTHER INFORMATION: wherein X at position 4 is defined as
      L-Arginine-(4-methylcoumaryl-7 amide)

<400> SEQUENCE: 68

Xaa Ser Thr Xaa
1

<210> SEQ ID NO 69
<211> LENGTH: 7
```

```
-continued

<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: wherein X at position 1 is defined as
      7-methoxycoumarin-4-yl)acetyl-L-Lysine
<220> FEATURE:
<221> NAME/KEY: MISC_FEATURE
<222> LOCATION: (5)..(5)
<223> OTHER INFORMATION: wherein X at position 5 is defined as
      leucyl-[Nbeta-(2,4-dinitrophenyl)-L-2,3-diaminopropionyl]-L-
      Alanine
<220> FEATURE:
<221> NAME/KEY: MISC_FEATURE
<222> LOCATION: (7)..(7)
<223> OTHER INFORMATION: wherein X at position 7 is defined as
      L-Arginine-amide

<400> SEQUENCE: 69

Xaa Pro Leu Gly Xaa Ala Xaa
1               5
```

US 11,866,472 B2

PEPTIDE FOR TREATING RETINITIS PIGMENTOSA

STATEMENT REGARDING SEQUENCE LISTING

The sequence listing associated with this application is provided in text format in lieu of a paper copy and is hereby incorporated by reference into the specification. The name of the text file containing the sequence listing is 1660-P89USPNP2_Seq_List_Revised_20230215_ST25.txt. The text file is 52 KB; was created on Feb. 15, 2023, contains no new matter, and is being submitted via Patent Center.

TECHNICAL FIELD

The present invention relates to a pharmaceutical composition for the treatment or prevention of various diseases comprising a peptide, a conjugate thereof, or the like, a method for identifying peptides and the like for the treatment or prevention of various diseases, and the like.

BACKGROUND ART

High temperature requirement A serine peptidase 1 (HTRA1) is a trypsin-like serine protease (PRSS11; Clan P A, family S1) and is constituted by an N-terminal domain consisting of an IGFBP-like module and a Kazal-like module, a protease domain and a C-terminal PDZ domain. HTRA1 belongs to the HTRA family including HTRA2, HTRA3, and HTRA4 and reversibly exhibits active and inactive structures, in the same way as the other HTRA molecules (Non Patent Literature 1 and 2). Its expression is maldistributed in the human body and found at relatively high levels in the cartilage, the synovial membrane, the placenta, and the like. It is known that HTRA1 cleaves many extracellular matrix constituents such as amyloid precursor protein, fibromodulin, clusterin, ADAM9, and vitronectin as substrates and is related to diseases typified by arthritis and bone calcification (Non Patent Literature 3, 4, 5, and 6). It is further known that if a HTRA1 promoter region has a gene polymorphism (rs11200638), HTRA1 transcription level is elevated. Genome-wide association analysis has also revealed that the polymorphism correlates strongly with age-related macular degeneration (hereinafter, referred to as AMD) (Non Patent Literature 7 and 8). However, the association with retinitis pigmentosa has not been well reported.

Retinitis pigmentosa is a progressive retinal degenerative disease that begins with the degeneration and loss of rod photoreceptor cells. Due to the degeneration of photoreceptor cells, progressive night blindness, constriction of the visual field, and photophobia are observed, resulting in decreased visual acuity, and possibly blindness. Retinitis pigmentosa is known as a hereditary disease, and 3,000 or more gene mutations that cause retinitis pigmentosa have been identified to date (Non Patent Literature 9). Among these, for the gene mutations of rhodopsin alone, which represent a high proportion, 120 or more have been confirmed in humans, and 11 mechanisms leading to rod loss have been proposed depending on the classification (Non Patent Literature 10). Under such circumstances, narrowing down the target molecules for drug discovery is extremely difficult, and is considered to be a factor in making the development of therapeutic drugs for retinitis pigmentosa difficult. Therefore, the development of treatment methods that do not directly target genes is desired (Non Patent Literature 11).

There is currently no established therapeutic drug for retinitis pigmentosa. However, the following concepts have been established as potential treatments for retinitis pigmentosa from the numerous animal experiments and human clinical trials (Non Patent Literature 9). Namely:
a) Even a small improvement in rod survival leads to cone protection
b) Cone survival can be supported even with dysfunctional rods
c) If even just a few cones in the macula can be preserved, it is possible to maintain a minimum visual acuity, for example, to be able to walk well on one's own.

Based on these concepts, clinical trials have been conducted on nutritional factors such as CNTF, valproic acid, vitamin A, docosahexaenoic acid (DHA), and the like for the purpose of protecting the rods or cones. However, no clear medicinal effect has been reported so far, and no compound has been approved by the FDA.

On the other hand, what is currently being actively studied at the non-clinical and clinical stage is regenerative medicine by transplantation of stem cells or cells differentiated into rods. However, there are many problems that need to be solved, such as immune rejection, low survival rate of transplanted cells, retention rate, and biosafety (Non Patent Literature 12).

CITATION LIST

Non Patent Literature

Non Patent Literature 1: Truebestein L, et al., 2011, Nat Struct Mol Biol., Vol. 18 (No. 3): p. 386-8
Non Patent Literature 2: Eigenbrot C, et al., 2012, Structure, Vol. 20 (No. 6): p. 1040-50
Non Patent Literature 3: Grau S, et al., 2005, Proc Natl Acad Sci USA., Vol. 102 (No. 17): p. 6021-26
Non Patent Literature 4: Grau S, et al., 2006, J Biol Chem., Vol. 281 (No. 10): p. 6124-29
Non Patent Literature 5: Hadfield K D, et al., 2008, J Biol Chem., Vol. 283, (No. 9): p. 5928-38
Non Patent Literature 6: An E, et al., 2010, Invest Ophthalmol Vis Sci., Vol. 51 (No. 7): p. 3379-86
Non Patent Literature 7: Yang Z, et al., 2006, Science, Vol. 314 (No. 5801): p. 992-93
Non Patent Literature 8: Tang N P, et al., 2009, Ann Epidemiol., Vol. 19 (No. 10): p. 740-45
Non Patent Literature 9: Guadagni V, et al., 2015, Prog Retin Eye Res., Vol. 48: p. 62-81
Non Patent Literature 10: Memdes H F et al., 2005, TRENDS Mol. Medicine, Vol. 11: p. 177-185
Non Patent Literature 11: Farrar G J, et al., 2002, EMBO J., Vol. 21 (No. 5): p. 857-864
Non Patent Literature 12: He Y, et al., 2014, Int. J. Mol. Sci., Vol. 15 (No. 8): p. 14456-14474

SUMMARY OF INVENTION

Technical Problem

To provide a novel pharmaceutical composition for the treatment or prevention of retinitis pigmentosa.

Solution to Problem

The present invention relates to:
(1) A pharmaceutical composition for the treatment or prevention of retinitis pigmentosa, hereditary diseases involving photoreceptor cell degeneration, and/or diseases associated with PDE6 protein dysfunction, comprising a SPINK2 mutant peptide which comprises the amino acid sequence shown in SEQ ID NO: 30 (FIG. 42) and which inhibits the protease activity of human HTRA1;

(2)

The pharmaceutical composition according to (1), wherein the first Xaa ($X_1$) is Asp, Glu, Ser, Gly, or Ile, the second Xaa ($X_2$) is Ala, Gly, Leu, Ser or Thr, the third Xaa ($X_3$) is Asp, His, Lys, Met or Gln, the fourth Xaa ($X_4$) is Asp, Phe, His, Ser or Tyr, the fifth Xaa ($X_5$) is Ala, Asp, Glu, Met or Asn, the sixth Xaa ($X_6$) is Met or Trp, the seventh Xaa ($X_7$) is Gln, Trp, Tyr or Val, the eighth Xaa ($X_8$) is Phe, Leu or Tyr, the ninth Xaa ($X_9$) is Phe or Tyr, the tenth Xaa ($X_{10}$) is Ala, Glu, Met or Val, and the eleventh Xaa ($X_{11}$) is Ala, Thr or Val in the amino acid sequence shown in SEQ ID NO: 30 (FIG. 42) comprised in the peptide;

(3)

The pharmaceutical composition according to (1) or (2), wherein the peptide comprises an amino acid sequence shown in any one of SEQ ID NOs: 3, 5, 7, 9, 11, 13, 15, 17, 19, 21 and 23 to 29 (FIGS. 15, 17, 19, 21, 23, 25, 27, 29, 31, 33 and 35 to 41);

(4) The pharmaceutical composition according to any one of (1) to (3), wherein the peptide comprises an amino acid sequence prepared by the addition via a peptide bond of one to three amino acids at the amino-terminal side of the amino acid sequence shown in SEQ ID NO: 30 (FIG. 42);

(5)

The pharmaceutical composition according to any one of (1) to (4), wherein the peptide comprises an amino acid sequence prepared by the addition via a peptide bond of one or two amino acids at the carboxyl-terminal side of the amino acid sequence shown in SEQ ID NO: 30 (FIG. 42);

(6)

The pharmaceutical composition according to any one of (1) to (5), wherein the peptide has a three-dimensional structure characterized by having three disulfide bonds and comprising a loop structure, an α helix and a β sheet;

(7)

A pharmaceutical composition for the treatment or prevention of retinitis pigmentosa, hereditary diseases involving photoreceptor cell degeneration, and/or diseases associated with PDE6 protein dysfunction, comprising a polynucleotide comprising a nucleotide sequence encoding an amino acid sequence comprised in the peptide according to any one of (1) to (6);

(8)

A pharmaceutical composition for the treatment or prevention of retinitis pigmentosa, hereditary diseases involving photoreceptor cell degeneration, and/or diseases associated with PDE6 protein dysfunction, comprising a vector comprising a nucleotide sequence encoding an amino acid sequence comprised in the peptide according to any one of (1) to (6);

(9)

A pharmaceutical composition for the treatment or prevention of retinitis pigmentosa, hereditary diseases involving photoreceptor cell degeneration, and/or diseases associated with PDE6 protein dysfunction, comprising a cell comprising a polynucleotide comprising a nucleotide sequence encoding an amino acid sequence comprised in the peptide according to any one of (1) to (6), or a vector comprising the nucleotide sequence, or a cell producing the peptide according to any one of (1) to (6);

(10)

A pharmaceutical composition for the treatment or prevention of retinitis pigmentosa, hereditary diseases involving photoreceptor cell degeneration, and/or diseases associated with PDE6 protein dysfunction, comprising a conjugate comprising the peptide according to any one of (1) to (6) linked to an additional moiety;

(11)

The pharmaceutical composition according to (10), wherein the conjugate is a polypeptide;

(12)

The pharmaceutical composition according to any one of (1) to (11), which is for the treatment or prevention of retinitis pigmentosa;

(13)

The pharmaceutical composition according to any one of (1) to (11), which is for the treatment or prevention of hereditary diseases involving photoreceptor cell degeneration;

(14)

The pharmaceutical composition according to (13), wherein the hereditary disease involving photoreceptor cell degeneration is macular dystrophy;

(15)

The pharmaceutical composition according to any one of (1) to (11), which is for the treatment or prevention of diseases associated with PDE6 protein dysfunction;

(16)

The pharmaceutical composition according to (15), wherein the disease associated with PDE6 protein dysfunction is achromatopsia or autosomal dominant congenital stationary night blindness;

(17)

The pharmaceutical composition according to any one of (1) to (16), which comprises one or two or more additional medicaments;

(18)

The pharmaceutical composition according to any one of (1) to (17), which is used in combination with one or two or more additional medicaments; and (19)

A method for identifying a therapeutic drug or a prophylactic drug for retinitis pigmentosa, hereditary diseases involving photoreceptor cell degeneration, and/or diseases associated with PDE6 protein dysfunction, comprising the following steps 1 to 3:

[step 1] incubating a HTRA1 protease and a substrate in the presence and absence of a test substance, which is a SPINK2 mutant peptide comprising the amino acid sequence shown in SEQ ID NO: 30 (FIG. 42);

[step 2] detecting HTRA1 protease activity in the presence and absence of the test substance; and

[step 3] determining the test substance to be positive when the HTRA1 protease activity in the presence of the test substance is lower than the HTRA1 protease activity in the absence of the test substance.

Advantageous Effects of Invention

The peptide provided by the present invention, and a pharmaceutical composition comprising the same have HTRA1 inhibitory activity and are useful in the treatment or prevention, etc. of retinitis pigmentosa.

BRIEF DESCRIPTION OF DRAWINGS

FIG. 1(A) is a diagram showing the results of comparing sequence similarity among human (SEQ ID NO:57), mouse (SEQ ID NO:58), rat (SEQ ID NO:59), and monkey (SEQ ID NO:60) HTRA1. The broken line depicts an enzymatically active domain (204Gly to 364Leu).

FIG. 1(B) is a diagram showing results of comparing sequence similarity among human (SEQ ID NO:57), mouse (SEQ ID NO:58), rat (SEQ ID NO:59), and monkey (SEQ ID NO:60) HTRA1 (Cont.).

FIG. 2 is a diagram showing the results of evaluating the HTRA1 (cat) inhibitory activity of a HTRA1-inhibiting peptide by using the decomposition rate of a peptide substrate as an indicator. Panels A to C each show the evaluation results for each inhibiting peptide, and panel D shows the evaluation results for control wild-type SPINK2.

FIG. 3 is a diagram showing the results of evaluating the HTRA1 (full) inhibitory activity of a HTRA1-inhibiting peptide by using the decomposition rate of a peptide substrate as an indicator (panels A to C).

FIG. 8 shows the amino acid sequence (SEQ ID NO: 54) of H2-Opt. N-terminal "Mca-I" means N-(4-methylcoumaryl-7-amide)-isoleucine, and C-terminal "(Dnp)K" means N epsilon-(2,4-dinitrophenyl)-lysine.

FIG. 13 shows the amino acid sequence (SEQ ID NO: 1) of human SPINK2.

FIG. 14 shows a nucleotide sequence (SEQ ID NO: 2) encoding the amino acid sequence of human SPINK2.

FIG. 15 shows the amino acid sequence (SEQ ID NO: 3) of peptide H218.

FIG. 16 shows a nucleotide sequence (SEQ ID NO: 4) encoding the amino acid sequence of peptide H218.

FIG. 17 shows the amino acid sequence (SEQ ID NO: 5) of peptide H223.

FIG. 18 shows a nucleotide sequence (SEQ ID NO: 6) encoding the amino acid sequence of peptide H223.

FIG. 19 shows the amino acid sequence (SEQ ID NO: 7) of peptide H228.

FIG. 20 shows a nucleotide sequence (SEQ ID NO: 8) encoding the amino acid sequence of peptide H228.

FIG. 21 shows the amino acid sequence (SEQ ID NO: 9) of peptide H308.

FIG. 22 shows a nucleotide sequence (SEQ ID NO: 10) encoding the amino acid sequence of peptide H308.

FIG. 23 shows the amino acid sequence (SEQ ID NO: 11) of peptide H321.

FIG. 24 shows a nucleotide sequence (SEQ ID NO: 12) encoding the amino acid sequence of peptide H321.

FIG. 25 shows the amino acid sequence (SEQ ID NO: 13) of peptide H322.

FIG. 26 shows a nucleotide sequence (SEQ ID NO: 14) encoding the amino acid sequence of peptide H322.

FIG. 27 shows the amino acid sequence (SEQ ID NO: 15) of peptide derivative H308AT.

FIG. 28 shows a nucleotide sequence (SEQ ID NO: 16) encoding the amino acid sequence of peptide derivative H308AT.

FIG. 29 shows the amino acid sequence (SEQ ID NO: 17) of peptide derivative H321AT.

FIG. 30 shows a nucleotide sequence (SEQ ID NO: 18) encoding the amino acid sequence of peptide derivative H321AT.

FIG. 31 shows the amino acid sequence (SEQ ID NO: 19) of peptide derivative H322AT.

FIG. 32 shows a nucleotide sequence (SEQ ID NO: 20) encoding the amino acid sequence of peptide derivative H322AT.

FIG. 33 shows the amino acid sequence (SEQ ID NO: 21) of peptide M7.

FIG. 34 shows a nucleotide sequence (SEQ ID NO: 22) encoding the amino acid sequence of peptide M7.

FIG. 35 shows the amino acid sequence (SEQ ID NO: 23) of peptide derivative H308_S16A.

FIG. 36 shows the amino acid sequence (SEQ ID NO: 24) of peptide derivative H308_D1G_S16A.

FIG. 37 shows the amino acid sequence (SEQ ID NO: 25) of peptide derivative H308_D1S_S16A.

FIG. 38 shows the amino acid sequence (SEQ ID NO: 26) of peptide derivative H308_D1E_S16A.

FIG. 39 shows the amino acid sequence (SEQ ID NO: 27) of peptide derivative H308_D1SLI_S16A.

FIG. 40 shows the amino acid sequence (SEQ ID NO: 28) of peptide derivative H321AT_D1G_S16A.

FIG. 41 shows the amino acid sequence (SEQ ID NO: 29) of peptide derivative H322AT_D1G_S16A.

FIG. 42 shows the general formula (SEQ ID NO: 30) of a HTRA1-inhibiting peptide. $X_1$ to $X_{11}$ each represent an arbitrary amino acid.

FIG. 43 shows an amino acid sequence (SEQ ID NO: 31) consisting of S tag and a linker.

FIG. 44 shows the amino acid sequence (SEQ ID NO: 32) of a C-terminal hexamer.

FIG. 45 shows the nucleotide sequence (SEQ ID NO: 33) of primer 1.

FIG. 46 shows the nucleotide sequence (SEQ ID NO: 34) of primer 2.

FIG. 47 shows the nucleotide sequence (SEQ ID NO: 35) of primer 3.

FIG. 48 shows the nucleotide sequence (SEQ ID NO: 36) of primer 4.

FIG. 49 shows the nucleotide sequence (SEQ ID NO: 37) of primer 5.

FIG. 50 shows the nucleotide sequence (SEQ ID NO: 38) of primer 6.

FIG. 51 shows the nucleotide sequence (SEQ ID NO: 39) of primer 7.

FIG. 52 shows the nucleotide sequence (SEQ ID NO: 40) of primer 8.

FIG. 53 shows the nucleotide sequence (SEQ ID NO: 41) of primer 9.

FIG. 54 shows the nucleotide sequence (SEQ ID NO: 42) of primer 10.

FIG. 55 shows the nucleotide sequence (SEQ ID NO: 43) of primer 11.

FIG. 56 shows the nucleotide sequence (SEQ ID NO: 44) of primer 12.

FIG. 57 shows the nucleotide sequence (SEQ ID NO: 45) of primer 13.

FIG. 58 shows the nucleotide sequence (SEQ ID NO: 46) of primer 14.

FIG. 59 shows the nucleotide sequence (SEQ ID NO: 47) of primer 15.

FIG. 60 shows the nucleotide sequence (SEQ ID NO: 48) of primer 16.

FIG. 61 shows the nucleotide sequence (SEQ ID NO: 49) of primer 17.

FIG. 62 shows the nucleotide sequence (SEQ ID NO: 50) of primer 18.

FIG. 63 shows the nucleotide sequence (SEQ ID NO: 51) of primer 19.

FIG. 64 shows the nucleotide sequence (SEQ ID NO: 52) of primer 20.

FIG. 65 shows the amino acid sequence (SEQ ID NO: 53) of human HTRA1 (full).

FIG. 72(A) is a diagram showing that a HTRA1-inhibiting peptide H308 administration group of HFD-HQ-loaded 3-year-old rabbits exhibited a suppressive effect on the hypertrophy of RPE cells. n=5 for all groups. An average area was used as an indicator.

FIG. 72(B) is a diagram showing that a HTRA1-inhibiting peptide H308 administration group of HFD-HQ-loaded 3-year-old rabbits exhibited a suppressive effect on the hypertrophy of RPE cells. n=5 for all groups. The number of RPE cells having a cell area of 1500 μm² or larger was used as an indicator.

FIG. 73 is a diagram showing the results of comparing sequence similarity between the enzymatically active domain of human (SEQ ID NO:61), monkey (SEQ ID NO:62), rabbit (SEQ ID NO:63), mouse (SEQ ID NO:64), and rat (SEQ ID NO:65) HTRA1.

FIG. 76 shows the nucleotide sequence of primer 21.

FIG. 77 shows the nucleotide sequence of primer 22.

Figure 4A:
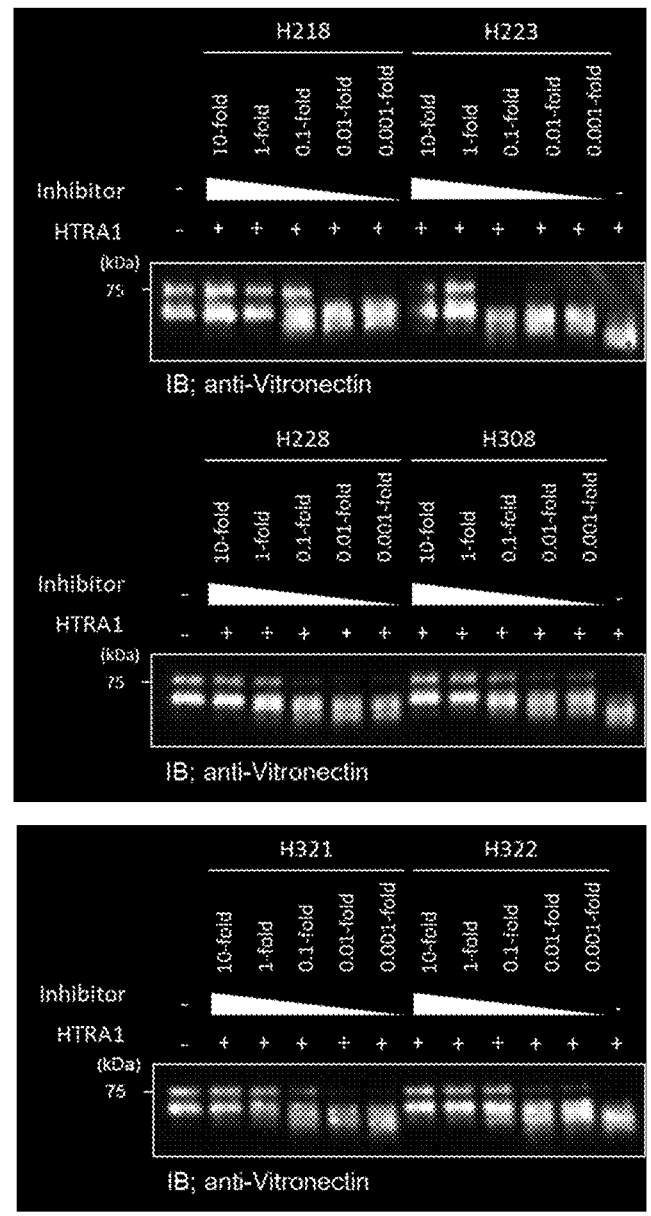
FIG. 4(A) is a diagram showing the results of evaluating the HTRA1 (cat) inhibitory activity of a HTRA1-inhibiting peptide by using the decomposition of human vitronectin as an indicator. Analysis was conducted by Western blot using Human Vitronectin Antibody (R&D Systems, Inc.; MAB2349).

In the present invention, the phrase "SEQ ID NO: X (Figure Y)" or "Figure Y (SEQ ID NO: X)" means that the sequence is shown in SEQ ID NO: X or shown in Figure Y.

DESCRIPTION OF EMBODIMENTS

1. Definition

In the present invention, the term "gene" is used to mean a nucleic acid molecule comprising a nucleotide sequence encoding an amino acid sequence contained in a protein, or a complementary strand thereof. The gene consists of a single strand, a double strand or a triple or more strand. An association of a DNA strand and an RNA strand, ribonucleotides and deoxyribonucleotides coexisting on one strand, and a double-stranded or triple- or more stranded nucleic acid molecule including such a strand are also included within the meaning of the term "gene".

In the present invention, the terms "gene", "polynucleotide" and "nucleic acid molecule" are synonymous with each other and are not limited by the number of their constituent units such as ribonucleotides, deoxyribonucleotides, nucleotides, and nucleosides by any means. For example, DNA, RNA, mRNA, cDNA, cRNA, a probe, an oligonucleotide, a primer, and the like are also included within the scope thereof. The term "nucleic acid molecule" is also abbreviated to a "nucleic acid".

In the present invention, the terms "polypeptide", "peptide" and "protein" are synonymous with each other. A peptide that inhibits or suppresses one or two or more activities or functions of target molecule X (hereinafter, these inhibitory or suppressive effects are collectively referred to as "X inhibitory activity") can be referred to as an "X-inhibiting peptide".

The term "SPINK2" is used to mean serine protease inhibitor Kazal-type 2. This protein of 7 kDa consists of a Kazal-like domain having three disulfide bonds. SPINK2 is preferably human-derived. In the present invention, human SPINK2 is simply referred to as "SPINK2", unless otherwise specified.

The term "HTRA1" is used to mean high temperature requirement A serine peptidase 1. This protein is constituted by an N-terminal domain consisting of an IGFBP-like module and a Kazal-like module, a protease domain and a C-terminal PDZ domain and belongs to the HTRA family. HTRA1 is preferably human-derived. In the present invention, human HTRA1 is also simply referred to as "HTRA1", unless otherwise specified.

The term "HTRA1-inhibiting peptide" is used to mean a peptide that inhibits or suppresses one or two or more activities or functions of HTRA1. A fragment of the peptide, an adduct of the peptide with an additional moiety, or a conjugate of the peptide that maintains HTRA1 inhibitory activity is included within the scope of the term "HTRA1-inhibiting peptide". Specifically, a fragment, an adduct and a modified form of the peptide that maintain HTRA1 inhibitory activity are also included within the term "HTRA1-inhibiting peptide".

In the present invention, the term "cell" is used to include various cells derived from animal individuals, subcultured cells, primary cultured cells, cell lines, recombinant cells, yeasts, microbes and the like.

In the present invention, the term "site" to which a peptide binds, i.e., the "site" that is recognized by a peptide is used to mean a consecutive or intermittent partial amino acid sequence or partial conformation on a target molecule to be bound or recognized by a peptide. In the present invention, such a site can be referred to as an epitope or a binding site on the target molecule.

The term "SPINK2 mutant" is used to mean a peptide comprising an amino acid sequence derived from the amino acid sequence of wild-type SPINK2 by the substitution of one or two or more amino acids with amino acids different from the wild-type ones, the deletion of one or two or more wild-type amino acids, the insertion of one or two or more amino acids absent in the wild-type, and/or the addition of amino acid(s) absent in the wild-type to the amino terminus (N terminus) and/or carboxyl terminus (C terminus) of the wild-type (hereinafter, collectively referred to as a "mutation"). A "SPINK2 mutant" having HTRA1 inhibitory activity is included in the HTRA1-inhibiting peptide. In the present invention, the "insertion" can also be included in the "addition".

In the present invention, the term "several" in the phrase "one or several" refers to 3 to 10.

In the present invention, the phrase "to hybridize under stringent conditions" is used to mean that hybridization is carried out under conditions in which hybridization is carried out at 65° C. in a solution containing 5×SSC, and the resultant is then washed at 65° C. for 20 minutes in an aqueous solution containing 2×SSC and 0.1% SDS, at 65° C. for 20 minutes in an aqueous solution containing 0.5×SSC and 0.1% SDS, and at 65° C. for 20 minutes in an aqueous solution containing 0.2×SSC and 0.1% SDS, or conditions equivalent thereto. SSC means an aqueous solution of 150 mM NaCl and 15 mM sodium citrate, and "n X SSC" means an n-fold concentration of SSC.

In the present invention, the terms "specific" and "specificity" are synonymous and interchangeable with the terms "selective" and "selectivity", respectively. For example, a HTRA1-specific inhibiting peptide is synonymous with a HTRA1-selective inhibiting peptide.

2. Peptide

2-1. Amino acid

The term "amino acid" is used to mean an organic compound containing an amino group and a carboxyl group and to mean an α-amino acid contained as a constituent unit preferably in a protein, and more preferably in a natural protein. In the present invention, the amino acid is more preferably Ala, Arg, Asn, Asp, Cys, Gln, Glu, Gly, His, Ile, Leu, Lys, Met, Phe, Pro, Ser, Thr, Trp, Tyr and Val. The term "amino acid" is used to mean these 20 amino acids in total, unless otherwise specified. These 20 amino acids in total can be referred to as "natural amino acids". The HTRA1-inhibiting peptide of the present invention preferably contains natural amino acids.

In the present invention, the term "amino acid residue" is also referred to as an "amino acid".

In the present invention, the amino acid may be an L-amino acid, a D-amino acid, or a mixture thereof (DL-amino acid) and means an L-amino acid, unless otherwise specified.

Natural amino acids can be divided into, for example, the following groups, on the basis of the common properties of side chains:

(1) hydrophobic amino acid group: Met, Ala, Val, Leu, and Ile;
(2) neutral hydrophilic amino acid group: Cys, Ser, Thr, Asn, and Gln;
(3) acidic amino acid group: Asp and Glu;
(4) basic amino acid group: His, Lys, and Arg;
(5) group of amino acids influencing the direction of the main chain: Gly and Pro; and
(6) aromatic amino acid group: Trp, Tyr, and Phe.

However, the classification of natural amino acids is not limited thereto.

In the present invention, each natural amino acid may receive a conservative amino acid substitution.

The term "conservative amino acid substitution" means a substitution by a functionally equivalent or similar amino acid. A conservative amino acid substitution in a peptide brings about static change in the amino acid sequence of the peptide. For example, one or two or more amino acids substitutions having similar polarity act functionally equivalently and bring about static change in the amino acid sequence of the peptide. In general, a substitution within a certain group can be regarded as being conservative in terms of structures and functions. However, as is obvious to a person skilled in the art, the role of a specific amino acid residue can be determined by its position in the three-dimensional structure of a molecule containing the amino acid. For example, a cysteine residue can take an oxidized (disulfide) form having lower polarity than that of a reduced (thiol) form. The long aliphatic moiety of an arginine side chain is capable of constituting structurally and functionally important features. Alternatively, a side chain containing an aromatic ring (tryptophan, tyrosine, and phenylalanine) is capable of contributing to ion-aromatic interactions or cation-pi interactions. In such a case, even the substitution of amino acids having these side chains with amino acids belonging to an acidic or nonpolar group can be structurally and functionally conservative. Residues such as proline, glycine, and cysteine (disulfide form) might have a direct effect on the three-dimensional structure of the main chain and cannot often be substituted without structural distortion.

The conservative amino acid substitution includes, as shown below, a specific substitution based on side chain similarity (L. Lehninger, Biochemistry, 2nd edition, pp. 73-75, Worth Publisher, New York (1975)) and a typical substitution.

(1) Nonpolar amino acid group: alanine (hereinafter, referred to as "Ala" or simply "A"), valine (hereinafter, referred to as "Val" or simply "V"), leucine (hereinafter, referred to as "Leu" or simply "L"), isoleucine (hereinafter, referred to as "Ile" or simply "I"), proline (hereinafter, referred to as "Pro" or simply "P"), phenylalanine (hereinafter, referred to as "Phe" or simply "F"), tryptophan (hereinafter, referred to as "Trp" or simply "W"), and methionine (hereinafter, referred to as "Met" or simply "M")

(2) Uncharged polar amino acid group: glycine (hereinafter, referred to as "Gly" or simply "G"), serine (hereinafter, referred to as "Ser" or simply "S"), threonine (hereinafter, referred to as "Thr" or simply "T"), cysteine (hereinafter, referred to as "Cys" or simply "C"), tyrosine (hereinafter, referred to as "Tyr" or simply "Y"), asparagine (hereinafter, referred to as "Asn" or simply "N"), and glutamine (hereinafter, referred to as "Gln" or simply "Q")

(3) Acidic amino acid group: aspartic acid (hereinafter, referred to as "Asp" or simply "D") and glutamic acid (hereinafter, referred to as "Glu" or simply "E")

(4) Basic amino acid group: lysine (hereinafter, referred to as "Lys" or simply "K"), arginine (hereinafter, referred to as "Arg" or simply "R"), and histidine (hereinafter, referred to as "His" or simply "H")

In the present invention, amino acids may be amino acids other than the natural amino acids. Examples thereof can include selenocysteine, N-formylmethionine, pyrrolysine, pyroglutamic acid, cystine, hydroxyproline, hydroxylysine, thyroxine, 0-phosphoserine, desmosine, 0-alanine, sarcosine, ornithine, creatine, 7-aminobutyric acid, opine, theanine, tricholomic acid, kainic acid, domoic acid, and acromelic acid, which are found in natural peptides or proteins, and can include: N-terminally protected amino acids such as norleucine, Ac-amino acid, Boc-amino acid, Fmoc-amino acid, Trt-amino acid, and Z-amino acid; C-terminally protected amino acids such as t-butyl ester, benzyl ester, cyclohexyl ester, and fluorenyl ester of amino acids; and other amino acids that are not found in the natural world, including diamine, ω amino acid, β amino acid, γ amino acid, Tic derivatives of amino acids, and aminophosphonic acid. The amino acids other than the 20 "natural amino acids" are not limited thereto and are collectively referred to as "non-natural amino acids" in the present invention for the sake of convenience.

2-2. HTRA1-Inhibiting Peptide

The HTRA1-inhibiting peptide of the present invention is a SPINK2 mutant that at least partially maintains the framework of SPINK2 (hereinafter, referred to as a "SPINK2 mutant") and inhibits or suppresses the protease activity of HTRA1 or a fragment that retains its enzyme activity (hereinafter, referred to as a "functional fragment") (hereinafter, such inhibition and suppression are collectively referred to as "HTRA1 inhibitory activity").

HTRA1, which is a target of the inhibiting peptide of the present invention, is preferably mammalian HTRA1, more preferably primate HTRA1, and still more preferably human HTRA1. The amino acid sequence of full-length mature human HTRA1 (hereinafter, referred to as "HTRA1 (full)") has the amino acid sequence shown in SEQ ID NO: 53 (FIG. 65). This amino acid sequence consists of positions 23 to 480 and is free of the signal sequence consisting of positions 1 to 22. The amino acid sequence of the functional fragment of human HTRA1 (hereinafter, referred to as "HTRA1 (cat)") is not particularly limited as long as the functional fragment retains the protease activity. Examples thereof can include a functional fragment consisting of 136Gly to 351Lys of SEQ ID NO: 53 (FIG. 65), and a functional fragment comprising 136Gly to 351Lys thereof. HTRA1 or the functional fragment thereof which is a target of the inhibiting peptide of the present invention is also referred to as HTRA1 protease. The HTRA1 protease is preferably vertebrate-derived, more preferably mammal-derived, still more preferably primate-derived, and most preferably human-derived, and can be prepared by purification from the tissues or cells of any of these animals, or by a method known to a person skilled in the art as a protein preparation method such as gene recombination, in vitro translation, or peptide synthesis. HTRA1 or the functional fragment thereof may be linked to a signal sequence, an immunoglobulin Fc region, a tag, a label, or the like.

HTRA1 inhibitory activity can be evaluated by using the protease activity of HTRA1 as an indicator. For example, HTRA1 or the functional fragment thereof, a substrate and the inhibiting peptide of the present invention or a candidate thereof are allowed to coexist with each other. In this case, when the protease activity of HTRA1 is 70% or less, 50% or less, 30% or less, 20% or less, 10% or less, 5% or less, 1% or less or 0% as compared with that in the presence of a control or in the absence of the inhibitor or the candidate thereof, the inhibition of HTRA1 occurs with inhibitory activity of 30% or more, 50% or more, 70% or more, 80% or more, 90% or more, 95% or more, 99% or more or 100%, respectively. The HTRA1 inhibitory activity can differ depending on reaction conditions, the type of substrate, concentration, etc. Examples of the reaction conditions can include, but are not limited to, those described in the Examples. The enzyme activity can be evaluated by adding a substrate peptide or a substrate protein to a given concentration of HTRA1, and reacting the mixture for a given time, followed by detection of the fluorescence of the substrate peptide, or detection of the substrate protein by SDS-PAGE, Western blot, liquid chromatography, or the like. For example, phosphate buffered saline (hereinafter, referred to as "PBS"), a borate buffer (50 mM borate, pH 7 to 9, for example, pH 8.5), or a Tris buffer (50 mM Tris, pH 6 to 9, for example, pH 8.0) can be used as a buffer solution. NaCl (50 to 300 mM, for example, 150 mM) or a surfactant such as CHAPS, or octyl β-D-glucopyranoside may be added to the reaction system, though the additive is not limited thereto.

Examples of the substrate of the HTRA1 protease include, but are not particularly limited to, endogenous substrates, exogenous substrates, and synthetic substrates. Examples of the human endogenous substrate can include vitronectin. Examples of the synthetic substrate can include, but are not particularly limited to, H2-Opt (Mca-IRRVSYSFK(Dnp)K) (SEQ ID NO:66), β-casein, and other HTRA1 substrates. The HTRA1 inhibitory activity ($IC_{50}$ or $K_i$) of the peptide of the present invention is 1 μM or lower, more preferably 100 nM or lower.

It is preferred that the inhibiting peptide of the present invention should not inhibit or suppress the activity of a protease other than HTRA1, or should have a relatively weak degree of inhibition or suppression of such activity. In other words, the inhibiting peptide of the present invention preferably has high HTRA1 specificity. Preferably, the inhibiting peptide of the present invention does not inhibit or suppress the activities of proteases such as trypsin, α-chymotrypsin, tryptase, plasmin, thrombin, matriptase, protein C, tissue plasminogen activator (tPA), urokinase (uPA), plasmin, and plasma kallikrein, or has a relatively weak degree of inhibition or suppression of such activities. Such a preferred peptide of the present invention does not exhibit an adverse reaction caused by the inhibition or suppression of the activities of other proteases and can preferably be used as a therapeutic drug or a prophylactic drug for a HTRA1-related disease (mentioned later).

As mentioned above, HTRA1 which is a target of the peptide of the present invention is preferably vertebrate-derived, more preferably mammal-derived, still more preferably primate-derived, and most preferably human-derived. Alternatively, HTRA1 which is a target of the peptide of the present invention may be derived from a nonhuman animal, for example, a rodent such as a rat or a mouse, or a primate such as a cynomolgus monkey, a common marmoset, or a rhesus monkey. A peptide having inhibitory activity against nonhuman animal-derived HTRA1 can be used in the diagnosis, examination, treatment or prevention, etc. of a HTRA1-related disease in the nonhuman animal. When such a peptide also inhibits human HTRA1, the nonhuman animal can be used: in the nonclinical research and development of the peptide as a therapeutic drug or a prophylactic drug for a human HTRA1-related disease; or to conduct a pharmacological test or a pharmacokinetic test using the nonhuman animal as an animal model of the disease; or to conduct a safety test, a toxicity test, or the like using the nonhuman animal as a healthy animal.

The HTRA1-inhibiting peptide of the present invention has advantages such as: a smaller molecular weight than that of other biomolecules such as antibodies for use as medicaments and diagnostic drugs in the art; relatively easy production (mentioned later) thereof; excellent physical properties in terms of tissue penetration, storage stability, thermal stability, and the like; and a wide range of choice for administration route, administration method, preparation, and the like for use as a pharmaceutical composition (mentioned later). The half-life in blood of the peptide of the present invention used as a pharmaceutical composition can be adjusted to be longer by applying a known method such as the addition of a biomolecule or a polymer and thereby increasing the molecular weight of the peptide. The molecular weight of such a HTRA1-inhibiting peptide of the present invention is smaller than 10,000, preferably smaller than 8,000, and more preferably about 7,000 to 7,200. A variable loop moiety consisting of 15Cys to 31Cys of SEQ ID NO: 23 (FIG. 35) or a moiety consisting of 15Cys to 63Cys thereof (hereinafter, referred to as a "moiety containing six Cys residues") and having HTRA1 inhibitory activity is also included within the HTRA1-inhibiting peptide of the present invention. The molecular weight of the variable loop moiety is smaller than 2,500, and preferably about 1,800 to 2,000. The molecular weight of the moiety containing six Cys residues is smaller than 6,000, and preferably about 5,300 to 5,500.

The SPINK2 mutant that at least partially maintains the framework of SPINK2 (hereinafter, referred to as the "SPINK2 mutant"), included within the scope of the HTRA1-inhibiting peptide of the present invention, may bind to HTRA1 and is capable of binding to preferably mammalian HTRA1, more preferably primate HTRA1, and still more preferably human HTRA1. Such a peptide, which binds to HTRA1, recognizes or binds to a partial peptide, a partial conformation, or the like of HTRA1 (hereinafter, such recognizing and binding effects are collectively referred to as "target binding activity").

In an aspect, the inhibiting peptide of the present invention is capable of binding to an immunogenic fragment of HTRA1. The immunogenic fragment of HTRA1 has one or two or more epitopes, mimotopes or other antigenic determinants and is therefore capable of inducing an immune response or is capable of causing an antibody against the fragment to be produced.

The binding of the SPINK2 mutant according to the present invention to HTRA1 or to the immunogenic fragment thereof can be evaluated, measured or determined by use of a method known to a person skilled in the art, such as the measurement of detectable binding affinity (ELISA, surface plasmon resonance (hereinafter, referred to as "SPR") analysis (also referred to as a "BIAcore" method), isothermal titration calorimetry (hereinafter, referred to as "ITC"), flow cytometry, an immunoprecipitation method, etc.).

Examples of the ELISA include a method which involves detecting a HTRA1-inhibiting peptide that has recognized and bound to HTRA1 immobilized on a plate. The immobilization of HTRA1 can employ biotin-streptavidin as well as, for example, an antibody for immobilization that recognizes a tag fused with HTRA1. The detection of the HTRA1-inhibiting peptide can employ labeled streptavidin as well as, for example, a labeled antibody for detection that recognizes a tag fused with the HTRA1-inhibiting peptide. The labeling can employ biotin as well as a method feasible in biochemical analysis, such as HRP, alkaline phosphatase, or FITC. The detection using enzymatic labeling can employ a chromogenic substrate such as TMB (3,3',5,5'-tetramethylbenzidine), BCIP (5-bromo-4-chloro-3-indolyl phosphate), p-NPP (p-nitrophenyl phosphate), OPD (o-phenylenediamine), ABTS (3-ethylbenzothiazoline-6-sulfonic acid), or SuperSignal ELISA Pico Chemiluminescent Substrate (Thermo Fisher Scientific Inc.), a fluorescent substrate such as QuantaBlu™ Fluorogenic Peroxidase Substrate (Thermo Fisher Scientific Inc.), and a chemiluminescent substrate. The measurement of a detection signal can employ an absorbance plate reader, a fluorescence plate reader, a luminescence plate reader, a RI liquid scintillation counter, or the like.

Examples of an instrument for use in the SPR analysis can include BIAcore™ (GE Healthcare), ProteOn™ (Bio-Rad Laboratories, Inc.), SPR-Navi™ (Oy BioNavis Ltd.), Spreeta™ (Texas Instruments Inc.), SPRi-PlexII™ (HORIBA, Ltd.), and Autolab SPR™ (Metrohm AG). Examples of an instrument for use in BLI can include Octet™ (Pall Corp.).

Examples of the immunoprecipitation method include a method which involves detecting HTRA1 that has recognized and bound to a HTRA1-inhibiting peptide immobilized on beads. Magnetic beads, agarose beads, or the like can be used as the beads. The immobilization of the HTRA1-inhibiting peptide can employ biotin-streptavidin as well as an antibody that recognizes the peptide or a tag fused with the peptide, protein A or protein G, etc. The beads are separated using a magnet, centrifugation, or the like, and HTRA1 precipitated with the beads is detected by SDS-PAGE or Western blot. The detection of HTRA1 can employ labeled streptavidin as well as, for example, a labeled antibody for detection that recognizes a tag fused with HTRA1. The labeling can employ biotin as well as a method feasible in biochemical analysis, such as HRP, alkaline phosphatase, or FITC. The detection using enzymatic labeling can employ the same substrate as in ELISA. The measurement of a detection signal can employ ChemiDoc™ (Bio-Rad Laboratories, Inc.), LuminoGraph (ATTO Corp.), or the like.

In the present invention, the term "specific recognition", i.e., "specific binding", is used to mean binding that is not nonspecific adsorption. Examples of a criterion for determining whether or not the binding is specific can include binding activity $EC_{50}$ in ELISA. Other examples of the criterion of determination can include the dissociation constant (hereinafter, referred to as "$K_D$"). The $K_D$ value of the HTRA1-inhibiting peptide according to the present invention for HTRA1 is $1 \times 10^{-4}$ M or lower, $1 \times 10^{-5}$ M or lower, $5 \times 10^{-6}$ M or lower, $2 \times 10^{-6}$ M or lower or $1 \times 10^{-6}$ M or lower, more preferably $5 \times 10^{-7}$ M or lower, $2 \times 10^{-7}$ M or lower or $1 \times 10^{-7}$ M or lower, still more preferably $5 \times 10^{-8}$ M or lower, $2 \times 10^{-8}$ M or lower or $1 \times 10^{-8}$ M or lower, further preferably $5 \times 10^{-9}$ M or lower, $2 \times 10^{-9}$ M or lower or $1 \times 10^{-9}$ M or lower. Other examples of the criterion of determination can include results of analysis by an immunoprecipitation method. The preferred HTRA1-inhibiting peptide according to the present invention is immobilized on beads, and HTRA1 is added thereto. Then, the beads are separated, and HTRA1 precipitated with the beads is detected. In this case, the signal of HTRA1 is detected.

In spite of the description above, the ability to bind to HTRA1 or the immunogenic fragment thereof is not essential for the SPINK2 mutant serving as the inhibiting peptide of the present invention as long as the SPINK2 mutant has HTRA1 inhibitory activity.

The inhibiting peptide of the present invention may be competitive in the binding of a protease substrate to HTRA1.

In some preferred aspects, the inhibiting peptide of the present invention has a retinal protective effect. For example, the preferred inhibitor of the present invention can suppress a light exposure-induced decrease in nucleus count in an outer nuclear layer in a model of retinal damage induced by light exposure, which is described in detail in the Examples. A larger amount of the HTRA1 protein has been detected in the vitreous humor of the light exposure group of this model, as compared with a non-exposure group. Thus, the present invention discloses that: HTRA1 is involved in retinal damage; and HTRA1 inhibitory activity brings about a retinal protective effect.

The SPINK2 mutant serving as the inhibiting peptide of the present invention can have the activities, the properties, the functions, the features, etc. as described above, whereas its full-length amino acid sequence has high sequence identity to the amino acid sequence of human wild-type SPINK2. The SPINK2 mutant of the present invention has 60% or higher, 70% or higher, 75% or higher, 80% or higher, 85% or higher, 90% or higher, 95% or higher, 98% or higher or 99% or higher sequence identity to the amino acid sequence (SEQ ID NO: 1; FIG. 13) of human SPINK2.

The term "identity" is used to mean a property that indicates the degree of similarity or relation between two sequences. The identity (%) of amino acid sequences is calculated by dividing the number of identical amino acids or amino acid residues by the total number of amino acids or amino acid residues and multiplying the resulting numeric value by 100.

The term "gap" is used to mean a space in the alignment between two or more sequences as a result of a deletion and/or addition in at least one of the two or more sequences.

The identity between two amino acid sequences having completely identical amino acid sequences is 100%. Provided that one of the amino acid sequences has the substitution, deletion or addition of one or two or more amino acids or amino acid residues as compared with the other amino acid sequence, the identity between these two amino acid sequences is lower than 100%. Examples of an algorithm or a program for determining the identity between two sequences in consideration of a gap can include those known to a person skilled in the art, such as BLAST (Altschul, et al., Nucleic Acids Res., Vol. 25, p. 3389-3402, 1997), BLAST2 (Altschul, et al., J. Mol. Biol., Vol. 215, p. 403-410, 1990), and Smith-Waterman (Smith, et al., J. Mol. Biol., Vol. 147, p. 195-197, 1981).

In the present invention, the term "mutated" is used to mean that one or two or more nucleotides or nucleotide residues or amino acids or amino acid residues are substituted, deleted or inserted in a nucleotide sequence or an amino acid sequence compared with a naturally occurring nucleic acid molecule or peptide. The amino acid sequence of the SPINK2 mutant of the present invention has one or two or more mutated amino acids or amino acid residues as compared with the amino acid sequence of human SPINK2.

In an aspect of the present invention, the amino acid sequence of the SPINK2 mutant may have any of: the substitution of 1, 2, 3, 4, 5, 6 or 7 amino acids from 16Ser to 22Gly with other amino acids or amino acid residues; the substitution of 1, 2, 3, 4 or 5 amino acids from 24Pro to 28Asn with other amino acids or amino acid residues; the substitution of 1 or 2 amino acids from 39Ala and 43Thr with other amino acids or amino acid residues in the amino acid sequence (SEQ ID NO: 1: FIG. 13) of human SPINK2, or may have these amino acids as wild-type ones (the 2 amino acids or amino acid residues are included in an a helix) as long as the tertiary structure of the principal chain of a loop constituted by amino acid residues at positions 16 to 30, etc. is capable of at least partially exerting HTRA1 inhibitory activity; each of 15Cys, 23Cys, 31Cys, 42Cys, 45Cys and 63Cys is preferably Cys, as in the wild-type, in order to maintain natural disulfide bonds. 1, 2, 3, 4, 5 or 6 thereof may be substituted with other amino acids in order to delete natural disulfide bonds or generate a non-natural disulfide bond. Some preferred HTRA1-inhibiting peptides among the SPINK2 mutants of the present invention maintain Cys at these 6 positions, as in natural SPINK2, and retain the disulfide bonds. In some more preferred forms of such an inhibiting peptide, 15Cys-45Cys, 23Cys-42Cys, and 31Cys-63Cys respectively form disulfide bonds.

When the amino acid sequence of such a SPINK2 mutant is contained in the HTRA1-inhibiting peptide, it is preferred that a three-dimensional structure constituted by, for example, a loop structure consisting of 16Ser to 30Val, a β sheet constituted by β strand (1) consisting of 31Cys and 32Gly and β strand (2) consisting of 57Ile to 59Arg, an α helix consisting of 41Glu to 51Gly, or a loop structure, β sheet, or α helix similar thereto or at least partially corresponding thereto (or to these positions), contained in the amino acid sequence of wild-type SPINK2 should be maintained to the extent that HTRA1 inhibitory activity can be exerted.

The amino acid sequences of some HTRA1-inhibiting peptides among the SPINK2 mutants of the present invention will be mentioned below. As mentioned above, in the present invention, the term "amino acid residue" is also simply referred to as an "amino acid".

Each of the first to eleventh Xaa (which are the same as X1 to X11, respectively) in the amino acid sequence shown in SEQ ID NO: 30 (FIG. 42) is any arbitrary amino acid without particular limitations as long as the resulting mutant binds to HTRA1 and inhibits HTRA1 activity. Hereinafter, preferred amino acids of X1 to X11 will be described. However, these amino acids may include natural amino acids, i.e., amino acids identical to those in the amino acid sequence of wild-type human SPINK2.

X1 at position 1 is preferably Asp, Glu, Gly, Ser or Ile, more preferably Asp or Gly, and still more preferably Gly;

X2 at position 16 is preferably Ala, Asp, Glu, Phe, Gly, His, Lys, Leu, Met, Gln, Arg, Ser, Thr or Tyr, more preferably Ala, Asp, Gly, His, Lys, Leu, Met, Gln, Arg, Ser or Thr, still more preferably Ala, Gly, Lys, Leu, Ser or Thr, further preferably Ala, Gly, Leu, Ser or Thr, and still further preferably Ala or Ser;

X3 at position 17 is preferably Ala, Asp, Glu, Gly, His, Lys, Leu, Met, Asn, Gln, Arg, Ser, Thr or Tyr, more preferably Asp, Gly, His, Lys, Leu, Met, Asn, Gln, Arg, Ser, Thr or Tyr, still more preferably Asp, His, Lys, Met or Gln, and further preferably Asp or Gln;

X4 at position 18 is preferably Ala, Asp, Glu, Phe, Gly, His, Ile, Leu, Lys, Met, Asn, Gln, Arg, Ser, Thr, Val, Trp or Tyr, more preferably Asp, Phe, His, Met, Asn, Gln, Ser or Tyr, still more preferably Asp, Phe, His, Ser or Tyr, and further preferably Phe or His;

X5 at position 19 is preferably Ala, Asp, Glu, Gly, His, Ile, Lys, Met, Asn, Gln, Arg, Ser, Thr, Val or Tyr, more preferably Ala, Asp, Glu, Gly, His, Lys, Met, Asn, Gln, Arg, Ser or Val, still more preferably Ala, Asp, Glu, Met or Asn, and further preferably Ala, Asp or Glu;

X6 at position 21 is preferably Ala, Glu, Phe, Gly, Ile, Leu, Met, Gln, Arg, Ser, Trp or Tyr, more preferably Glu, Phe, Ile, Leu, Met, Gln, Arg or Trp, still more preferably Met or Trp, further preferably Met;

X7 at position 24 is preferably Ala, Asp, Glu, Phe, Gly, His, Lys, Leu, Met, Pro, Gln, Arg, Ser, Thr, Val, Trp or Tyr, more preferably Asp, Glu, His, Pro, Gln, Ser, Thr, Val, Trp or Tyr, still more preferably Gln, Trp, Tyr or Val, and further preferably Tyr or Val;

X8 at position 26 is preferably Ala, Asp, Glu, Phe, His, Ile, Lys, Leu, Met, Asn, Gln, Arg, Ser, Val or Tyr, more preferably Ala, Phe, His, Ile, Leu, Met, Gln, Arg, Ser, Val or Tyr, still more preferably Phe, Leu or Tyr, and further preferably Phe or Leu;

X9 at position 27 is preferably Glu, Phe, Leu, Ser, Thr or Tyr, more preferably Phe, Leu, Ser, Thr or Tyr, still more preferably Phe or Tyr, further preferably Tyr;

X10 at position 39 is preferably Ala, Glu, Met or Val, and more preferably Ala or Glu; and X11 at position 43 is preferably Ala, Thr or Val, more preferably Thr or Val.

Wild-type X1 to X11 are Asp, Ser, Gln, Tyr, Arg, Pro, Pro, His, Phe, Ala and Thr, respectively. Position 20 is Leu, position 22 is Gly, position 25 is Arg, and position 28 is Asn.

In the present invention, one or several or more amino acids may be further added to the N-terminal side of the first amino acid. Examples of such amino acids to be added can include Ser-Leu, and an amino acid sequence consisting of S tag and a linker (SEQ ID NO: 31: FIG. 43).

One or several amino acids may be further added to 63Cys positioned at the C terminus. Examples of such an amino acid sequence can include an amino acid sequence having 64Gly at the C terminus, and an amino acid sequence having 65Gly at the C terminus by the addition of Gly-Gly. Examples of such an amino acid to be added can include Gly-Gly, and a C-terminal hexamer (SEQ ID NO: 32: FIG. 44).

A more preferred form of an amino acid sequence prepared by the addition of other amino acids to the N terminus and/or C terminus of the amino acid sequence shown in SEQ ID NO: 30 (FIG. 42) or an amino acid sequence derived from SEQ ID NO: 30 includes an amino acid sequence shown in any one of SEQ ID NOs: 3, 5, 7, 9, 11, 13, 15, 17, 19, 21 and 23 to 29 (FIGS. 15, 17, 19, 21, 23, 25, 27, 29, 31, 33 and 35 to 41) and an amino acid sequence encoded by a nucleotide sequence shown in any one of SEQ ID NOs: 4, 6, 8, 10, 12, 14, 16, 18, 20 and 22 (FIGS. 16, 18, 20, 22, 24, 26, 28, 30, 32 and 34). A still more preferred form thereof includes an amino acid sequence shown in any one of SEQ ID NOs: 24, 28 and 29 (FIGS. 36, 40 and 41).

In the present invention, a peptide prepared by the substitution, addition and/or deletion of one or two or more amino acids in, to or from the SPINK2 mutant peptide or the N-terminal and/or C-terminal adduct of the SPINK2 mutant peptide (hereinafter, referred to as a "parent peptide") is referred to as a "derivative of the parent peptide" or a "parent peptide derivative" (e.g., Example 6). Such a "derivative" is also included within the scope of the "peptide" of the present invention.

The amino acid sequence of the SPINK2 mutant included within the scope of the inhibiting peptide of the present invention can comprise a natural amino acid or a mutated amino acid or amino acid sequence at moieties other than X1 to X11, i.e., the positions of 2Pro to 15Cys, 20Leu, 22Gly, 23Cys, 25Arg, 28Asn to 38Tyr, 41Glu, 42Cys and 44Thr to 63Cys, in the amino acid sequence (SEQ ID NO: 1: FIG. 13) of wild-type human SPINK2. For example, the SPINK2 mutant may have a mutation at one or two or more positions as long as HTRA1 inhibitory activity or folding is at least partially neither hindered nor interfered with. Such a mutation is attained by use of a standard method known to a person skilled in the art. Typical examples of the mutation in the amino acid sequence can include the substitution, deletion or addition of one or two or more amino acids. Examples of the substitution can include conservative substitution. The conservative substitution substitutes a certain amino acid residue with an amino acid residue similar thereto in chemical features in terms of not only bulkiness but polarity. Examples of the conservative substitution are described in other sections of the present specification. On the other hand, the moieties other than X1 to X11 may accept the non-conservative substitution of one or two or more amino acids as long as HTRA1 inhibitory activity or folding is at least partially neither hindered nor interfered with.

In the amino acid sequence of the SPINK2 mutant serving as the inhibiting peptide of the present invention, X1 to X11 are preferably amino acids X1 to X11, respectively, in any one of SEQ ID NOs: 3, 5, 7, 9, 11, 13, 15, 17, 19, 21 and 23 to 29 (FIGS. 15, 17, 19, 21, 23, 25, 27, 29, 31, 33 and 35 to 41), and more preferably SEQ ID NOs: 24, 28 and 29 (FIGS. 36, 40 and to 41), and the moieties other than X1 to X11 can have an amino acid or an amino acid sequence that at least partially neither hinders nor interferes with HTRA1 inhibitory activity or folding.

Examples of the amino acid sequence of the SPINK2 mutant serving as the HTRA1-inhibiting peptide of the present invention can include any one of the following amino acid sequences (a) to (e):
(a) an amino acid sequence shown in any one of SEQ ID NOs: 3, 5, 7, 9, 11, 13, 15, 17, 19, 21, and 23 to 29 (FIGS. 15, 17, 19, 21, 23, 25, 27, 29, 31, 33, and 35 to 41);
(b) an amino acid sequence encoded by a nucleotide sequence which hybridizes under stringent conditions to a nucleotide sequence complementary to a nucleotide sequence encoding amino acid sequence (a) and encodes an amino acid sequence comprised in a peptide having HTRA1 inhibitory activity;
(c) an amino acid sequence which is derived from amino acid sequence (a) by the substitution, deletion, addition and/or insertion of 1 to 20, 1 to 15, 1 to 10, 1 to 8, 1 to 6, 1 to 5, 1 to 4, 1 to 3, 1 or 2, or 1 amino acid and comprised in a peptide having HTRA1 inhibitory activity;
(d) an amino acid sequence which has 60%, 70%, 80%, 85%, 90%, 92%, 94%, 96%, 97%, 98% or 99% or higher identity to amino acid sequence (a) and is comprised in a peptide having HTRA1 inhibitory activity; and
(e) an amino acid sequence encoded by a nucleotide sequence shown in any one of SEQ ID NOs: 4, 6, 8, 10, 12, 14, 16, 18, 20 and 22 (FIGS. 16, 18, 20, 22, 24, 26, 28, 30, 32 and 34).

However, the amino acid sequence of the HTRA1-inhibiting peptide is not limited to (a) to (e). Every amino acid sequence contained in a SPINK2 mutant having HTRA1 inhibitory activity, and preferably the amino acid sequence shown in SEQ ID NO: 30 (FIG. 42), is included within the scope of the amino acid sequence of the HTRA1-inhibiting peptide.

A mutation can be introduced to the inhibiting peptide of the present invention for the purpose of improving its folding stability, thermal stability, storage stability, half-life in blood, water solubility, biological activity, pharmacological activity, secondary effect, etc. For example, a new reactive group such as Cys can be introduced thereto by a mutation in order to conjugate the inhibiting peptide to an additional substance such as polyethylene glycol (PEG), hydroxyethyl starch (HES), biotin, a peptide or a protein. In the present invention, the HTRA1-inhibiting peptide may be added, linked, or bound to an additional moiety. Such conjugates are collectively referred to as a "conjugate of the HTRA1-inhibiting peptide". In the present invention, the term "conjugate" is used to mean a molecule of the peptide of the present invention or a fragment thereof added, linked or bound to an additional moiety. The term "conjugate" or "conjugation" includes a form in which a certain moiety is linked or bound, via an agent or the like suitable for linking the certain moiety to the side chain of an amino acid, including a chemical substance such as a cross-linking agent, to the N terminus and/or C terminus of the peptide of the present invention by a synthetic chemical approach, a genetic engineering approach, or the like. Examples of such a "moiety" for improving the half-life in blood can include polyalkylene glycol molecules such as polyethylene glycol (PEG), hydroxyethyl starch, fatty acid molecules such as palmitic acid, immunoglobulin Fc regions, immunoglobulin CH3 domains, immunoglobulin CH4 domains, albumin or fragments thereof, albumin-binding peptides, albumin-binding proteins such as streptococcal protein G, and transferrin. Alternatively, the "moiety" may be linked to the peptide of the present invention via a linker such as a peptide linker.

The HTRA1-inhibiting peptide of the present invention may be conjugated with an additional drug in order to exert or enhance pharmacological activity. In the field of antibodies, a technique or a form known to a person skilled in the art as antibody-drug conjugates (ADCs) constitutes some aspects of the present invention by the replacement of the antibody with the peptide of the present invention.

The HTRA1-inhibiting peptide of the present invention may further comprise one or two or more moieties that exert binding affinity, inhibitory activity, antagonistic activity, agonistic activity, or the like against a target molecule other than HTRA1, or may be conjugated with such moieties. Examples of the "moiety" can include antibodies or fragments thereof, and proteins having a non-antibody framework, such as SPINK2 mutants, or fragments thereof. In the field of antibodies, a technique or a form known to a person skilled in the art as multispecific antibodies and bispecific antibodies constitutes some aspects of the conjugate of the present invention by the replacement of at least one or two or more "antibodies" comprised therein with the peptide of the present invention.

The peptide of the present invention or a precursor thereof may comprise a signal sequence. A signal sequence present at or added to the N terminus of a certain polypeptide or a precursor thereof is useful for delivering the polypeptide to a specific compartment of a cell, for example, the periplasm of E. coli or the endoplasmic reticulum of a eukaryotic cell. Many signal sequences are known to a person skilled in the art, and the signal sequence can be selected according to host cells. Examples of the signal sequence for secreting the desired peptide into the periplasm of E. coli can include OmpA. The form comprising the signal sequence can also be included within some aspects of the conjugate of the present invention.

The peptide of the present invention can be tagged in advance and thereby purified by affinity chromatography. The peptide of the present invention can comprise, for example, biotin, Strep tag™, Strep tag II™, oligohistidine such as His6, polyhistidine, an immunoglobulin domain, a maltose-binding protein, glutathione-S-transferase (GST), a calmodulin-binding peptide (CBP), a hapten such as digoxigenin or dinitrophenol, an epitope tag such as FLAG™, a myc tag, or a HA tag (hereinafter, collectively referred to as an "affinity tag") at its C-terminus. The tagged form can also be included within some aspects of the conjugate of the present invention. The conjugate of the present invention, as a whole, may be a peptide (polypeptide).

The peptide of the present invention can comprise a moiety for labeling. Specifically, the peptide of the present invention can be conjugated to a label moiety such as an enzymatic label, a radiolabel, a colored label, a fluorescent label, a coloring label, a luminescent label, a hapten, digoxigenin, biotin, a metal complex, a metal, or colloidal gold. The form comprising the moiety for labeling can also be included within some aspects of the conjugate of the present invention.

The inhibiting peptide of the present invention can comprise any of the natural amino acids and non-natural amino acids in its peptide moiety and can comprise an L-amino acid and a D-amino acid as a natural amino acid.

The amino acid sequence of the inhibiting peptide of the present invention can comprise any of the natural amino acids and non-natural amino acids and can comprise an L-amino acid and a D-amino acid as a natural amino acid.

The inhibiting peptide of the present invention can be present as a monomer, a dimer, or a trimer or higher oligomer or multimer. The dimer or the trimer or higher oligomer or multimer can be any of a homo form constituted by single monomers, and a hetero form constituted by two or more different monomers. The monomer may be rapidly diffused and be excellent in permeation into tissues, for example. The dimer, the oligomer and the multimer may have an excellent aspect, for example, high local affinity or binding activity for a target molecule, a slow dissociation rate, or high HTRA1 inhibitory activity. In addition to spontaneous dimerization, oligomerization and multimerization, intended dimerization, oligomerization and multimerization are attained by introducing a jun-fos domain, leucine zipper, or the like to the inhibiting peptide of the present invention.

The inhibiting peptide of the present invention can bind to one or two or more target molecules or inhibit the activity of the target molecules, in the form of a monomer, a dimer, or a trimer or higher oligomer or multimer.

Examples of the form that can be taken by the inhibiting peptide of the present invention can include, but are not limited to, isolated forms (freeze-dried preparations, solutions, etc.), the conjugates mentioned above, and forms bound to other molecules (immobilized forms, associations with a different molecule, forms bound to a target molecule, etc.). A form compatible with expression, purification, use, storage, or the like can be arbitrarily selected.

3. Identification of HTRA1-Inhibiting Peptide

The HTRA1-inhibiting peptide can be identified by a method well known to a person skilled in the art using a starting material such as the amino acid sequence of SPINK2 or the amino acid sequence (e.g., an amino acid sequence selected from the group consisting of SEQ ID NOs: 3, 5, 7, 9, 11, 13, 15, 17, 19, 21 and 23 to 29, or the group consisting of FIGS. 15, 17, 19, 21, 23, 25, 27, 29, 31, 33 and 35 to 41) of the HTRA1-inhibiting peptide of the present invention, a nucleotide sequence encoding the amino acid sequence, or a nucleic acid molecule comprising the nucleotide sequence. As a preferred example, the HTRA1-inhibiting peptide can be identified from a human SPINK2 mutant library by using HTRA1 inhibitory activity as an indicator which may be combined with HTRA1 binding activity as another indicator.

For example, the nucleic acid molecule serving as a starting material can be mutagenized and transferred into an appropriate bacterial host or eukaryotic host by use of a recombinant DNA technique. The SPINK2 mutant library is known as a technique for identifying a binder or an inhibitor of a target molecule. For example, the disclosure of WO2012/105616 is also incorporated herein by reference in its entirety. After expression of the mutagenized nucleotide sequence in the appropriate host, a clone in which a SPINK2 mutant having the desired properties, activity, function, etc. is linked to its genotype can be enriched and/or selected from the library and identified. The enrichment and/or selection of the clone employs a method known to a person skilled in the art, such as a bacterial display method (Francisco, J. A., et al., (1993), Proc. Natl. Acad. Sci. U.S.A. Vol. 90, p. 10444-10448), a yeast display method (Boder, E. T., et al., (1997), Nat. Biotechnol., Vol. 15, p. 553-557), a mammalian cell display method (Ho M, et al., (2009), Methods Mol Biol., Vol. 525: p. 337-52), a phage display method (Smith, G. P. (1985), Science., Vol. 228, p. 1315-1317), a ribosome display method (Mattheakis L C, et al., (1994), Proc. Natl. Acad. Sci. U.S.A. Vol. 91, No. 19, p. 9022-9029), a nucleic acid display method such as mRNA display (Nemoto N, et al., (1997), FEBS Lett., Vol. 414, No. 2, p. 405-408), or a colony screening method (Pini, A. et al., (2002), Comb. Chem. High Throughput Screen., Vol. 5, p. 503-510). The nucleotide sequence of a SPINK2 mutant contained in the clone thus selected and identified can be determined to determine an amino acid sequence encoded by the nucleotide sequence as the amino acid sequence of the SPINK2 mutant contained in the clone, i.e., the HTRA1-inhibiting peptide.

The SPINK2 mutant of the present invention can be obtained, for example, by mutagenizing natural SPINK2. The term "mutagenesis" is used to mean that one or two or more amino acids at their respective positions of a certain amino acid sequence can be substituted by other amino acids or deleted, or an amino acid absent from the amino acid sequence can be added or inserted thereinto. Such a deletion or such an addition or insertion can change the sequence length. In the SPINK2 mutant of the present invention, the mutagenesis can preferably occur at one or two or more positions of X1 to X11 in the amino acid sequence shown in SEQ ID NO: 30 (FIG. 42).

However, a form that maintains, after such preferred mutagenesis, natural amino acids at one or two or more positions of X1 to X11, i.e., the same amino acid as that present at the specific position in the natural amino acid sequence, is also included within the scope of the mutant as long as at least one amino acid is mutated in the whole. Likewise, in an aspect of the present invention, a form that maintains, after mutagenesis at one or more positions of moieties other than X1 to X11, natural amino acids at these positions, i.e., the same amino acid as that present at the specific position in the natural amino acid sequence, is also included within the scope of the mutant as long as at least one amino acid is mutated in the whole.

The term "random mutagenesis" is used to mean that as to a specific position on a sequence, one or two or more different amino acids are introduced with a given probability to the position by mutagenesis. The probabilities of introduction of at least two different amino acids may not always be the same. The present invention does not exclude said at least two different amino acids from including the naturally-occurring amino acid (as one of the amino acids). Such a case is also included within the scope of the term "random mutagenesis".

A standard method known to a person skilled in the art can be used as a method for random mutagenesis at a specific position. The mutagenesis can be attained by, for example, PCR (polymerase chain reaction) using a mixture of synthetic oligonucleotides including a degenerate nucleotide composition at a specific position in a sequence. For example, use of codon NNK or NNS (N=adenine, guanine, cytosine or thymine; K=guanine or thymine; and S=guanine or cytosine) causes mutagenesis to introduce any of all 20 natural amino acids as well as a stop codon, whereas use of codon VVS (V=adenine, guanine or cytosine) eliminates the possibility of introducing Cys, Ile, Leu, Met, Phe, Trp, Tyr and Val and causes mutagenesis to introduce any of the remaining 12 natural amino acids. For example, use of codon NMS (M=adenine or cytosine) eliminates the possibility of introducing Arg, Cys, Gly, Ile, Leu, Met, Phe, Trp and Val and causes mutagenesis to introduce any of the remaining 11 natural amino acids. A specific codon, an artificial codon, or the like can be used for mutagenesis to introduce a non-natural amino acid.

The site-directed mutagenesis can also be performed through the use of structural information on a target containing a conformation and/or a peptide against the target or a wild-type peptide from which the peptide is derived. In the present invention, a site-directed mutation can be introduced through the use of structural information including higher-order information on the target HTRA1 and/or a SPINK2 mutant against the target or wild-type SPINK2, or a complex therebetween. In one example, a SPINK2 mutant having HTRA1 inhibitory activity is identified. Subsequently, a crystalline complex of HTRA1 and the SPINK2 mutant is obtained and subjected to X-ray crystallography. On the basis of the analysis results, a site on the HTRA1 molecule to which the SPINK2 mutant binds, and an amino acid residue in the SPINK2 mutant involved in interaction with the site are identified. The correlation of structural information obtained through such procedures with HTRA1 inhibitory activity may be found. On the basis of such a structure-activity correlation, the substitution of an amino acid at a specific position with a specific amino acid, the insertion or deletion of an amino acid at a specific position, or the like can be designed to actually confirm HTRA1 activity.

The mutagenesis can also be attained using, for example, a nucleotide constituent unit with modified base pair specificity, such as inosine.

Furthermore, mutagenesis at a random position is achieved by, for example, error-prone PCR using DNA polymerase, such as Taq DNA polymerase, which lacks an error correcting function and produces a high rate of errors, or chemical mutagenesis.

The HTRA1-inhibiting peptide can be enriched and/or selected from a library, such as a phage library or a colony library, which is suitable for the respective screening method and known to a person skilled in the art, through the use of bacterial display, yeast display, mammalian cell display, phage display, ribosome display, nucleic acid display, colony screening, or the like. These libraries can be constructed using a vector and a method, such as a phagemid for the phage library or a cosmid for the colony screening, which are suitable for each library and known to a person skilled in the art. Such a vector may be a virus or viral vector that infects prokaryotic cells or eukaryotic cells. These recombinant vectors can be prepared by a method known to a person skilled in the art, such as genetic manipulation.

Bacterial display is a technique of fusing a desired protein with, for example, a portion of *E. coli* outer membrane lipoprotein (Lpp) and outer membrane protein OmpA, and displaying the desired protein on the surface of *E. coli*. A DNA group obtained by the random mutagenesis of a nucleotide sequence encoding the amino acid sequence of a certain protein is inserted into vectors suitable for bacterial display, and bacterial cells can be transformed with the vectors to obtain a library displaying a randomly mutagenized protein group on transformed bacterial cell surface (Francisco, J. A., et al., (1993), Proc. Natl. Acad. Sci. U.S.A. Vol. 90, p. 10444-10448).

Yeast display is a technique of fusing a desired protein with a coat protein such as (X-agglutinin which is on the cell surface of yeast, and displaying the desired protein on the surface of yeast. The α-agglutinin comprises a C-terminal hydrophobic region with a putative glycosylphosphatidylinositol (GPI) anchor attachment signal, a signal sequence, an active domain, a cell wall domain, and the like. The desired protein can be displayed on the cell surface of yeast by manipulation thereof. A DNA group obtained by the random mutagenesis of a nucleotide sequence encoding the amino acid sequence of a certain protein is inserted into vectors suitable for yeast display, and yeast cells can be transformed with the vectors to obtain a library displaying a randomly mutagenized protein group on the cell surface of transformed yeast (Ueda, M.& Tanaka, A., Biotechnol. Adv., Vol. 18, p. 121-, 2000; Ueda, M.& Tanaka, A., J. Biosci. Bioeng., Vol. 90, p. 125-, 2000; etc.).

Animal cell display is a technique of fusing a desired protein with, for example, the transmembrane region of a membrane protein typified by platelet-derived growth factor receptor (PDGFR), and displaying the desired protein on the surface of mammalian cells (e.g., HEK293 and Chinese hamster ovary (CHO) cells). A DNA group obtained by the random mutagenesis of a nucleotide sequence encoding the amino acid sequence of a certain protein is inserted into vectors suitable for animal cell display, and animal cells can be transfected with the vectors to obtain a library displaying a randomly mutagenized protein group on the surface of transfected animal cells (Ho M, et al., (2009), Methods Mol Biol. Vol. 525: p. 337-52).

The desired library displayed on cells such as yeast cells, bacterial cells, or animal cells can be incubated in the presence of a target molecule or contacted with a target molecule. For example, the cells involving the library are incubated for a given time with HTRA1 modified with biotin or the like. Then, a support such as magnetic beads is added thereto, and the cells are separated from the support. Subsequently, the support can be washed to effect the removal of nonspecific adsorbed matter and bound matter in order to recover a cell group displaying a peptide, a peptide collection or an enriched peptide collection bound to the support (which has HTRA1 bound thereto). Likewise, the cell group displaying a peptide, a peptide collection or an enriched peptide collection bound to the support (which has HTRA1 bound thereto), or the cell group displaying a peptide, a peptide collection or an enriched peptide collection bound to HTRA1, can be recovered by magnetic-activated cell sorting (MACS) after addition of the magnetic beads, or by FACS after cell staining using an anti-HTRA1 antibody, respectively. A nonspecific adsorption site and/or binding site may be blocked (saturated), for example. The blocking step can be incorporated herein as long as the blocking is performed by an appropriate method. The vector of the expressed peptide, peptide collection or enriched peptide collection thus obtained is recovered, and the nucleotide sequence of the polynucleotide inserted into the vector can be determined to determine the amino acid sequence encoded by the nucleotide sequence. Moreover, the vector can be transferred again into host cells, and a cycle of the operation mentioned above can be repeated once to several times to enrich highly a peptide collection which binds to the target molecule.

In the case of phage display, for example, the phagemid is a bacterial plasmid containing a plasmid replication origin as well as a second replication origin derived from a single-stranded bacteriophage. A cell having the phagemid can replicate the phagemid via a single-strand replication mode by co-infection with M13 or a helper bacteriophage similar thereto. Specifically, single-stranded phagemid DNA is packaged into an infectious particle coated with a bacteriophage coat protein. In this way, the phagemid DNA can be formed as a clonal double-stranded DNA plasmid in an infected bacterium, while the phagemid can be formed as a bacteriophage-like particle from the culture supernatant of co-infected cells. The bacteriophage-like particle is injected into a bacterium having F-pilus for the infection of the bacterium with the DNA so that the particle itself can be re-formed as a plasmid.

A fusion gene comprising a polynucleotide having a nucleotide sequence encoding the amino acid sequence of a test peptide and a bacteriophage coat protein gene is inserted into the phagemid, and a bacterium is infected with the resulting phagemid. The cells are cultured so that the peptide can be expressed or displayed on the bacterium or on a phage-like particle, or can be produced as a fusion protein with the coat protein into a phage particle or into a culture supernatant of the bacterium.

For example, a fusion gene comprising the polynucleotide and the bacteriophage coat protein gene gpIII is inserted into the phagemid, and *E. coli* is co-infected with the resulting phagemid and M13 or a helper phage similar thereto so that a fusion protein comprising the peptide and the coat protein can be produced and released into the culture supernatant of the *E. coli*.

In the case of using various circular or noncircular vectors, for example, a virus vector, instead of the phagemid, a peptide having an amino acid sequence encoded by the nucleotide sequence of the polynucleotide inserted in the vector can be expressed or displayed on cells or virus-like particles harboring the vector, or can be produced and released into the culture supernatant of the cells, according to a method known to a person skilled in the art.

The peptide-expressing library thus obtained can be incubated in the presence of a target molecule, or contacted with a target molecule. For example, a HTRA1-immobilized support is incubated for a given time with a mobile phase containing the library. Then, the mobile phase is separated from the support. Subsequently, the support is washed to effect the removal of nonspecific adsorbed matter and bound matter. A peptide, a peptide collection or an enriched peptide collection bound to the support (which has HTRA1 bound thereto) can be recovered by elution. The elution can be non-selectively performed, for example, in the presence of relatively high ionic strength, low pH, moderate denaturation conditions, or chaotropic salt, or can be selectively performed by adding a soluble target molecule such as HTRA1, an antibody which binds to the target molecule, a natural ligand, a substrate, or the like and competing with an immobilized target molecule. A non-specific adsorption site and/or binding site may be blocked, for example. The blocking step can be incorporated herein as long as the blocking is performed by an appropriate method.

The vector of the expressed peptide, peptide collection or enriched peptide collection thus obtained is recovered, and the nucleotide sequence of the polynucleotide inserted in the vector can be determined to determine an amino acid sequence encoded by the nucleotide sequence. Moreover, the vector can be transferred again into host cells, and a cycle of the operation mentioned above can be repeated once to several times to enrich highly a peptide collection which binds to the target molecule.

Ribosome display is a technique of using, for example, mRNA that encodes a desired protein and lacks a stop codon, and a cell-free protein synthesis system, and thereby synthesizing in vitro a molecule of the desired protein, its corresponding mRNA, and a ribosome linked to each other. A library displaying a randomly mutagenized protein group on ribosomes can be obtained through the use of a mRNA group obtained by the random mutagenesis of a nucleotide sequence encoding the amino acid sequence of a certain protein, and a cell-free protein synthesis system (Mattheakis L C, et al., (1994) Proc. Natl. Acad. Sci. U.S.A. Vol. 91, No. 19, p. 9022-9029).

Nucleic acid display, also called mRNA display, is a technique of using, for example, a linker such as puromycin that is structurally similar to the 3' end of tyrosyl tRNA, and thereby synthesizing a molecule of a desired protein, its encoding mRNA and a ribosome linked to each other. This technique employs a cell-free protein synthesis system, not live cells, and therefore permits in vitro synthesis. A library displaying a randomly mutagenized protein group on a ribosome can be obtained through the use of an mRNA group obtained by the random mutagenesis of a nucleotide sequence encoding the amino acid sequence of a certain protein, a linker such as puromycin, and a cell-free protein synthesis system (Nemoto N, et al., (1997), FEBS Lett., Vol. 414, No. 2, p. 405-408).

The peptide-displaying library obtained via a cell-free synthesis system, such as ribosome display or nucleic acid display, can be incubated in the presence of a target molecule, or contacted with a target molecule. For example, a HTRA1-immobilized support is incubated for a given time with a mobile phase containing the library. Then, the mobile phase is separated from the support. Subsequently, the support is washed to effect the removal of nonspecific adsorbed matter and bound matter. A peptide, a peptide collection or an enriched peptide collection bound to the support (which has HTRA1 bound thereto) can be recovered by elution. The elution can be non-selectively performed, for example, in the presence of relatively high ionic strength, low pH, moderate denaturation conditions, or chaotropic salt, or can be selectively performed by adding a soluble target molecule such as HTRA1, an antibody which binds to the target molecule, a natural ligand, a substrate, or the like and competing with an immobilized target molecule. A non-specific adsorption site and/or binding site may be blocked, for example. The blocking step can be incorporated herein as long as the blocking is performed by an appropriate method.

The nucleic acid of the expressed peptide, peptide collection or enriched peptide collection thus obtained is recovered. In the case of mRNA, the nucleotide sequence can be determined after a reverse transcription reaction into cDNA to determine an amino acid sequence encoded by the nucleotide sequence. Moreover, the recovered nucleic acid is transcribed into mRNA, and a cycle of the operation mentioned above can be repeated once to several times to enrich highly a peptide collection which binds to the target molecule.

Provided that the peptide, the peptide collection or the enriched peptide collection is conjugated in advance with an affinity tag, the peptide or the collection can be efficiently purified. For example, the peptide collection is conjugated in advance with a protease substrate as a tag so that the peptide can be eluted by cleavage through the protease activity.

On the basis of the obtained sequence information and the function of the peptide, etc., the obtained clone or library may be further mutagenized, and a peptide improved in its function (e.g., HTRA1 inhibitory activity), physical properties (thermal stability, storage stability, etc.), in vivo kinetics (distribution and half-life in blood), etc. can be obtained from the mutated library.

The HTRA1-inhibiting peptide can be identified by determining whether or not the obtained peptide has HTRA1 inhibitory activity.

The HTRA1-inhibiting peptide is preferably capable of maintaining a three-dimensional structure constituted by, for example, a loop structure consisting of 16Ser to 30Val, a β sheet constituted by β strand (1) consisting of 31Cys and 32Gly and β strand (2) consisting of 57Ile to 59Arg, and an α helix consisting of 41Glu to 51Gly, or a loop structure, β sheet, or α helix similar thereto or at least partially corresponding thereto (or to these positions), contained in the amino acid sequence of wild-type SPINK2, to the extent that HTRA1 inhibitory activity can be exerted. A more preferred HTRA1-inhibiting peptide may be identified by using such a three-dimensional structure (whole structure or partial structure) as part of an indicator.

4. Nucleic acid molecule encoding HTRA1-inhibiting peptide, vector comprising the nucleic acid molecule, cell comprising the nucleic acid molecule or the vector, and method for producing recombinant HTRA1-inhibiting peptide The present invention also provides a polynucleotide comprising a nucleotide sequence encoding an amino acid sequence contained in the HTRA1-inhibiting peptide (hereinafter, referred to as a "nucleic acid molecule encoding the HTRA1-inhibiting peptide"), a recombinant vector having an insert of the gene, a cell harboring the gene or the vector (hereinafter, referred to as a "cell containing the nucleic acid molecule encoding the HTRA1-inhibiting peptide"), or a cell producing the HTRA1-inhibiting peptide (hereinafter, referred to as a "HTRA1-inhibiting peptide-producing cell").

Some preferred examples of the nucleic acid molecule encoding the HTRA1-inhibiting peptide of the present invention can include a nucleic acid molecule comprising any one of the following nucleotide sequences (a) to (e) (hereinafter, referred to as the "nucleotide sequence of the HTRA1-inhibiting peptide"), a nucleic acid molecule consisting of a nucleotide sequence comprising the nucleotide sequence of the HTRA1-inhibiting peptide, and a nucleic acid molecule consisting of the nucleotide sequence of the HTRA1-inhibiting peptide:

(a) a nucleotide sequence encoding an amino acid sequence shown in any one of SEQ ID NOs: 3, 5, 7, 9, 11, 13, 15, 17, 19, 21, and 23 to 29 (FIGS. 15, 17, 19, 21, 23, 25, 27, 29, 31, 33, and 35 to 41);

(b) a nucleotide sequence shown in any one of SEQ ID NOs: 4, 6, 8, 10, 12, 14, 16, 18, 20 and 22 (FIGS. 16, 18, 20, 22, 24, 26, 28, 30, 32 and 34);

(c) a nucleotide sequence which hybridizes under stringent conditions to a nucleotide sequence complementary to the nucleotide sequence (a) or (b) and encodes an amino acid sequence comprised in a peptide having HTRA1 inhibitory activity;

(d) a nucleotide sequence which is derived from the nucleotide sequence (a) or (b) by the substitution, deletion, addition and/or insertion of 1 to 20, 1 to 15, 1 to 10, 1 to 8, 1 to 6, 1 to 5, 1 to 4, 1 to 3, 1 or 2, or 1 nucleotide or nucleotide residue and encodes an amino acid sequence comprised in a peptide having HTRA1 inhibitory activity; and (e) a nucleotide sequence which has 60%, 70%, 80%, 85%, 90%, 92%, 94%, 96%, 97%, 98% or 99% or higher identity to the nucleotide sequence (a) or (b) and encodes an amino acid sequence comprised in a peptide having HTRA1 inhibitory activity.

However, the nucleic acid molecule encoding the HTRA1-inhibiting peptide is not limited to the nucleotide sequences (a) to (e). Every nucleic acid molecule comprising a nucleotide sequence encoding an amino acid sequence comprised in a SPINK2 mutant having HTRA1 inhibitory activity, and preferably the amino acid sequence shown in SEQ ID NO: 30 (FIG. 42), is included within the scope of the nucleic acid molecule encoding the HTRA1-inhibiting peptide.

One or two or more codons corresponding to each amino acid can be used for designing the nucleotide sequence encoding the amino acid sequence. Hence, a nucleotide sequence encoding the single amino acid sequence of a certain peptide can have a plurality of variations. For the selection of such codons, the codons can be appropriately selected according to the codon usage of host cells for expression, which are to harbor a polynucleotide comprising the nucleotide sequence or a vector comprising the polynucleotide, or the frequency or rate of a plurality of codons used can be appropriately adjusted. For example, in the case of using *Escherichia coli* cells as host cells, the nucleotide sequence may be designed using codons with high frequency of use in *Escherichia coli*.

The nucleic acid molecule encoding the HTRA1-inhibiting peptide may be functionally linked to one or two or more regulatory sequences. The phrase "functionally linked" is used to mean that the linked nucleic acid molecule can be expressed, or a nucleotide sequence contained in the molecule is expressible. The regulatory sequence includes a sequence element that provides information on transcriptional regulation and/or translational regulation. Although the regulatory sequence varies depending on species, the regulatory sequence generally includes a promoter and includes 5' non-coding sequences involved in the initiation of transcription and translation, for example, a prokaryotic−35/−10 box and Shine-Dalgarno sequence or a eukaryotic TATA box, CAAT sequence, and 5' capping sequence. This sequence may comprise an enhancer element and/or a repressor element, and a translatable signal sequence, leader sequence, or the like for delivering a natural or mature peptide to a specific compartment inside or outside a host cell. The regulatory sequence may further include a 3' noncoding sequence, and this sequence may comprise an element involved in transcription termination or polyadenylation, etc. However, the sequence related to transcription termination, when functioning insufficiently in specific host cells, can be substituted with a sequence suitable for the cells.

Examples of the promoter sequence can include a prokaryotic tet promoter, a lacUV5 promoter, and a T7 promoter, and an SV40 promoter and a CMV promoter for eukaryotic cells.

The nucleic acid molecule encoding the HTRA1-inhibiting peptide may be in an isolated form or in a form contained in a vector or another cloning vehicle (hereinafter, simply referred to as a "vector"; plasmid, phagemid, phage, baculovirus, cosmid, etc.) or in a chromosome, though the form is not limited thereto. The vector may comprise, in addition to the nucleotide sequence of the HTRA1-inhibiting peptide and the regulatory sequence, a replicating sequence and a control sequence suitable for host cells for use in expression, and a selective marker which confers a phenotype that permits selection of cells harboring the nucleic acid molecule by transformation or the like.

The nucleic acid molecule encoding the HTRA1-inhibiting peptide or the vector comprising the nucleotide sequence of the HTRA1-inhibiting peptide can be transferred to host cells capable of expressing the peptide or the nucleotide sequence by a method known to a person skilled in the art, such as transformation. The host cells harboring the nucleic acid molecule or the vector can be cultured under conditions suitable for the expression of the peptide or the nucleotide sequence. The host cells can be any of prokaryotic and eukaryotic cells. Examples of the prokaryote can include *E. coli* and *Bacillus subtilis*. Examples of the eukaryotic cells can include cells of yeasts such as *Saccharomyces cerevisiae* and *Pichia pastoris*, insect cells such as SF9 and High 5, and animal cells such as HeLa cells, CHO cells, COS cells, and NS0. The peptide of the present invention expressed by using host cells such as eukaryotic cells can undergo a desired posttranslational modification. Examples of the posttranslational modification can include the addition of a functional group such as a sugar chain, the addition of a peptide or a protein, and the conversion of the chemical properties of an amino acid. Alternatively, the peptide of the present invention may be artificially modified as desired. Such a modified form of the peptide is also included within the scope of the "peptide" of the present invention.

The present invention also includes a method for producing the HTRA1-inhibiting peptide. The method comprises: step 1 of culturing a host cell harboring the nucleic acid molecule encoding the HTRA1-inhibiting peptide or the vector comprising the nucleotide sequence of the HTRA1-inhibiting peptide, or a cell expressing the HTRA1-inhibiting peptide; and/or step 2 of recovering the HTRA1-inhibiting peptide from the cultures obtained in step 1. An operation, such as fractionation, chromatography, or purification, known to a person skilled in the art can be applied to step 2. For example, affinity purification using the antibody of the present invention mentioned later is applicable thereto.

In some aspects of the present invention, the HTRA1-inhibiting peptide has an intramolecular disulfide bond. It may be preferred that the peptide having an intramolecular disulfide bond should be delivered to a cell compartment having an oxidizing redox environment, by using a signal sequence or the like. The oxidizing environment can be provided by the periplasm of a gram-negative bacterium such as *E. coli*, the extracellular environment of a gram-positive bacterium, the endoplasmic reticulum lumen of a eukaryotic cell, or the like. Such an environment is capable of promoting the formation of a structural disulfide bond. Alternatively, the peptide having an intramolecular disulfide bond may be prepared in the cytoplasm of a host cell such as an *E. coli* cell. In this case, the peptide can be directly acquired in a soluble folded state or recovered in the form of an inclusion body and subsequently reconstructed in vitro. Furthermore, a host cell having an oxidizing intracellular environment is selected, and the peptide having an intramolecular disulfide bond can also be prepared in the cytoplasm thereof. On the other hand, when the HTRA1-inhibiting peptide has no intramolecular disulfide bond, the peptide can be prepared in a cell compartment having a reducing redox environment, for example, the cytoplasm of a gram-negative bacterium.

The HTRA1-inhibiting peptide of the present invention can also be produced by other methods known to a person skilled in the art, such as chemical synthesis, for example, the solid-phase peptide synthesis method of Merrifield, et al. and an organic synthetic chemical peptide synthesis method using t-butoxycarbonyl (Boc) or 9-fluorenylmethoxycarbonyl (Fmoc), and in vitro translation.

5. Pharmaceutical Composition

The present invention also provides a pharmaceutical composition comprising the HTRA1-inhibiting peptide or a conjugate thereof.

The pharmaceutical composition comprising the HTRA1-inhibiting peptide of the present invention or the conjugate thereof is useful in the treatment and/or prevention of various diseases that are induced or exacerbated by HTRA1 and permit suppression of the induction or the exacerbation, cure, maintenance or amelioration of a symptom, avoidance of a secondary disease, etc. by inhibiting or suppressing the expression or function of HTRA1 (hereinafter, these diseases are referred to as "HTRA1-related diseases"). The HTRA1-related diseases also include various diseases that permit suppression of the induction or exacerbation, cure, maintenance or amelioration of a symptom, avoidance of a secondary disease, etc. through the suppression of photoreceptor cell degeneration. The HTRA1-inhibiting peptide of the present invention has a suppressive effect on photoreceptor cell degeneration and is useful in the treatment and/or prevention of these HTRA1-related diseases.

Examples of HTRA1-related diseases include, but are not limited to, various hereditary and non-hereditary eye diseases such as retinitis pigmentosa, hereditary diseases involving photoreceptor cell degeneration, and diseases involving photoreceptor cell degeneration resulting from PDE6 gene mutations (for example, the mutation of the human PDE6B gene corresponding to the Pde6b gene encoding the mouse PDE6β subunit) or PDE6 protein dysfunction (hereinafter collectively referred to as "diseases associated with PDE6 protein dysfunction"). Examples of retinitis pigmentosa include, but are not limited to, atypical retinitis pigmentosa, typical retinitis pigmentosa, and retinitis pigmentosa associated with systemic diseases. Examples of hereditary diseases involving photoreceptor cell degeneration include, but are not limited to, diseases other than retinitis pigmentosa, such as macular dystrophy. Examples of diseases associated with PDE6 protein dysfunction include, but are not limited to, achromatopsia, autosomal dominant congenital stationary night blindness, and retinitis pigmentosa. Also, the pharmaceutical composition of the present invention can be used as a photoreceptor cell degeneration inhibitor.

It can be confirmed that the pharmaceutical composition of the present invention can be used in the treatment or prevention of HTRA1-related diseases by, for example, observing an increase in the thickness of the outer nuclear layer of retina as compared with the control group when administering the HTRA1-inhibiting peptide of the present invention to Rd10 retinitis pigmentosa model mice (in which the Pde6b gene encoding the PDE6β subunit has a mutation) (Example 15). In addition, an increase in HTRA1 gene expression in a model animal having a rhodopsin gene mutation was correlated with photoreceptor cell degeneration (Example 16). The pharmaceutical composition of the present invention can be used in the treatment or prevention of retinitis pigmentosa, hereditary (not limited to the rhodopsin gene) diseases involving photoreceptor cell degeneration other than retinitis pigmentosa, and/or diseases associated with PDE6 protein dysfunction.

The HTRA1-inhibiting peptide of the present invention is excellent in terms of tissue penetration (Example 11) and also excellent in terms of its physical properties, stability, safety, kinetics after administration, productivity, etc. and can thus preferably be contained as an active ingredient in a pharmaceutical composition.

The pharmaceutical composition of the present invention can contain a therapeutically or prophylactically effective amount of the HTRA1-inhibiting peptide or the conjugate thereof and a pharmaceutically acceptable diluent, carrier, solubilizer, emulsifier, preservative and/or adjuvant.

The term "therapeutically or prophylactically effective amount" is used to mean an amount that exerts a therapeutic or prophylactic effect on a specific disease through a dosage form and an administration route, and is synonymous with a "pharmacologically effective amount".

The pharmaceutical composition of the present invention can contain a substance for altering, maintaining, or retaining pH, osmotic pressure, viscosity, transparency, color, isotonicity, sterility, or the stability, solubility, sustained release rate, absorptivity, penetration, dosage form, strength, properties, shape, etc. of the composition or the peptide of the present invention or the conjugate thereof contained therein (hereinafter, referred to as a "pharmaceutical substance"). The pharmaceutical substance is not particularly limited as long as the substance is pharmacologically acceptable. For example, no or low toxicity is a property preferably possessed by the pharmaceutical substance.

Examples of the pharmaceutical substance can include the following substances, but are not limited thereto: amino acids such as glycine, alanine, glutamine, asparagine, histidine, arginine, and lysine; antimicrobial agents; antioxidants such as ascorbic acid, sodium sulfate, and sodium bisulfite; buffers such as phosphate, citrate, or borate buffers, sodium bicarbonate, and Tris-HCl solutions; fillers such as mannitol and glycine; chelating agents such as ethylenediaminetetraacetic acid (EDTA); complexing agents such as caffeine, polyvinylpyrrolidine, β-cyclodextrin, and hydroxypropyl-β-cyclodextrin; bulking agents such as glucose, mannose, and dextrin; other hydrocarbons such as monosaccharides, disaccharides, glucose, mannose, and dextrin; coloring agents; flavor agents; diluents; emulsifiers; hydrophilic polymers such as polyvinylpyrrolidine; low-molecular-weight polypeptides; salt-forming counterions; antiseptics such as benzalkonium chloride, benzoic acid, salicylic acid, thimerosal, phenethyl alcohol, methylparaben, propylparaben, chlorhexidine, sorbic acid, and hydrogen peroxide; solvents such as glycerin, propylene glycol, and polyethylene glycol; sugar alcohols such as mannitol and sorbitol; suspending agents; surfactants such as PEG, sorbitan ester, polysorbates such as polysorbate 20 and polysorbate 80, triton, tromethamine, lecithin, and cholesterol; stability enhancers such as sucrose and sorbitol; elasticity enhancers such as sodium chloride, potassium chloride, mannitol, and sorbitol; transporting agents; diluents; excipients; and/or pharmaceutical adjuvants.

Such a pharmaceutical substance is added to the HTRA1-inhibiting peptide in an amount of 0.001 to 1000 times, preferably 0.01 to 100 times, and more preferably 0.1 to 10 times higher than the weight of the HTRA1-inhibiting peptide.

A liposome containing the HTRA1-inhibiting peptide or the conjugate thereof, or a pharmaceutical composition containing a modified form comprising the HTRA1-inhibiting peptide or the conjugate thereof conjugated with a liposome is also included within the pharmaceutical composition of the present invention.

An excipient or a carrier is not particularly limited as long as the excipient or the carrier is usually a liquid or a solid and is water for injection, normal saline, an artificial cerebrospinal fluid, or other substances for use in preparations for oral administration or parenteral administration. Examples of normal saline can include neutral normal saline or normal saline containing serum albumin.

Examples of the buffer can include a Tris buffer prepared to bring the final pH of the pharmaceutical composition to 7.0 to 8.5, an acetate buffer prepared to bring the final pH thereof to 4.0 to 5.5, a citrate buffer prepared to bring the final pH thereof to 5.0 to 8.0, and a histidine buffer prepared to bring the final pH thereof to 5.0 to 8.0.

The pharmaceutical composition of the present invention is a solid, a liquid, a suspension, or the like. Another example of the pharmaceutical composition of the present invention can include freeze-dried preparations. The freeze-dried preparations can be formed using an excipient such as sucrose.

The administration route of the pharmaceutical composition of the present invention may be any of ocular instillation, enteral administration, local administration, and parenteral administration. Examples thereof can include conjunctival instillation, intravitreal administration, intravenous administration, intraarterial administration, intramuscular administration, intradermal administration, subcutaneous administration, intraperitoneal administration, transdermal administration, intraosseous administration, and intraarticular administration.

The recipe of the pharmaceutical composition can be determined according to an administration method, the HTRA1 binding affinity of the HTRA1-inhibiting peptide, etc. An HTRA1-inhibiting peptide of the present invention having a stronger inhibitory activity (smaller $IC_{50}$ value) against the target HTRA1 or having a higher affinity (lower $K_D$ value) for the HTRA1 protein is capable of exerting its medicinal effects at a lower dose.

The dose of the HTRA1-inhibiting peptide of the present invention or the conjugate thereof is not limited as long as the dose is a pharmacologically effective amount. The dose can be appropriately determined according to the species of an individual, the type of disease, symptoms, sex, age, pre-existing conditions, the binding affinity of the peptide for the HTRA1 protein or its biological activity, and other factors. The dose is usually 0.01 to 1000 mg/kg, and preferably 0.1 to 100 mg/kg, which can be administered once every day to every 180 days or twice or three or more times a day.

Examples of the form of the pharmaceutical composition can include injections (including freeze-dried preparations and drip infusions), suppositories, transnasal absorption preparations, transdermal absorption preparations, sublingual agents, capsules, tablets, ointments, granules, aerosols, pills, powders, suspensions, emulsions, eye drops, and biological implant formulations.

The pharmaceutical composition comprising the HTRA1-inhibiting peptide or the conjugate thereof as an active ingredient can be administered concurrently with or separately from an additional medicament. For example, the pharmaceutical composition comprising the HTRA1-inhibiting peptide or the conjugate thereof as an active ingredient may be administered after administration of the additional medicament, or the additional medicament may be administered after administration of the pharmaceutical composition. Alternatively, the pharmaceutical composition and the additional medicament may be administered concurrently. For concurrent administration, the HTRA1-inhibiting peptide or the conjugate thereof and the additional medicament may be contained in a single preparation or may be contained in separate preparations (a plurality of preparations).

Examples of the additional medicament used in combination with the pharmaceutical composition of the present invention can include anti-VEGF agents, anti-inflammatory agents, inflammatory cytokine-neutralizing agents, and complement activation pathway inhibitors. The anti-VEGF agents are classified into anti-VEGF antibodies, VEGF inhibitors, VEGF receptor antagonists and soluble VEGF receptors, etc. and include bevacizumab, ranibizumab, aflibercept, pegaptanib, brolucizumab, and the like. The anti-inflammatory agent is not particularly limited as long as the anti-inflammatory agent can be locally administered in order to suppress intraocular or intraarticular inflammation. Examples of the inflammatory cytokine-neutralizing agent include anti-TNFα antibodies, anti-interleukin-6 (hereinafter, referred to as "IL-6") antibodies, anti-IL-6 receptor antibodies, and soluble TNF receptors and can specifically include infliximab, adalimumab, golimumab, certolizumab, tocilizumab, and etanercept. Examples of the complement activation pathway inhibitor can include lampalizumab. These medicaments are suitable for the treatment or prevention of HTRA1-related diseases and can also be combined with the pharmaceutical composition of the present invention in the treatment or prevention of diseases other than HTRA1-related diseases.

One of these additional medicaments may be used, or two or three or more thereof may be administered or received. These approaches are collectively referred to as "combined use with the additional medicament" of or "combination with the additional medicament" and the pharmaceutical composition of the present invention. The pharmaceutical composition of the present invention comprising the additional medicament in addition to the antibody of the present invention, a binding fragment thereof, or a modified form of the antibody or the fragment, or used in combination with additional therapy is also included within the present invention as an aspect of the "combined use with the additional medicament" or the "combination with the additional medicament".

The present invention also provides a method for the treatment or prevention of a HTRA1-related disease such as retinitis pigmentosa, comprising the step of administering the HTRA1-inhibiting peptide or the conjugate thereof, use of the HTRA1-inhibiting peptide of the present invention or the conjugate thereof for preparing a pharmaceutical composition for the treatment or prevention of the disease, and use of the HTRA1-inhibiting peptide or the conjugate thereof for the treatment or prevention of the disease. The present invention also includes a kit for treatment or prevention comprising the HTRA1-inhibiting peptide of the present invention or the conjugate thereof.

The present invention further provides a polynucleotide comprising a nucleotide sequence encoding the amino acid sequence of the HTRA1-inhibiting peptide or the conjugate thereof, a vector comprising the polynucleotide, and a pharmaceutical composition comprising the polynucleotide or the vector or comprising a cell expressing the HTRA1-inhibiting peptide of the present invention or the conjugate thereof. For example, the polynucleotide and the vector can be applied to the gene therapy of HTRA1-related diseases by use of a known approach. The cell can be applied to the cell therapy of HTRA1-related diseases by use of a known approach. Also, the polynucleotide or the vector can be transferred to, for example, autologous cells or allogeneic cells (homologous cells) to prepare cells for cell therapy. Such a polynucleotide and vector are also included as compositions for cell therapy drug preparation in the present invention. However, the form of the pharmaceutical composition of the present invention comprising the polynucleotide, the vector, the cell, or the like is not limited to those described above.

6. Composition for Diagnosis and Detection of HTRA1

The HTRA1-inhibiting peptide of the present invention or the conjugate thereof may have HTRA1 binding activity in addition to HTRA1 protease inhibitory activity and can be used in various studies such as use as a positive control in studies to search for HTRA1 inhibitors, the detection of HTRA1, examination and diagnosis using the detection, the separation of HTRA1, reagents and other purposes. For the detection or separation of HTRA1, at least one of the peptide of the present invention and HTRA1 can be immobilized.

The present invention provides a composition for detection or for diagnosis (hereinafter, collectively referred to as a "composition for diagnosis") comprising the peptide of the present invention which binds to HTRA1, or the conjugate thereof.

The composition for diagnosis of the present invention is useful in the examination or diagnosis of HTRA1-related diseases, HTRA1 expression, etc. In the present invention, examples of the examination or the diagnosis include, but are not limited to, the determination or measurement of the risk of acquiring a disease, the determination of the presence or absence of a disease, the measurement of the degree of progression or exacerbation, the measurement or determination of the effect of medication with a pharmaceutical composition comprising the HTRA1-inhibiting peptide or the conjugate thereof, the measurement or determination of the effect of treatment other than medication, the measurement of the risk of recurrence, and the determination of the presence or absence of recurrence.

The composition for diagnosis of the present invention is useful in the identification of a recipient individual for the peptide of the present invention or the conjugate thereof, a composition comprising the peptide or the conjugate thereof, or a pharmaceutical composition comprising the peptide or the conjugate thereof.

The composition for diagnosis can contain a pH buffer, an osmotic pressure adjuster, salts, a stabilizer, an antiseptic, a developer, a sensitizer, an aggregation prevention agent, and the like.

The present invention also provides a method for examining or diagnosing a HTRA1-related disease, use of the peptide of the present invention for preparing a composition for the diagnosis of the disease, and use of the peptide of the present invention which binds to HTRA1, or the conjugate thereof for the examination or diagnosis of the disease. The present invention also includes a kit for examination or diagnosis comprising the peptide of the present invention or the conjugate thereof.

The examination or diagnosis method comprising the peptide of the present invention which binds to HTRA1 is desirably sandwich ELISA. Alternatively, a usual detection method such as ELISA, RIA, ELISPOT, dot blot, an Ouchterlony method, CIE, CLIA, or flow cytometry may be used. The examination or the diagnosis is also achieved by a method based on an immunoprecipitation method.

The present invention also provides a method for detecting or measuring HTRA1 in a test sample. Such a detection or measurement method can employ the composition for diagnosis of the present invention. HTRA1 in a test sample can be detected by: contacting the HTRA1-inhibiting peptide or the conjugate thereof with the test sample (step 1); and subsequently measuring the amount of HTRA1 bound to the peptide (step 2). Step 1 can involve, for example, immobilizing a conjugate of the HTRA1-inhibiting peptide with an immunoglobulin Fc region onto magnetic beads via protein G, and adding the test sample thereto. Step 2 can involve, for example, separating the magnetic beads, and analyzing a soluble protein precipitated with the beads by SDS-PAGE or Western blot to detect HTRA1. In addition to a human- or nonhuman animal-derived sample, even an artificially treated sample such as a recombinant protein can be subjected to this measurement. Examples of test samples derived from individual organisms can include, but are not limited to, blood, synovial fluid, ascitic fluid, lymph, cerebrospinal fluid, bronchoalveolar lavage, saliva, sputum, tissue homogenate supernatants, and tissue sections.

The HTRA1 detection can be carried out not only in vitro but in vivo. In the case of diagnostic imaging, the HTRA1-inhibiting peptide or the conjugate thereof labeled with a pharmaceutically acceptable radionuclide or light emitter can be used. Step 1 can involve, for example, administering the labeled peptide or conjugate thereof to a test subject. Step 2 can involve, for example, obtaining an image by use of a diagnostic imaging technique such as PET/CT, and determining or examining the presence of HTRA1.

The peptide or the conjugate thereof contained in the composition for diagnosis of the present invention binds to HTRA1, and preferably has HTRA1-specific binding activity.

The present invention also includes a method for identifying a recipient individual for the pharmaceutical composition of the present invention. In such an identification method, HTRA1 in a sample derived from an individual is measured using the HTRA1-binding peptide of the present invention, and the individual can be determined to be positive when HTRA1 is detected in the sample or when a larger amount of HTRA1 is detected therein as compared with the amount of HTRA1 detected in a sample derived from a healthy individual. This method can employ the composition for diagnosis of the present invention.

In a preferred aspect of the identification method, the individual has a HTRA1-related disease or has a risk of acquiring the disease.

In an aspect, the pharmaceutical composition of the present invention can be administered to the individual determined to be positive in the identification method.

HTRA1 can be specifically separated from a sample in which the HTRA1 coexists with other components, using the peptide of the present invention having HTRA1-specific binding activity, or the conjugate thereof. The release of the HTRA1 from the peptide can be nonselectively performed, for example, in the presence of relatively high ionic strength, low pH, moderate denaturation conditions, or chaotropic salt, and is preferably performed without attenuating the protease activity of the HTRA1.

7. Method for Identifying Therapeutic Drug or Prophylactic Drug for HTRA1-Related Disease In an aspect, the present invention provides a method for identifying a therapeutic drug or a prophylactic drug for a HTRA1-related disease, and preferably retinitis pigmentosa, hereditary diseases involving photoreceptor cell degeneration other than retinitis pigmentosa, and/or diseases associated with PDE6 protein dysfunction, or a candidate thereof by using HTRA1 inhibitory activity as an indicator. The method can comprise: step 1 of incubating HTRA1 protease and a substrate in the presence or absence of a test substance (or in the presence of a vehicle); step 2 of determining HTRA1 protease activity in the presence and absence of the test substance; and/or step 3 of determining the test substance as a therapeutic drug or a prophylactic drug for retinitis pigmentosa, hereditary diseases involving photoreceptor cell degeneration other than retinitis pigmentosa, and/or diseases associated with PDE6 protein dysfunction, or a candidate thereof when the HTRA1 protease activity in the presence of the test substance is lower than the HTRA1 protease activity in the absence of the test substance. The test substance may be peptidic or nonpeptidic. The peptidic test substance is not limited to SPINK2 mutants. Examples thereof can include, but are not limited to, antibodies, peptides other than SPINK2 mutants having a non-immunoglobulin protein framework, and HTRA1 substrate analogs. Examples of the nonpeptidic test substance can include, but are not limited to, synthetic low-molecular compounds and nucleic acids. One or two or more of the steps described above can also be preferably included in a method for identifying a substance having a suppressive effect on photoreceptor cell degeneration, or a candidate thereof. The present invention also relates to a method for identifying a substance having a suppressive effect on photoreceptor cell degeneration, or a candidate thereof.

EXAMPLES

Hereinafter, some aspects of the present invention will be described in more detail with reference to Examples. However, the present invention is not limited to these examples.

In the following examples, unless otherwise specified, individual operations regarding genetic manipulation have been carried out according to the method described in "Molecular Cloning" (Sambrook, J., Fritsch, E. F. and Maniatis, T., published by Cold Spring Harbor Laboratory Press in 1982 or 1989) or other methods described in experimental manuals used by persons skilled in the art, or, when commercially available reagents or kits have been used, the examples have been carried out in accordance with the instructions included in the commercially available products.

Example 1. Preparation of HTRA1-Inhibiting Peptide (1-1) Construction of HTRA1-Inhibiting Peptide Expression Vector (1-1-1) Construction of pET 32a (Modified)_HTRA1-Inhibiting Peptide First, a HTRA1-inhibiting peptide expression vector with a SPINK2 scaffold as a backbone was constructed. An inhibitor fragment was amplified by PCR ((94° C. for 15 sec, 60° C. for 30 sec, and 68° C. for 30 sec)×30 cycles) with the nucleotide sequence (SEQ ID NOs: 4, 6, 8, 10, 12, 14, 16, 18, 20 and 22) of each inhibiting peptide and the nucleotide sequence (SEQ ID NO: 2) of SPINK2 as templates using the following primers and KOD-plus-(Toyobo Co., Ltd.).

```
Primer 1:
                                (SEQ ID NO: 33)
5'-AAAAGAATTCTGATCCGCAGTTTGGTCTGTTTAG-3'

Primer 2:
                                (SEQ ID NO: 34)
5'-AAAACTCGAGTTATGCGGCCGCAGACGCGCCGCACGGACC-3'
```

Each amplified fragment was subjected to agarose gel electrophoresis. Then, the desired DNA fragment was excised from the gel, and DNA was prepared using a QIAquick Gel Extraction Kit (Qiagen N. V.). The prepared DNA fragment and pET 32a (modified) were each treated with restriction enzymes EcoRI (New England BioLabs Inc.) and XhoI (New England BioLabs Inc.) at 37° C. for 1 hour or longer. After agarose gel electrophoresis, the desired DNA fragments were excised from the gel and purified using a QIAquick PCR Purification Kit (Qiagen N.V.). The purified fragments were reacted overnight at 16° C. for a ligation reaction using T4 DNA Ligase (New England BioLabs Inc.). The ligation solution was added to *E. coli* JM109 (Toyobo Co., Ltd.), and the mixture was left standing on ice for 30 minutes, then heat-treated at 42° C. for 45 seconds, further left standing on ice for 5 minutes, and inoculated onto a 2YT plate containing 0.1 mg/ml ampicillin, followed by static culture overnight at 37° C. to transform the *E. coli*. On the next day, the transformed *E. coli* was inoculated to a Terrific Broth medium (Invitrogen Corp.) containing 0.1 mg/ml ampicillin and cultured overnight at 37° C. Then, plasmid DNA was recovered using a QIAprep 96 Turbo Miniprep Kit (Qiagen N.V.) (hereinafter, this treatment is referred to as "miniprep treatment") and subjected to sequence analysis to construct "pET 32a (modified)_HTRA1-inhibiting peptide".

(1-1-2) Construction of pET 32a_HTRA1-Inhibiting Peptide_Kex2

Likewise, an inhibitor fragment was amplified by PCR ((94° C. for 15 sec, 60° C. for 30 sec, and 68° C. for 30 sec)×30 cycles) with the sequence (Sequence Listing) of each inhibitor and the nucleotide sequence of SPINK2 as templates using the following primers and KOD-plus-(Toyobo Co., Ltd.).

```
Primer 3:
                                (SEQ ID NO: 35)
5'-AAAAGGATCCCTGGACAAACGTGATCCGCAGTTTGGTCTGTT
TAG-3'

Primer 4:
                                (SEQ ID NO: 36)
5'-AAAACTCGAGTTAGCCGCCGCACGGACCATTGCGAATAATTT
TA-3'
```

Each amplified fragment was subjected to agarose gel electrophoresis. Then, the desired DNA fragment was excised from the gel, and DNA was prepared using a QIAquick Gel Extraction Kit (Qiagen N.V.). The prepared DNA fragment and pET 32a (Novagen) were each treated with restriction enzymes BamHI (New England BioLabs Inc.) and XhoI (New England BioLabs Inc.) at 37° C. for 1 hour or longer. After agarose gel electrophoresis, the desired DNA fragments were excised from the gel and purified using a QIAquick PCR Purification Kit (Qiagen N.V.). The purified fragments were reacted overnight at 16° C. for a ligation reaction using T4 DNA Ligase (New England BioLabs Inc.). The ligation solution was added to *E. coli* JM109 (Toyobo Co., Ltd.), and the mixture was left standing on ice for 30 minutes, then heat-treated at 42° C. for 45 seconds, further left standing on ice for 5 minutes, and inoculated onto a 2YT plate containing 0.1 mg/ml ampicillin, followed by static culture overnight at 37° C. to transform the *E. coli*. The transformed *E. coli* was cultured, and miniprep and sequence analysis were then carried out to construct "pET 32a_HTRA1-inhibiting peptide_Kex2". The operation was performed in accordance with the method described in (1-1-1).

(1-2) Expression and Purification of HTRA1-Inhibiting Peptide

*E. coli* Origami B (DE3) (Novagen) was transformed with the vector pET 32a (modified)_HTRA1-inhibiting peptide constructed in (1-1-1), and cultured at 37° C. using a 2YT medium containing 0.1 mg/ml ampicillin. Then, IPTG (final concentration: 1 mM) was added thereto, and the *E. coli* was cultured overnight at 16° C. On the next day, after harvest by centrifugation (3,000 g, 20 min, 4° C.), a lysate was prepared using BugBuster Master Mix (Novagen), and a His tag fusion protein of interest was purified using a TALON Metal Affinity Resin (Clontech Laboratories, Inc.). Next, a thioredoxin tag and the desired protein were cleaved using a Thrombin Cleavage Capture Kit (Novagen) and purified using TALON. The resultant was subjected to gel filtration chromatography (Superdex 75 10/300 GL) or reverse-phase chromatography (YMC-Pack ODS-AM) to prepare a HTRA1-inhibiting peptide. The obtained peptide was conjugated at its N terminus with a moiety consisting of S tag and a linker (SEQ ID NO: 31: FIG. 43) and at its C terminus with a C-terminal hexamer (SEQ ID NO: 32: FIG. 44) instead of Gly-Gly.

Likewise, *E. coli* Origami B (DE3) (Novagen) was transformed with the vector pET 32a_HTRA1-inhibiting peptide_Kex2 constructed in (1-1-2), and cultured at 37° C. using a 2YT medium containing 0.1 mg/ml ampicillin. Then, IPTG (final concentration: 1 mM) was added thereto, and the *E. coli* was cultured overnight at 16° C. On the next day, after harvest by centrifugation (3,000 g, 20 min, 4° C.), a lysate was prepared using BugBuster Master Mix (Novagen), and a His tag fusion protein of interest was purified using a TALON Metal Affinity Resin (Clontech Laboratories, Inc.). Next, a thioredoxin tag and the desired protein were cleaved using Kex2 (*Saccharomyces cerevisiae*: Accession CAA96143) and purified using TALON. The resultant was subjected to gel filtration chromatography (Superdex 75 10/300 GL) or reverse-phase chromatography (YMC-Pack ODS-AM) to prepare a HTRA1-inhibiting peptide (with neither the N terminus nor the C terminus conjugated with a tag, a linker or the like).

Figure 1A:
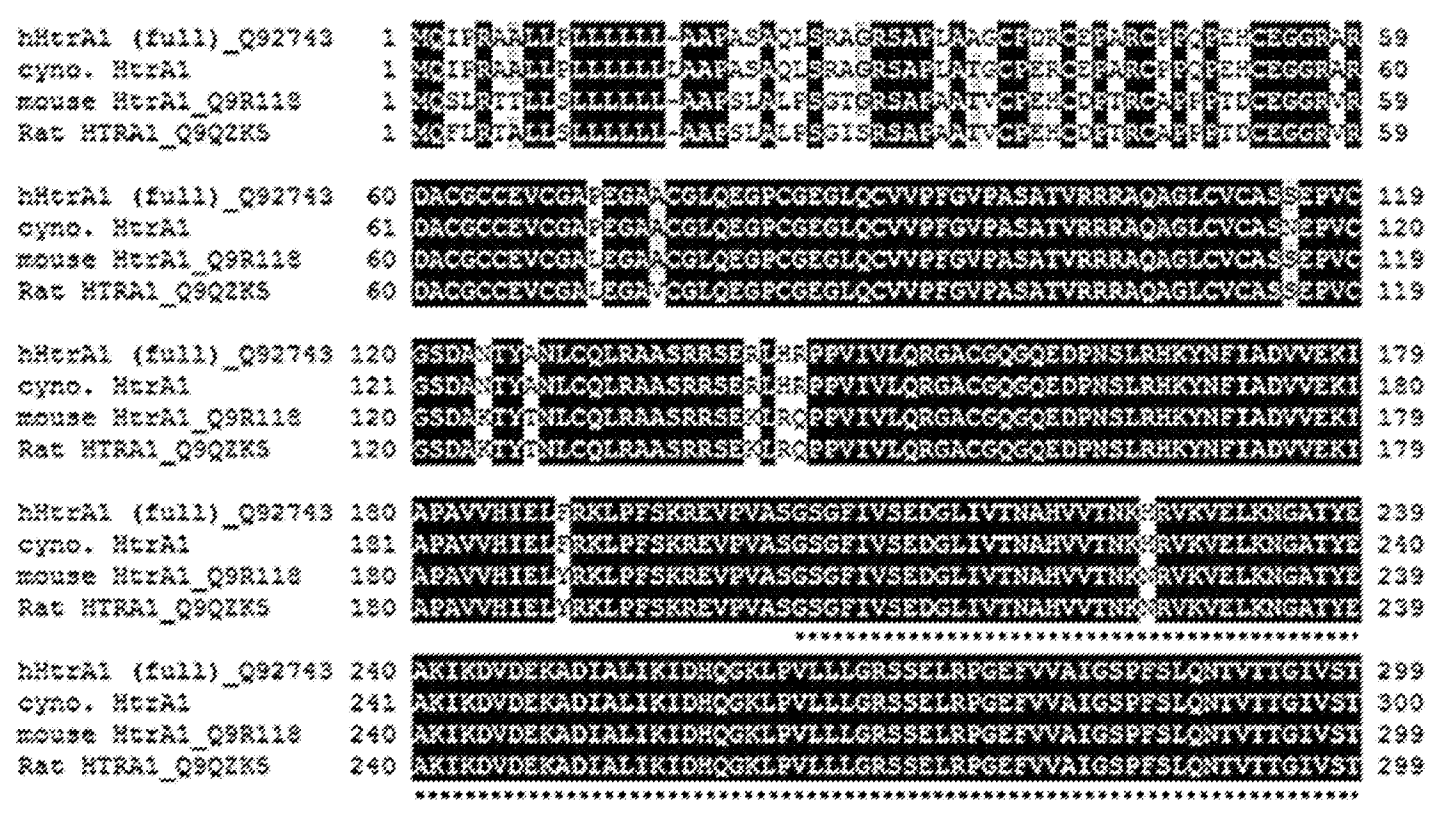
Figure 1B:
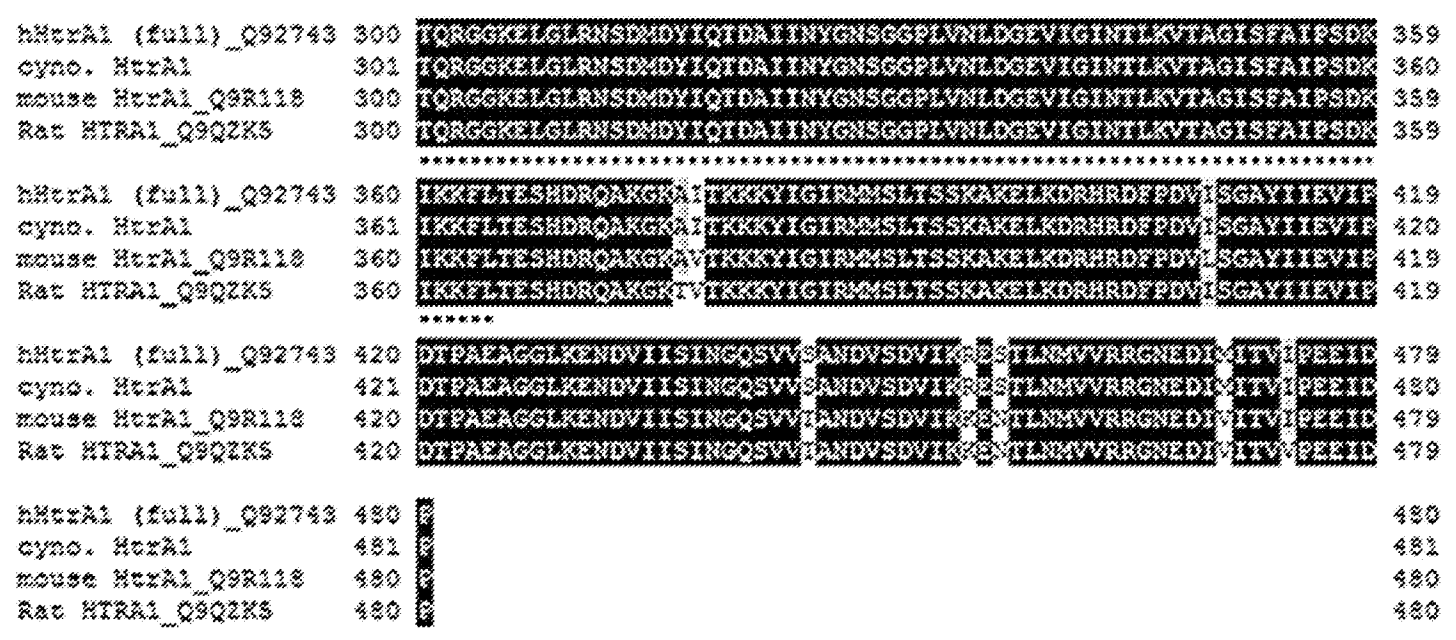

Example 2. Evaluation of HTRA1-Inhibiting Peptide for HTRA1 Inhibitory Activity Sequence similarity among human, mouse, rat, and monkey HTRA1 is shown in FIG. 1. A primary sequence constituting a HTRA1 protease domain (204Gly to 364Leu), which is an enzymatically active domain, is completely identical between the human and the monkey. The human and mouse or rat HTRA1 protease domain sequences differ by 1 residue. However, this residue is structurally positioned on a side opposite to the active center of the enzyme and was therefore presumed to have no influence on the active center of the enzyme (FIG. 1). Accordingly, the HTRA1 protease domain has effectively the same sequence, regardless of the species (human/mouse/rat/monkey). Thus, no particular mention was made about the species.

(2-1) Preparation of HTRA1 Protease Domain HTRA1 (Cat)

(2-1-1) Construction of pET 21b_HTRA1 (Cat)

The protease domain (158Gly to 373Lys), which excludes the N-terminal domain and the PDZ domain, of human HTRA1 (Q92743) was used as HTRA1 (cat) to construct a HTRA1 (cat) expression vector. The desired DNA fragment was amplified by PCR ((94° C. for 15 sec, 60° C. for 30 sec, and 68° C. for 45 sec)×30 cycles) with a human HTRA1-inserted plasmid (GeneCopoeia, Inc.; GC-M0558) as a template using the following primers and KOD-plus-(Toyobo Co., Ltd.).

```
Primer 5:
                            (SEQ ID NO: 37)
5'-AAACATATGGGGCAGGAAGATCCCAACAGTTTGC-3'

Primer 6:
                            (SEQ ID NO: 38)
5'-AAACTCGAGTTTGGCCTGTCGGTCATGGGACTC-3'
```

The amplified fragment was subjected to agarose gel electrophoresis. Then, the desired DNA fragment was excised from the gel, and DNA was prepared using a QIAquick Gel Extraction Kit (Qiagen N.V.). The prepared DNA fragment and pET 32a (Novagen) were each treated with restriction enzymes NdeI (New England BioLabs Inc.) and XhoI (New England BioLabs Inc.) at 37° C. for 1 hour or longer. After agarose gel electrophoresis, the desired DNA fragments were excised from the gel and purified using a QIAquick PCR Purification Kit (Qiagen N.V.). The purified fragments were reacted overnight at 16° C. for a ligation reaction using T4 DNA Ligase (New England BioLabs Inc.). The ligation solution was added to E. coli JM109 (Toyobo Co., Ltd.), and the mixture was left standing on ice for 30 minutes, then heat-treated at 42° C. for 45 seconds, further left standing on ice for 5 minutes, and inoculated onto a 2YT plate containing 0.1 mg/ml ampicillin, followed by static culture overnight at 37° C. to transform the E. coli. The transformed E. coli was cultured, and miniprep and sequence analysis were then carried out to construct "pET 21b_HTRA1 (cat)". The operation was performed in accordance with the method described in (1-1-1).

(2-1-2) Preparation of HTRA1 (Cat)

E. coli BL21 (DE3) (Novagen) was transformed with the constructed pET 21b_HTRA1 (cat) and cultured at 37° C. using a 2YT medium containing 0.1 mg/ml ampicillin. Then, IPTG (final concentration: 1 mM) was added thereto, and the E. coli was cultured overnight at 28° C. After harvest, a lysate was prepared by suspending in a phosphate buffer (50 mM sodium phosphate and 300 mM NaCl) containing 1 mg/ml lysozyme and ultrasonication, and the desired His tag fusion protein was recovered using TALON (Clontech Laboratories, Inc.). The resultant was subjected to gel filtration chromatography (Superdex 200 10/300 GL) to purify HTRA1 (cat).

(2-2) Preparation of Full-Length HTRA1 (HTRA1 (Full))

(2-2-1) Construction of pcDNA3.1_HTRA1 (Full)_His

The desired DNA fragment was amplified by PCR ((94° C. for 15 sec, 60° C. for 30 sec, and 68° C. for 90 sec)×30 cycles) with synthesized human HTRA1 (Q92743) DNA (GeneArt) as a template using the following primers and KOD-plus-(Toyobo Co., Ltd.).

```
Primer 7:
                            (SEQ ID NO: 39)
5'-AAAAGAATTCGCCACCATGCAGATTCCTAGAGCCG-3'

Primer 8:
                            (SEQ ID NO: 40)
5'-AAAACTCGAGTCAGTGGTGATGGTGGTGGTGGCCGG-3'
```

The amplified fragment was subjected to agarose gel electrophoresis. Then, the desired DNA fragment was excised from the gel, and DNA was prepared using a QIAquick Gel Extraction Kit (Qiagen N.V.). The prepared DNA fragment and pcDNA3.1 (Thermo Fisher Scientific Inc.) were each treated with restriction enzymes EcoRI (New England BioLabs Inc.) and XhoI (New England BioLabs Inc.) at 37° C. for 1 hour or longer. After agarose gel electrophoresis, the desired DNA fragments were excised from the gel and purified using a QIAquick PCR Purification Kit (Qiagen N.V.). The purified fragments were reacted overnight at 16° C. for a ligation reaction using T4 DNA Ligase (New England BioLabs Inc.). The ligation solution was added to E. coli JM109 (Toyobo Co., Ltd.), and the mixture was left standing on ice for 30 minutes, then heat-treated at 42° C. for 45 seconds, further left standing on ice for 5 minutes, and inoculated onto a 2YT plate containing 0.1 mg/ml ampicillin, followed by static culture overnight at 37° C. to transform the E. coli. The transformed E. coli was cultured, and miniprep and sequence analysis were then carried out to construct "pcDNA3.1_HTRA1 (full)_His". The operation was performed in accordance with the method described in (1-1-1).

(2-2-2) Construction of pcDNA3.3_HTRA1 (Full)_FLAG_His

Fragment A was amplified by PCR ((94° C. for 15 sec, 60° C. for 30 sec, and 68° C. for 90 sec)×30 cycles) with pcDNA3.1_HTRA1 (full)_His constructed in (2-2-1) as a template using the following primers and KOD-plus-(Toyobo Co., Ltd.).

```
Primer 7

Primer 9:
                            (SEQ ID NO: 41)
5'-CTTGTCGTCATCGTCCTTGTAGTCGCCGGGGTCGATTTCCTC-3'
```

Next, fragment B was amplified by PCR ((94° C. for 15 sec, 60° C. for 30 sec, and 68° C. for 10 sec)×30 cycles) using the following primers and KOD-plus-(Toyobo Co., Ltd.).

```
Primer 10:
                            (SEQ ID NO: 42)
5'-GCGACTACAAGGACGATGACGACAAGCACCACCACCATCATCAC-3'

Primer 11:
                            (SEQ ID NO: 43)
5'-AAAAACTCGAGCTAGTGATGATGGTGGTGGTGCTTGTCGTC-3'
```

The desired DNA fragment was amplified by PCR ((94° C. for 15 sec, 60° C. for 30 sec, and 68° C. for 90 sec)×30 cycles) with fragment A and fragment B as templates using primers 7 and 11 and KOD-plus-(Toyobo Co., Ltd.). The amplified fragment was subjected to agarose gel electrophoresis. Then, the desired DNA fragment was excised from the gel, and DNA was prepared using a QIAquick Gel Extraction Kit (Qiagen N.V.). The prepared DNA fragment and pcDNA3.3 (Thermo Fisher Scientific Inc.) were each treated with restriction enzymes EcoRI (New England BioLabs Inc.) and XhoI (New England BioLabs Inc.) at 37° C. for 1 hour or longer. After agarose gel electrophoresis, the desired DNA fragments were excised from the gel and purified using a QIAquick PCR Purification Kit (Qiagen N.V.). The purified fragments were reacted overnight at 16° C. for a ligation reaction using T4 DNA Ligase (New England BioLabs Inc.). The ligation solution was added to *E. coli* JM109 (Toyobo Co., Ltd.), and the mixture was left standing on ice for 30 minutes, then heat-treated at 42° C. for 45 seconds, further left standing on ice for 5 minutes, and inoculated onto a 2YT plate containing 0.1 mg/ml ampicillin, followed by static culture overnight at 37° C. to transform the *E. coli*. The transformed *E. coli* was cultured, and miniprep and sequence analysis were then carried out to construct "pcDNA3.3_HTRA1 (full)_FLAG_His". The operation was performed in accordance with the method described in (1-1-1).

(2-2-3) Preparation of HTRA1 (Full)

FreeStyle 293F (Thermo Fisher Scientific Inc.) was transfected with pcDNA3.3_HTRA1 (full)_FLAG_His constructed in (2-2-2) using Polyethylenimine Max (Polysciences, Inc.). Six days later, a culture supernatant was recovered. A His tag fusion protein was recovered using HisTrap excel (GE Healthcare), and HTRA1 (full) was further purified using an ANTI-FLAG M2 Affinity Agarose Gel (Sigma-Aldrich Co. LLC).

(2-3) Preparation of Inactive HTRA1 Mutant HTRA1 (S328A)

(2-3-1) Construction of pcDNA3.3_HTRA1(S328A)_FLAG_His

In order to construct an inactive HTRA1 mutant HTRA1 (S328A) expression vector, PCR ((95° C. for 30 sec, 55° C. for 1 min, and 68° C. for 7 min)×18 cycles) was carried out with the vector "pcDNA3.3_HTRA1 (full)_FLAG_His" constructed in Example (2-2-2) as a template using the following primers and QuikChange II Site-Directed Mutagenesis Kits (Agilent Technologies Japan, Ltd.).

Primer 21:
5'-CCATCATCAACTACGGCAACGCGGGCGGACCCCTCGTGAACC-3'

(SEQ ID NO: 55: FIG. 76)

Primer 22:
5'-GGTTCACGAGGGGTCCGCCCGCGTTGCCGTAGTTGATGATGG-3'

(SEQ ID NO: 56: FIG. 77)

After the PCR reaction, *E. coli* JM109 (Toyobo Co., Ltd.) was transformed with the PCR reaction solution treated with DpnI according to the protocol attached to the kit. The transformed *E. coli* was cultured, and miniprep and sequence analysis were then carried out to construct "pcDNA3.3_HTRA1(S328A)_FLAG_His". The operation was performed in accordance with the method described in (1-1-3).

(2-3-2) Preparation of HTRA1 (S328A)

HTRA1 (S328A) was expressed using FreeStyle 293F according to the method described in (2-2-3), and HTRA1 (S328A) was prepared by affinity purification.

Figure 8:
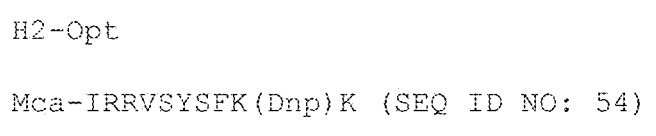

Example 3. Evaluation of HTRA1-Inhibiting Peptide for HTRA1 Inhibitory Activity (3-1) Evaluation of HTRA1-Inhibiting Peptide for HTRA1 Inhibitory Activity Using Peptide Substrate A substrate peptide H2-Opt (Mca-IRRVSYSFK(Dnp)K) (SEQ ID NO:66) (Peptide Institute, Inc.: SEQ ID NO: 54, FIG. 8) was dissolved at 10 mM in DMSO, diluted with an assay buffer (50 mM borate and 150 mM NaCl, pH 8.5), and used at a final concentration of 10 µM. HTRA1 (HTRA1 (cat) or HTRA1 (full)) and each HTRA1-inhibiting peptide diluted with an assay buffer were mixed at 25 µL each and reacted at 37° C. for 20 minutes. Then, 50 µL of the substrate diluted with an assay buffer was added thereto. A fluorescent signal (excitation at 328 nm/emission at 393 nm) was measured using Enspire (PerkinElmer, Inc.). The final concentration of HTRA1 was 100 nM, and the final concentration of the HTRA1-inhibiting peptide was 1.875 to 1,000 nM. PROTEOSAV® SS96F black plate (Sumitomo Bakelite Co., Ltd.) was used in the reaction and the measurement.

The substrate peptide decomposition rate of the HTRA1-inhibiting peptide at each concentration was calculated. When the decomposition rate at an inhibitor concentration of 0 nM was defined as 100%, the HTRA1 (cat) and HTRA1 (full) inhibitory activity of each HTRA1-inhibiting peptide was evaluated (FIGS. 2 and 3). As a result of calculating a 50% inhibitory concentration (IC50) using GraphPad Prism (version 5.0; GraphPad Software Inc.), all the HTRA1-inhibiting peptides were found to inhibit HTRA1 (cat) and HTRA1 (full) enzyme activity at a low concentration (FIGS. 2A to 2C and FIG. 3). By control, wild-type SPINK2 (wt) exhibited no HTRA1 inhibitory activity (FIG. 2D).

TABLE 1

HTRA1 inhibitory activity of each HTRA1-inhibiting peptide

| ID | IC50 (nM) for HTRA1 (cat) | IC50 (nM) for HTRA1 (full) |
|---|---|---|
| H218 | 72 | 55 |
| H223 | 41 | 66 |
| H228 | 71 | 38 |
| H308 | 37 | 15 |
| H321 | 48 | 29 |
| H322 | 50 | 17 |
| H308AT | 49 | 31 |
| H321AT | 46 | 18 |
| H322AT | 45 | 25 |
| M7 | 43 | 24 |

(3-2) Evaluation of HTRA1-Inhibiting Peptide for HTRA1 Inhibitory Activity Using Protein Substrate The HTRA1 inhibitory activity of a HTRA1-inhibiting peptide was evaluated with human vitronectin as a protein substrate. HTRA1 (cat) and each HTRA1-inhibiting peptide diluted with an assay buffer (50 mM Tris and 150 mM NaCl, pH 8.0) were mixed and reacted at 37° C. for 1 hour. Next, human vitronectin (BD Biosciences; 354238) diluted with an assay buffer was added thereto and reacted at 37° C. for 2 hours. A SDS sample buffer was added thereto, and the enzyme reaction was terminated by treatment at 99° C. for 5 minutes. Then, the decomposition of the human vitronectin was evaluated by SDS-PAGE and Western blot analysis. The final concentration of the HTRA1-inhibiting peptide was 0 to 25 µM, the final concentration of HTRA1 (cat) was 1 µM, and the final concentration of the human vitronectin was 1 M. For the Western blot analysis, Human Vitronectin Antibody (R&D Systems, Inc.; MAB2349) was used as a primary antibody, and Anti-Mouse IgG, HRP-Linked Whole Ab Sheep (GE Healthcare; NA931) was used as a secondary antibody.

Figure 4B:
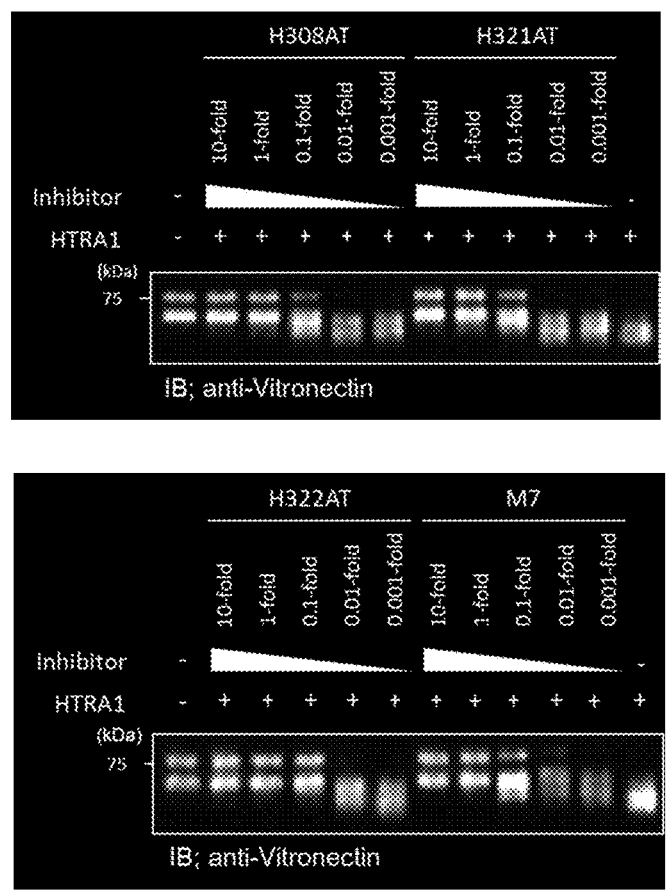
FIG. 4(B) is a diagram showing the results of evaluating the HTRA1 (cat) inhibitory activity of a HTRA1-inhibiting peptide by using the decomposition of human vitronectin as an indicator (Cont.).
Figure 5A:
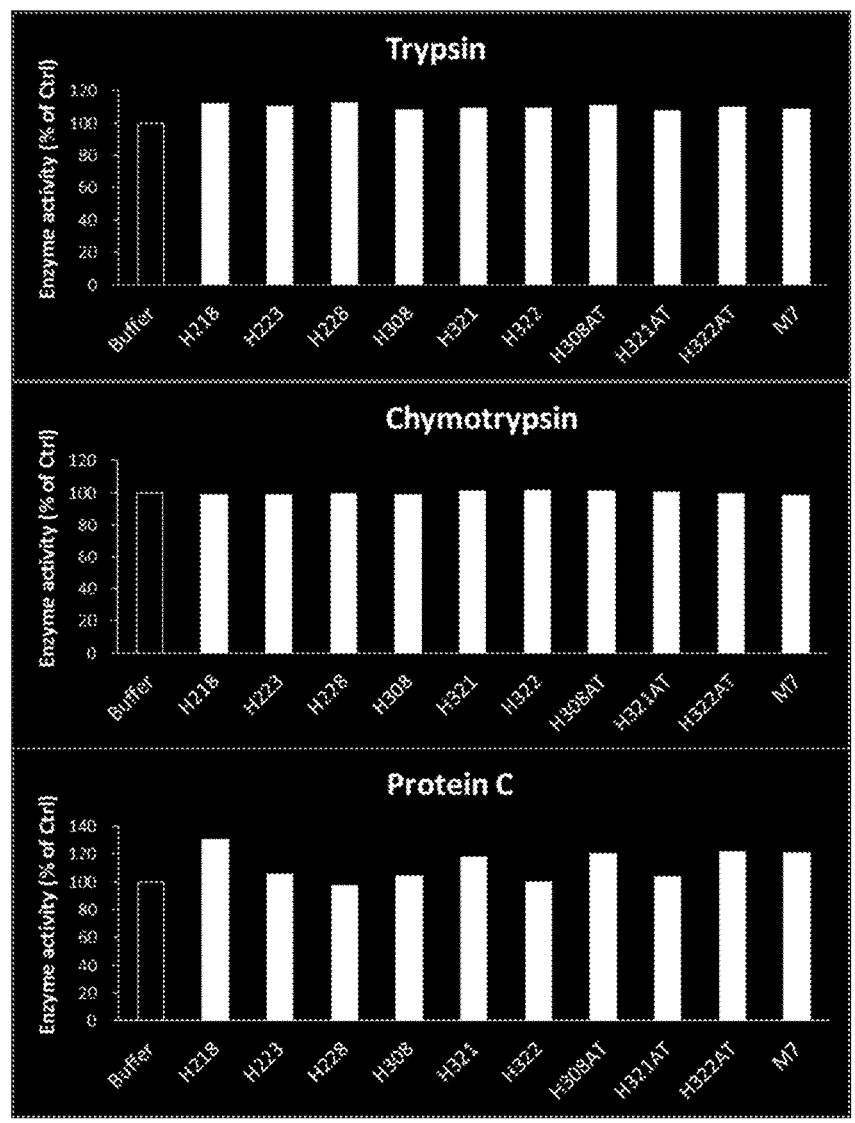
FIG. 5(A) is a diagram showing the results of evaluating the cross-reactivity of a HTRA1-inhibiting peptide with each protease by using the decomposition of a peptide substrate as an indicator (part 1). For the name of each protease used and its concentration and the name of the substrate and its concentration, etc., see Example 3.
Figure 5B:
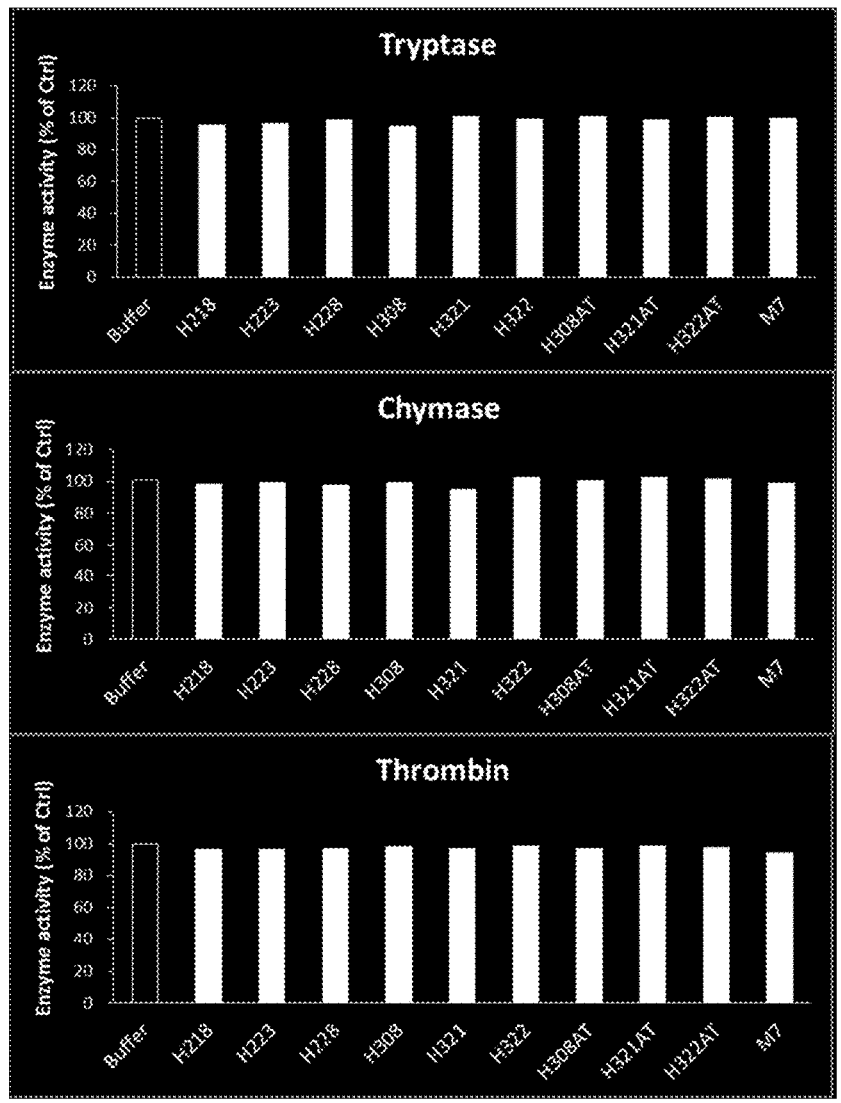
FIG. 5(B) is a diagram showing the results of evaluating the cross-reactivity of a HTRA1-inhibiting peptide with each protease by using the decomposition of a peptide substrate as an indicator (part 2).
Figure 5C:
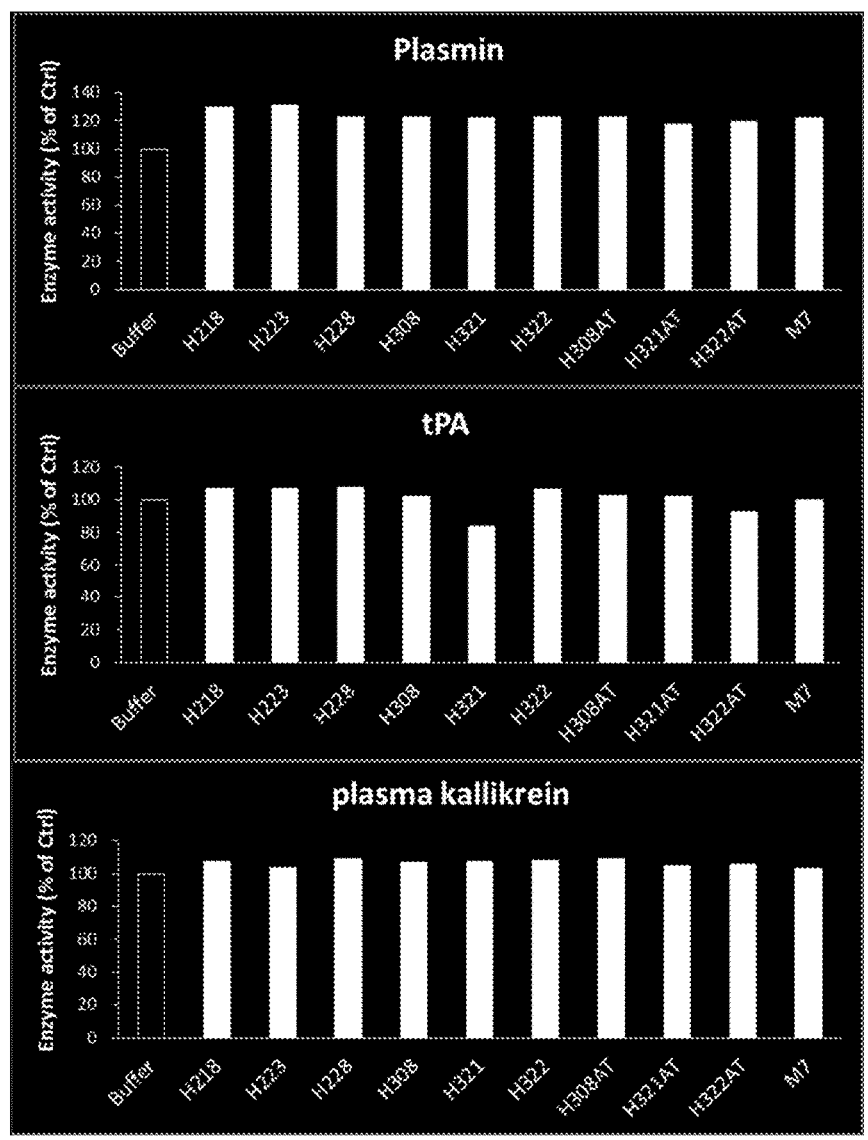
FIG. 5(C) is a diagram showing the results of evaluating the cross-reactivity of a HTRA1-inhibiting peptide with each protease by using the decomposition of a peptide substrate as an indicator (part 3).
Figure 5D:
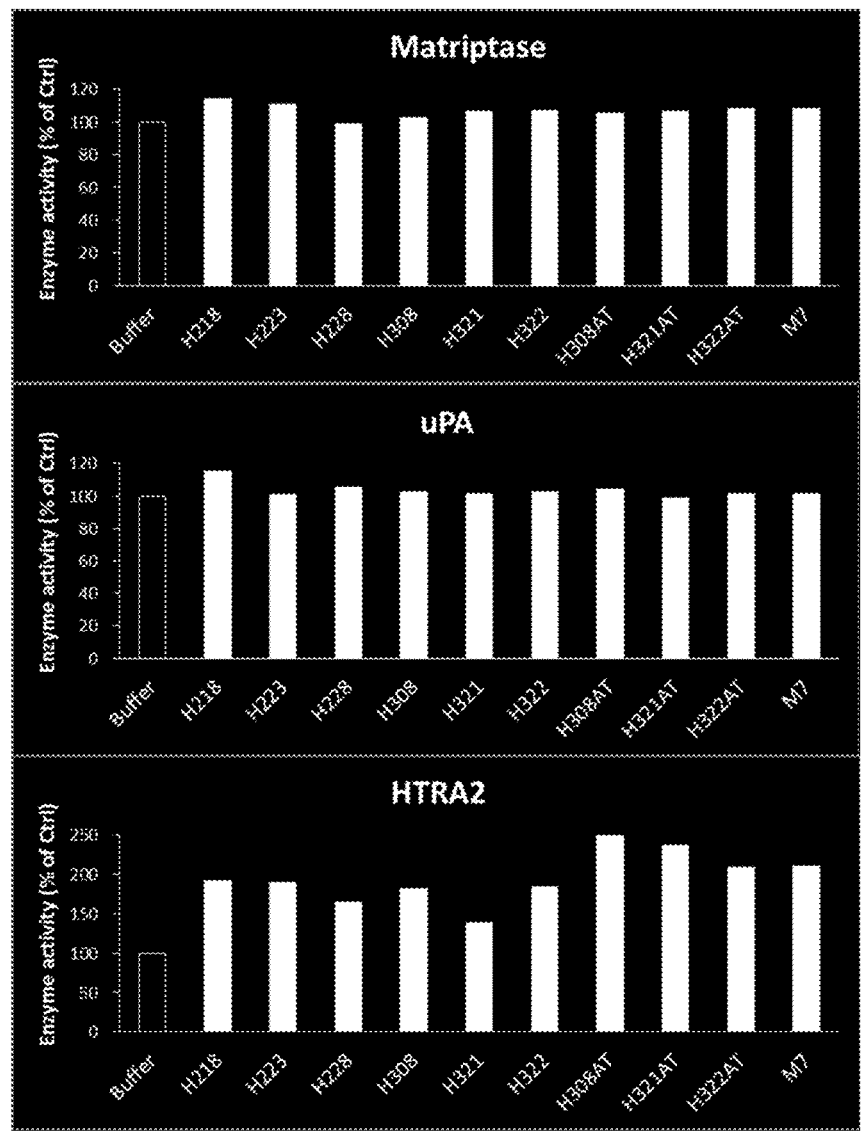
FIG. 5(D) is a diagram showing the results of evaluating the cross-reactivity of a HTRA1-inhibiting peptide with each protease by using the decomposition of a peptide substrate as an indicator (part 4).

As in (3-1), the HTRA1-inhibiting peptides also strongly exhibited the inhibition of HTRA1 (cat) when human vitronectin was used as a substrate (FIG. 4).

(3-3) Evaluation of HTRA1-Inhibiting Peptide for Specificity

Specificity for other proteases was evaluated by using the cleavage of a substrate peptide as an indicator. In the same way as the method described in (3-1), each protease and each sample (final concentration: 1 µM) diluted with an assay buffer were mixed at 25 µL each and reacted at 37° C. for 20 minutes. Then, 50 µL of each substrate diluted with an assay buffer was added thereto. A fluorescent signal (excitation at 380 nm/emission at 460 nm) was measured using Enspire (PerkinElmer, Inc.). The same assay buffer (50 mM borate and 150 mM NaCl, pH 8.5) as in Example 2 was used in the evaluation of HTRA2 activity. An assay buffer (50 mM Tris and 150 mM NaCl, pH 8.0) was used in the evaluation of protease activity other than HTRA2 activity. PROTEOSAVE® SS96F black plate (Sumitomo Bakelite Co., Ltd.) was used in the reaction and the measurement. The combinations of the protease and the substrate used in the specificity evaluation were as follows.

Bovine trypsin inhibitory activity evaluation; 5 nM (final concentration) trypsin (Pierce; 20233) and 100 µM (final concentration) substrate peptide Boc-VPR-AMC Fluorogenic Peptide Substrate (R&D Systems, Inc.; ES011) Bovine α-chymotrypsin inhibitory activity evaluation; 10 nM (final concentration) chymotrypsin (Worthington Biochemical Corporation; LS001434) and 100 µM (final concentration) substrate peptide Suc-Leu-Leu-Val-Tyr-MCA (SEQ ID NO:67) (Peptide Institute, Inc.; 3120-v) Human tryptase inhibitory activity evaluation; 1 nM (final concentration) tryptase (Sigma-Aldrich Co. LLC; T7063) and 100 µM (final concentration) substrate peptide Boc-Phe-Ser-Arg-MCA (Peptide Institute, Inc.; 3107-v) Human chymase inhibitory activity evaluation; 100 nM (final concentration) chymase (Sigma-Aldrich Co. LLC; C8118) and 100 µM (final concentration) substrate peptide Suc-Leu-Leu-Val-Tyr-MCA (SEQ ID NO:67) (Peptide Institute, Inc.; 3120-v) Human plasmin inhibitory activity evaluation; 50 nM (final concentration) plasmin (Sigma-Aldrich Co. LLC; P1867) and 100 µM (final concentration) substrate peptide Boc-Val-Leu-Lys-MCA (Peptide Institute, Inc.; 3104-v) Human thrombin inhibitory activity evaluation; 1 nM (final concentration) thrombin (Sigma-Aldrich Co. LLC; T6884) and 100 µM (final concentration) substrate peptide Boc-VPR-AMC Fluorogenic Peptide Substrate (R&D Systems, Inc.; ES011) Human matriptase inhibitory activity evaluation; 1 nM (final concentration) matriptase (R&D Systems, Inc.; E3946-SE) and 100 µM (final concentration) substrate peptide Boc-QAR-AMC Fluorogenic Peptide Substrate (R&D Systems, Inc.; ES014) Human protein C inhibitory activity evaluation; 100 nM (final concentration) protein C (Sigma-Aldrich Co. LLC; P2200) and 100 µM (final concentration) substrate peptide Boc-Leu-Ser-Thr-Arg-MCA (SEQ ID NO:68) (Peptide Institute, Inc.; 3112-v)

Human tPA inhibitory activity evaluation; 10 nM (final concentration) tPA (Sigma-Aldrich Co. LLC; T0831) and 100 M (final concentration) substrate peptide Pyr-Gly-Arg-MCA (Peptide Institute, Inc.; 3145-v)

Human uPA inhibitory activity evaluation; 10 nM (final concentration) uPA (Sigma-Aldrich Co. LLC; T0831) and 100 M (final concentration) substrate peptide Pyr-Gly-Arg-MCA (Peptide Institute, Inc.; 3145-v)

Human plasma kallikrein inhibitory activity evaluation; 0.125 µg/ml (final concentration) plasma kallikrein (Sigma-Aldrich Co. LLC; T0831) and 100 µM (final concentration) substrate peptide Z-Phe-Arg-MCA (Peptide Institute, Inc.; 3095-v)

Human HTRA2 inhibitory activity evaluation; 200 nM (final concentration) HTRA2 (R&D Systems, Inc.; 1458-HT) and 50 µM (final concentration) substrate peptide H2-Opt (Peptide Institute, Inc.)

Cross-reactivity with proteases other than HTRA1 was evaluated by using the decomposition of the peptide substrate as an indicator in the same way as in (3-2). Each HTRA1-inhibiting peptide did not suppress the protease activity of any of the proteases at a final inhibitor concentration of 1 micro M, indicating that each HTRA1-inhibiting peptide has a HTRA1-specific inhibitory effect (FIG. 5).

Example 4. Analysis of HTRA1-Inhibiting Peptide Using X-Ray Crystal Structure (4-1) Preparation of HTRA1 (Cat)/HTRA1-Inhibiting Peptide Complex HTRA1 (cat) and a HTRA1-inhibiting peptide having the amino acid sequence shown in SEQ ID NO: 3 were each prepared according to the methods described in (1-2) and (2-1). These were mixed under conditions of 20 mM Tris-HCl and 150 mM NaCl, pH 7.6. Then, a complex was isolated and purified by gel filtration chromatography (Superdex 200 10/300 GL).

(4-2) X-Ray Crystallography

Figure 6:
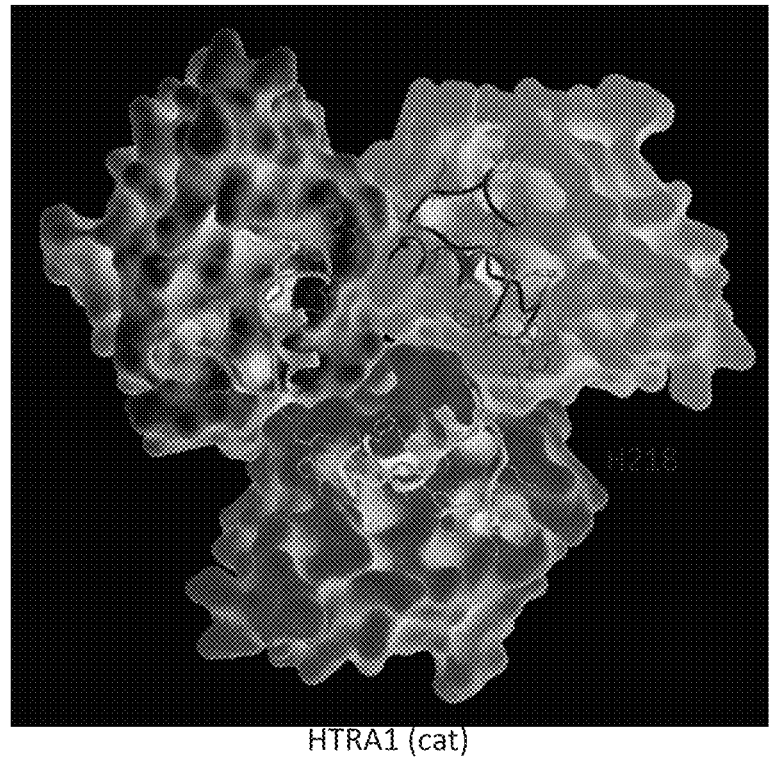
FIG. 6 is a diagram showing a HTRA1 (cat)/HTRA1-inhibiting peptide complex obtained by X-ray crystallography. The inhibiting peptide is bound to each molecule of a HTRA1 trimer formed by HTRA1 (cat).
Figure 7:
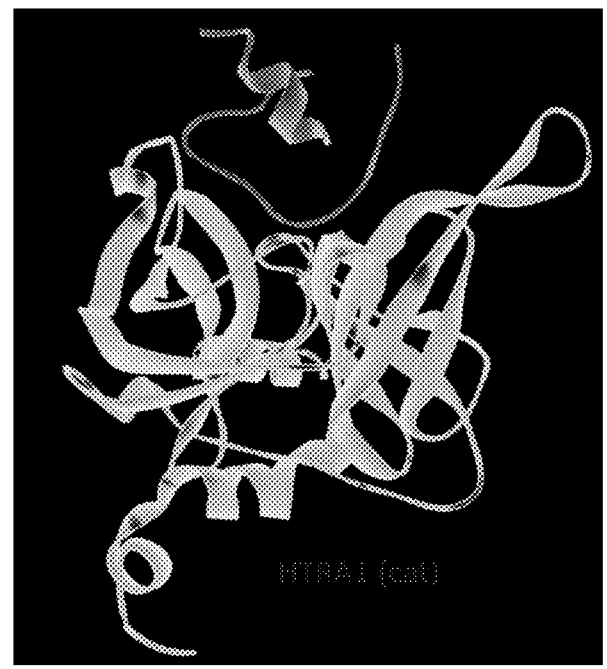
FIG. 7 is a diagram showing a HTRA1 (cat)/HTRA1-inhibiting peptide complex obtained by X-ray crystallography as a monomer. The inhibiting peptide is bound to a region containing the active center of HTRA1 (cat).

The complex solution prepared in (4-1) was concentrated into 18 mg/ml and then mixed with a reservoir solution (1.0 M LiCl, 7.5% PEG6000, and 0.1 M Tris/HCl (pH 8.5)) at a ratio of 1:1, and the mixture was crystallized by the vapor diffusion method. The obtained cubic monocrystals were dipped in a reservoir solution containing 20% ethylene glycol and then frozen in liquid nitrogen. The frozen crystals were exposed to X-rays under cryogenic air flow to obtain a diffraction image (photon factory BL5A: High Energy Accelerator Research Organization). Scaling data with a maximum resolution of 2.6 Angstrom was obtained by analysis using HKL2000. The phase was determined by the molecular replacement method using serine protease HTRA1 (PDB ID: 3NZI) as a template. After structure refinement, a crystalline complex of HTRA1 (cat) and the peptide was determined at a resolution of 2.6 Angstrom. One each of HTRA1 and SPINK2 molecules was contained in the unit cell. As for the SPINK2 molecule, a partial molecular model containing an interaction site with HTRA1 (cat) was constructed on the basis of the sequence information and the observed electron density. The HTRA1-inhibiting peptide was confirmed to bind to a region containing the active center of the HTRA1 enzyme (FIGS. 6 and 7).

Example 5. Retinal Protective Effect Brought about by Inhibition of HTRA1 in Rat Model of Retinal Damage Induced by Light Exposure (5-1) Preparation of Rat Model of Retinal Damage Induced by Light Exposure Rat models of retinal damage induced by light exposure are models that induce the cell death of retinal photoreceptor cells by light exposure and are universally used as model animals of retinal degeneration (Daniel T. Organisciak et al., (1996) Invest Ophthalmol Vis Sci. Vol. 37 (No. 11): p.

2243-2257). A 0.5% (W/V) tropicamide-0.5% phenylephrine hydrochloride ophthalmic solution was ocularly instilled under adaptation to darkness to rats adapted to darkness for 72 hours. Then, the rats were exposed to white light of 5500 Lux for 3 hours. The rats thus exposed were adapted again to darkness for about 24 hours and then raised for 2 days under light-dark conditions of ordinary raising. After euthanasia, the eyeballs were excised and fixed by dipping in a 3.7% (W/V) formaldehyde-0.5 to 1% (W/V) methanol-0.2% (W/V) picric acid fixative for 24 hours or longer. After paraffin embedding, thin sliced sections were prepared. The sections were stained with hematoxylin-eosin, and a nucleus count in an outer nuclear layer of a cross-section of the retina was determined to evaluate retinal damage. The rat models of retinal damage induced by light exposure were found to have a marked decrease in nucleus count in an outer nuclear layer due to light exposure.

Figure 9:
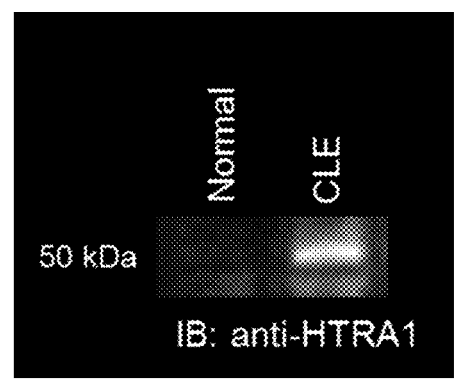
FIG. 9 is a diagram showing that the expression of HTRA1 was increased in the vitreous humor of a rat model of retinal damage induced by light exposure. Analysis was conducted by Western blot using Human HTRA1/PRSS11 Antibody (R&D Systems, Inc.; AF2916).

(5-2) Confirmation of Expression of Extracellular HTRA1 at Time of Retinal Damage In order to examine the involvement of HTRA1 in rat models of retinal damage induced by light exposure, vitreous humor was collected from the model rats prepared in (5-1) and evaluated for a HTRA1 expression level by Western blot analysis. The vitreous humor was subjected to SDS-PAGE under reductive conditions. Rat HTRA1 was detected using as a primary antibody Human HTRA1/PRSS11 Antibody (R&D Systems, Inc.; AF2916) and as a secondary antibody Sheep IgG Horseradish Peroxidase-conjugated Antibody (R&D Systems, Inc.; HAF016). The increased amount of HTRA1 in the vitreous humor was confirmed in the light exposure group as compared with a non-exposure group, suggesting that in this model, HTRA1 is involved in the process of retinal damage caused by light exposure (FIG. 9).

Figure 10:
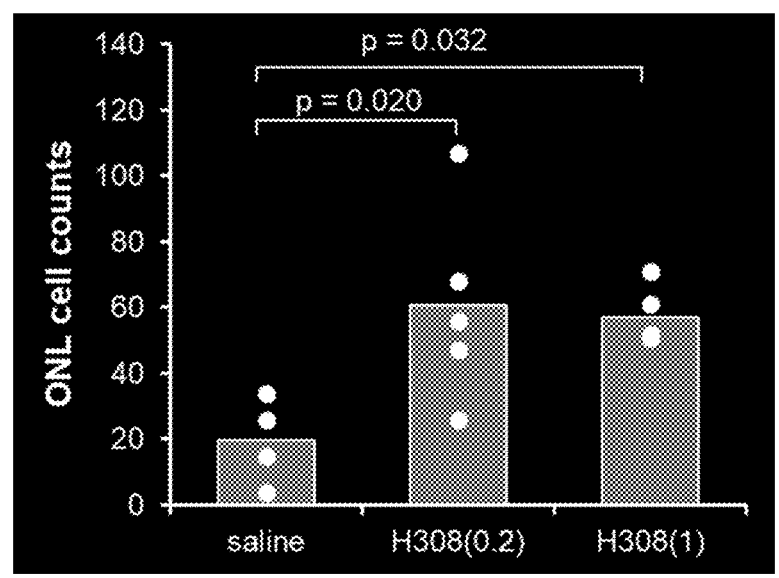
FIG. 10 is a diagram showing that a HTRA1-inhibiting peptide administration group of rat models of retinal damage induced by light exposure suppressed a decrease in nucleus count in an outer nuclear layer on a cross-section of the retina. n=4 for a normal saline administration group, and n=5 for the other groups.

(5-3) Retinal Protective Effect of HTRA1-Inhibiting Peptide in Rat Model of Retinal Damage Induced by Light Exposure Immediately before light exposure of rats, 5 µL of HTRA1-inhibiting peptide H308 having a concentration of 0.04 mg/mL or 0.2 mg/mL was intravitreally administered under anesthesia. n=4 for a normal saline administration group, and n=5 for the other groups. Light exposure decreased the nucleus count in an outer nuclear layer on a cross-section of the retina in the normal saline administration group, whereas the effect of suppressing the decrease in nucleus count in an outer nuclear layer was confirmed in the HTRA1-inhibiting peptide administration group (FIG. 10). These results demonstrated that the HTRA1-inhibiting peptide exhibits medicinal effects on tissue damage caused by HTRA1.

Example 6. Evaluation of HTRA1-Inhibiting Peptide Derivative (6-1) Construction of pET 32a_HTRA1-Inhibiting Peptide H308_S16A_Kex2

Derivative S16A having an amino acid sequence in which 16Ser in the amino acid sequence shown in SEQ ID NO: 9 (FIG. 21) was substituted with Ala was prepared with HTRA1-inhibiting peptide H308 as a template. Fragment C was amplified by PCR ((94° C. for 15 sec, 60° C. for 30 sec, and 68° C. for 15 sec)×30 cycles) using the following primers and KOD-plus-(Toyobo Co., Ltd.).

Primer 12:
(SEQ ID NO: 44)
5'-CCGCAGTTTGGTCTGTTTAGCAAATATCGTACCCCGAATTGT-3'

Primer 13:
(SEQ ID NO: 45)
5'-GCCATACCAGCATGGTCCGCACAATTCGGGGTACGATATTTGC-3'

Next, fragment D was amplified by PCR ((94° C. for 15 sec, 60° C. for 30 sec, and 68° C. for 20 sec)×30 cycles) with HTRA1-inhibiting peptide H308 as a template using the following primers and KOD-plus-(Toyobo Co., Ltd.).

Primer 14:
(SEQ ID NO: 46)
5'-GCGGACCATGCTGGTATGGCATGTGTTGCTCTGTATGAAC-3'

Primer 15:
(SEQ ID NO: 47)
5'-AAAACTCGAGITAGCCGCCGCACGGACCATTGCGAATAA-3'

The desired DNA fragment was amplified by PCR ((94° C. for 15 sec, 60° C. for 30 sec, and 68° C. for 20 sec)×30 cycles) using fragments C and D, the following primers, and KOD-plus-(Toyobo Co., Ltd.).

Primer 16:
(SEQ ID NO: 48)
5'-AAAAGGATCCCTGGACAAACGTGATCCGCAGTTTGGTCTGTT

TAG-3'

Primer 15

The amplified fragment was subjected to agarose gel electrophoresis. Then, the desired DNA fragment was excised from the gel, and DNA was prepared using a QIAquick Gel Extraction Kit (Qiagen N.V.). The prepared DNA fragment and pET 32a (Novagen) were each treated with restriction enzymes BamHI (New England BioLabs Inc.) and XhoI (New England BioLabs Inc.) at 37° C. for 1 hour or longer. After agarose gel electrophoresis, the desired DNA fragments were excised from the gel and purified using a QIAquick PCR Purification Kit (Qiagen N.V.). The purified fragments were reacted overnight at 16° C. for a ligation reaction using T4 DNA Ligase (New England BioLabs Inc.). The ligation solution was added to E. coli JM109 (Toyobo Co., Ltd.), and the mixture was left standing on ice for 30 minutes, then heat-treated at 42° C. for 45 seconds, further left standing on ice for 5 minutes, and inoculated onto a 2YT plate containing 0.1 mg/ml ampicillin, followed by static culture overnight at 37° C. to transform the E. coli. The transformed E. coli was cultured, and miniprep and sequence analysis were then carried out to construct "pET 32a_HTRA1-inhibiting peptide H308_S16A_Kex2". The operation was performed in accordance with the method described in (1-1-1).

(6-2) Preparation of HTRA1-Inhibiting Peptide_N-Terminal Derivative Expression Vector In order to prepare four N-terminal sequence derivatives (designated as D1G, D1S, D1E, and D1SLI, respectively) of the HTRA1-inhibiting peptide having an amino acid sequence in which 1Asp in the amino acid sequence shown in SEQ ID NO: 9 (FIG. 21) was substituted with Gly, Ser, Glu or Ser-Leu-Ile, expression vectors were constructed by the same approach as in (6-1). Four fragments of interest were each amplified by PCR ((94° C. for 15 sec, 60° C. for 30 sec, and 68° C. for 20 sec)×30 cycles) using fragments C and D, the following primers, and KOD-plus-(Toyobo Co., Ltd.).

47

D1G preparation primers
Primer 17:
(SEQ ID NO: 49)
5'-AAAAGGATCCCTGGACAAACGTGGCCCGCAGTTTGGTCTGTT

TAG-3'

Primer 15

D1S preparation primers
Primer 18:
(SEQ ID NO: 50)
5'-AAAAGGATCCCTGGACAAACGTAGCCCGCAGTTTGGTCTGTT

TAG-3'

Primer 15

D1E preparation primers
Primer 19:
(SEQ ID NO: 51)
5'-AAAAGGATCCCTGGACAAACGTGAACCGCAGTTTGGTCTGTT

TAG-3'

Primer 15

D1SLI preparation primers
Primer 20:
(SEQ ID NO: 52)
5'-AAAAGGATCCCTGGACAAACGTAGCCTGATTCCGCAGTTTGG

TCTGTTTAG-3'

Primer 15

Each of the four amplified fragments was subjected to agarose gel electrophoresis. Then, the desired DNA fragment was excised from the gel, and DNA was prepared using a QIAquick Gel Extraction Kit (Qiagen N.V.). The prepared DNA fragment and pET 32a (Novagen) were each treated with restriction enzymes BamHI (New England BioLabs Inc.) and XhoI (New England BioLabs Inc.) at 37° C. for 1 hour or longer. After agarose gel electrophoresis, the desired DNA fragments were excised from the gel and purified using a QIAquick PCR Purification Kit (Qiagen N.V.). The purified fragments were reacted overnight at 16° C. for a ligation reaction using T4 DNA Ligase (New England BioLabs Inc.). The ligation solution was added to *E. coli* JM109 (Toyobo Co., Ltd.), and the mixture was left standing on ice for 30 minutes, then heat-treated at 42° C. for 45 seconds, further left standing on ice for 5 minutes, and inoculated onto a 2YT plate containing 0.1 mg/ml ampicillin, followed by static culture overnight at 37° C. to transform the *E. coli*. The transformed *E. coli* was cultured, and miniprep and sequence analysis were then carried out to construct "pET 32a_HTRA1-inhibiting peptide H308_D1G_S16A_Kex2", "pET 32a_HTRA1-inhibiting peptide H308_D1S_S16A_Kex2", "pET 32a_HTRA1-inhibiting peptide H308_D1E_S16A_Kex2", and "pET 32a_HTRA1-inhibiting peptide H308_D1SLI_S16A_Kex2". The operation was performed in accordance with the method described in (1-1-1).

(6-3) Preparation of HTRA1-Inhibiting Peptide Derivative

*E. coli* Origami B (DE3) (Novagen) was transformed with each of the five vectors constructed in (6-1) and (6-2), and cultured at 37° C. using a 2YT medium containing 0.1 mg/ml ampicillin. Then, IPTG (final concentration: 1 mM) was added thereto, and the *E. coli* was cultured overnight at 16° C. On the next day, after harvest by centrifugation (3,000 g, 20 min, 4° C.), a lysate was prepared using BugBuster Master Mix (Novagen), and a His tag fusion protein of interest was purified using TALON Metal Affinity Resin (Clontech Laboratories, Inc.). Next, a thioredoxin tag and the desired protein were cleaved using Kex2 (mentioned above) and purified using TALON. The resultant was subjected to gel filtration chromatography (Superdex 75 10/300 GL) or reverse-phase chromatography (YMC-Pack ODS-AM) to prepare five HTRA1-inhibiting peptide derivatives. The amino acid sequences of the derivatives are shown in SEQ ID NOs: 23 to 27 (FIGS. 35 to 39).

Figure 11:
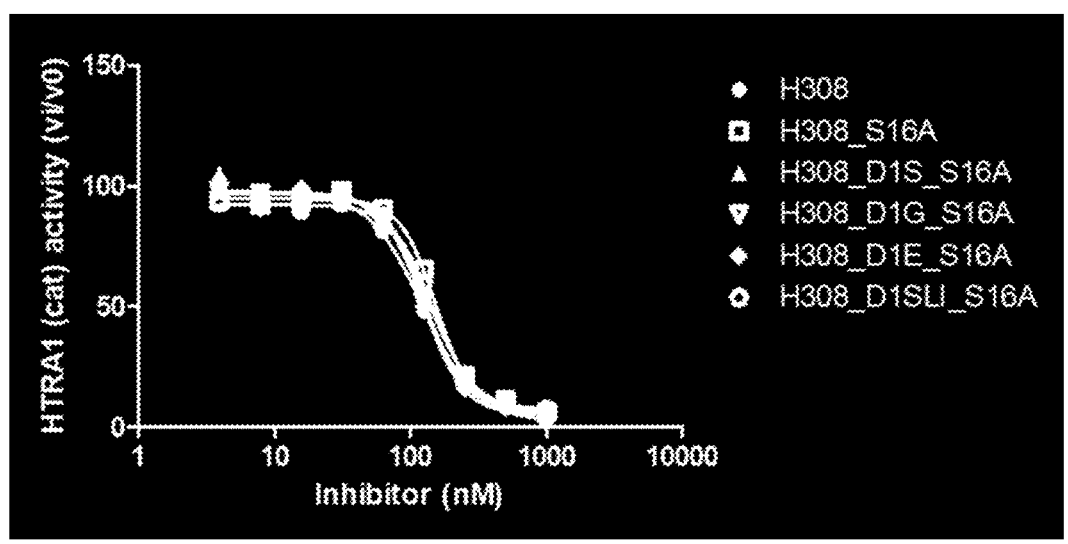
FIG. 11 is a diagram showing the results of evaluating the HTRA1 (cat) inhibitory activity of five HTRA1-inhibiting peptide derivatives by using the decomposition rate of a peptide substrate as an indicator.

(6-4) Evaluation of HTRA1-Inhibiting Peptide Derivative
As a result of measuring HTRA1 (cat) inhibitory activity according to the method described in (3-1), all the derivatives had inhibitory activity equivalent to that of H308 (FIG. 11)

Example 7. Evaluation of HTRA1-Inhibiting Peptide for Binding Activity Against HTRA1 (Cat)

Binding activity was evaluated by the immunoprecipitation method using three HTRA1-inhibiting peptides (H308, H321AT, and H322AT) prepared in Example (1-2) and HTRA1 (cat) prepared in (2-1). 2.5 µg of each HTRA1-inhibiting peptide and 10 µg of HTRA1 (cat) were reacted at room temperature for 30 minutes. Then, 10 µL of TALON Metal Affinity Resin (Clontech Laboratories, Inc.) was added thereto. After further reaction for 30 minutes, the resin was recovered as an immunoprecipitation (IP) fraction and subjected to SDS-PAGE to evaluate binding activity. PBS was used as a buffer in the reaction.

Figure 12:
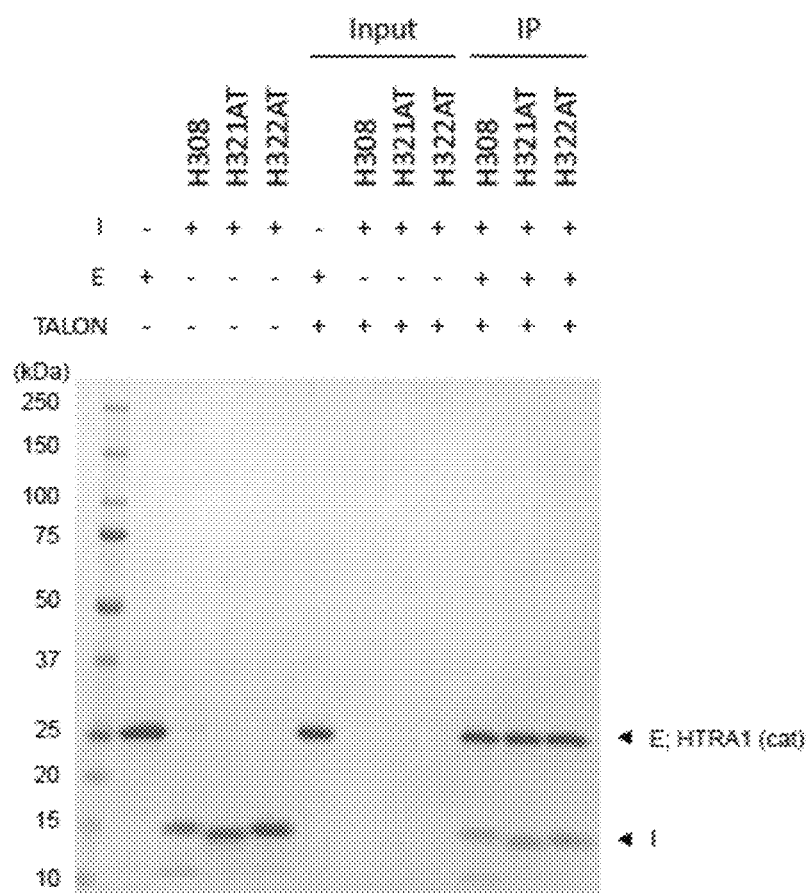
FIG. 12 is a diagram showing the results of evaluating the binding of three HTRA1-inhibiting peptides to HTRA1 (cat) by an immunoprecipitation method.

When each of the three HTRA1-inhibiting peptides or HTRA1 (cat) was reacted with TALON, the band of only His tag-fused HTRA1 (cat) was detected in an input lane. On the other hand, the band of each inhibiting peptide and the enzyme was detected only in an IP lane where the inhibiting peptide was reacted with HTRA1 (cat). Accordingly, each of the three HTRA1-inhibiting peptides was confirmed to bind to HTRA1 (cat) (FIG. 12).

Example 8. Evaluation of HTRA1-Inhibiting Peptide for HTRA1 Inhibitory Activity (8-1) Evaluation of HTRA1-Inhibiting Peptide for HTRA1 Inhibitory Activity Using Peptide Substrate Three HTRA1-inhibiting peptides (H308_DiG_S16A, H321AT_D1G_S16A, and H322AT_D1G_S16A) constructed in Example 6 were evaluated for their HTRA1 (cat) or HTRA1 (full) inhibitory activity using a substrate peptide H2-Opt (n=3). A substrate peptide H2-Opt (Mca-IRRV-SYSFK(Dnp)K) (SEQ ID NO:66) (Peptide Institute, Inc.: SEQ ID NO: 54, FIG. 8) was dissolved at 10 mM in DMSO, diluted with an assay buffer (50 mM Tris, 150 mM NaCl, and 0.25% CHAPS, pH 8.0), and used at a final concentration of 10 µM. HTRA1 (HTRA1 (cat) or HTRA1 (full); Example 2) and each HTRA1-inhibiting peptide diluted with an assay buffer were mixed at 25 µL each and reacted at 37° C. for 20 minutes. Then, 50 µL of the substrate diluted with an assay buffer was added thereto. A fluorescent signal (excitation at 328 nm/emission at 393 nm) was measured using Enspire (PerkinElmer, Inc.). The final concentration of HTRA1 was 100 nM, and the final concentration of the HTRA1-inhibiting peptide was 1.875 to 1,000 nM. PROTEOSAVE(R) SS96F black plate (Sumitomo Bakelite Co., Ltd.) was used in the reaction and the measurement.

The substrate peptide decomposition rate of the HTRA1-inhibiting peptide at each concentration was calculated. When the decomposition rate at an inhibitor concentration of 0 nM was defined as 100%, the HTRA1 (cat) and HTRA1 (full) inhibitory activity of each HTRA1-inhibiting peptide was evaluated.

Figure 66:
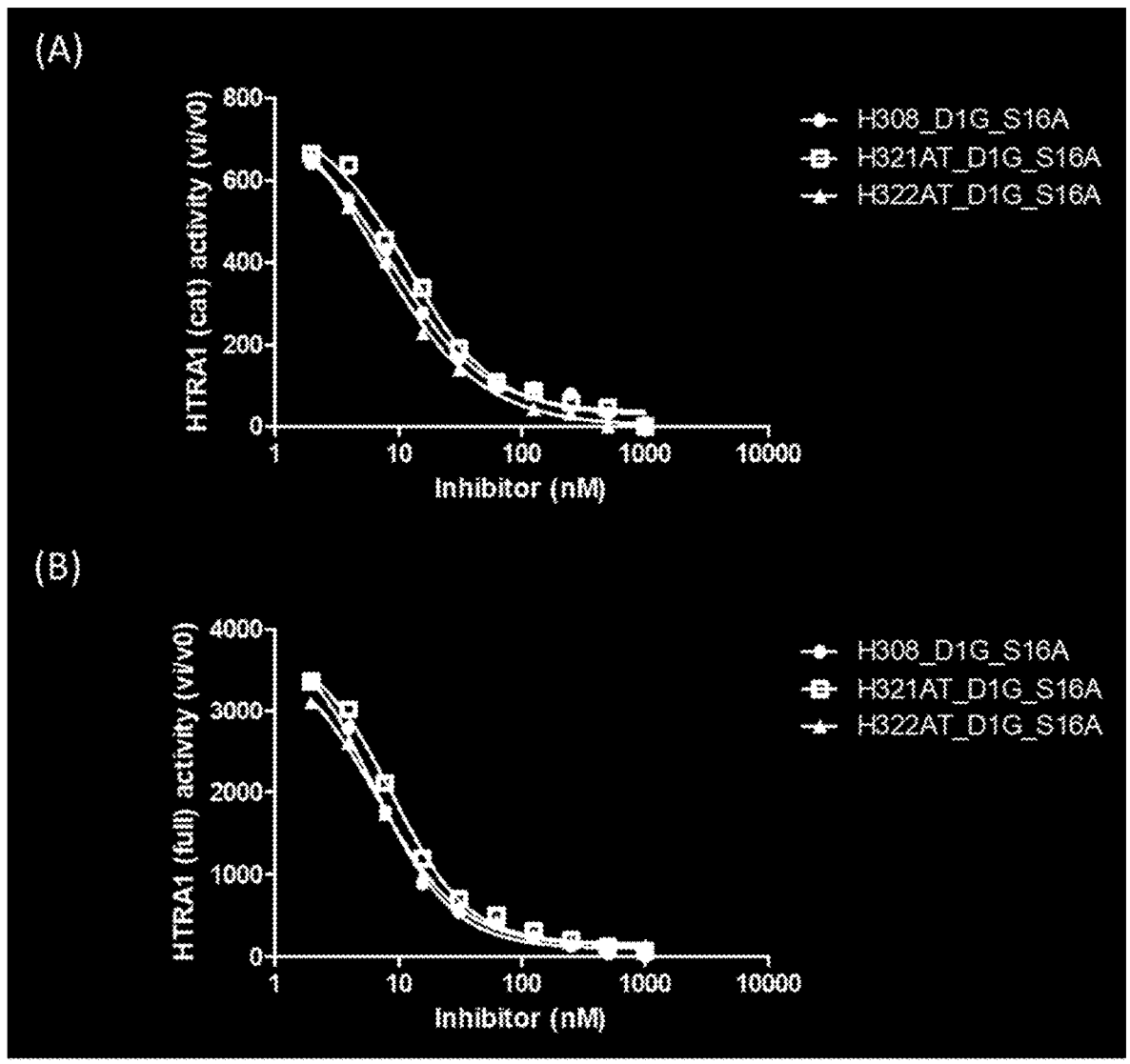
FIG. 66(A) is a diagram showing the results of evaluating the HTRA1 (cat) inhibitory activity of HTRA1-inhibiting peptides by using the decomposition rate of a peptide substrate as an indicator.
FIG. 66(B) is a diagram showing the results of evaluating the HTRA1 (full) inhibitory activity of HTRA1-inhibiting peptides by using the decomposition rate of a peptide substrate as an indicator.

As a result of calculating a 50% inhibitory concentration (IC50) using GraphPad Prism (version 5.0; GraphPad Software Inc.), all the HTRA1-inhibiting peptides were found to inhibit HTRA1 (cat) and HTRA1 (full) enzyme activity at a low concentration (FIG. 66).

TABLE 2

HTRA1 inhibitory activity of each HTRA1-inhibiting peptide

|  | IC50 (nM) for HTRA1 (cat) | IC50 (nM) for HTRA1 (full) |
| --- | --- | --- |
| H308_D1G_S16A | 7.9 ± 1.3 | 9.1 ± 1.4 |
| H321AT_D1G_S16A | 9.0 ± 0.6 | 12.0 ± 1.9 |
| H322AT_D1G_S16A | 12.9 ± 0.2 | 12.2 ± 2.2 |

(8-2) Evaluation of HTRA1-Inhibiting Peptide for HTRA1 Inhibitory Activity Using Protein Substrate The HTRA1 inhibitory activity of a HTRA1-inhibiting peptide was evaluated with human vitronectin as a protein substrate. The operation followed Example (3-2)

Figure 67:
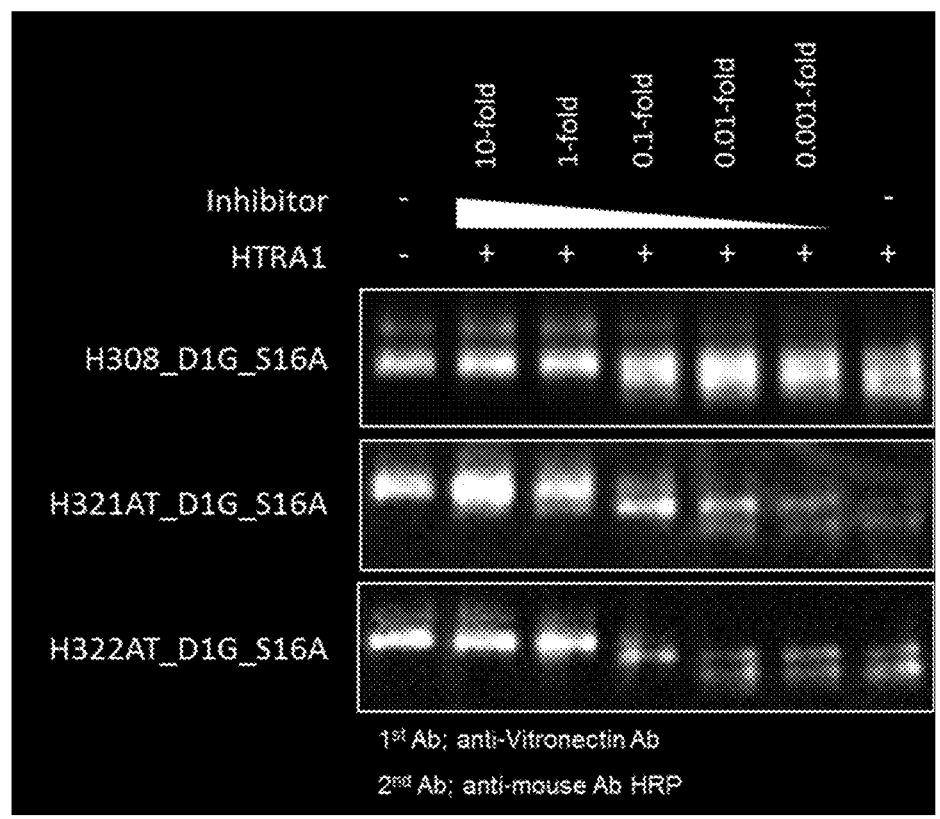
FIG. 67 is a diagram showing the results of evaluating the HTRA1 (cat) inhibitory activity of HTRA1-inhibiting peptides by using the decomposition of human vitronectin as an indicator. Analysis was conducted by Western blot using Human Vitronectin Antibody (R&D Systems, Inc.; MAB2349).
Figure 68A:
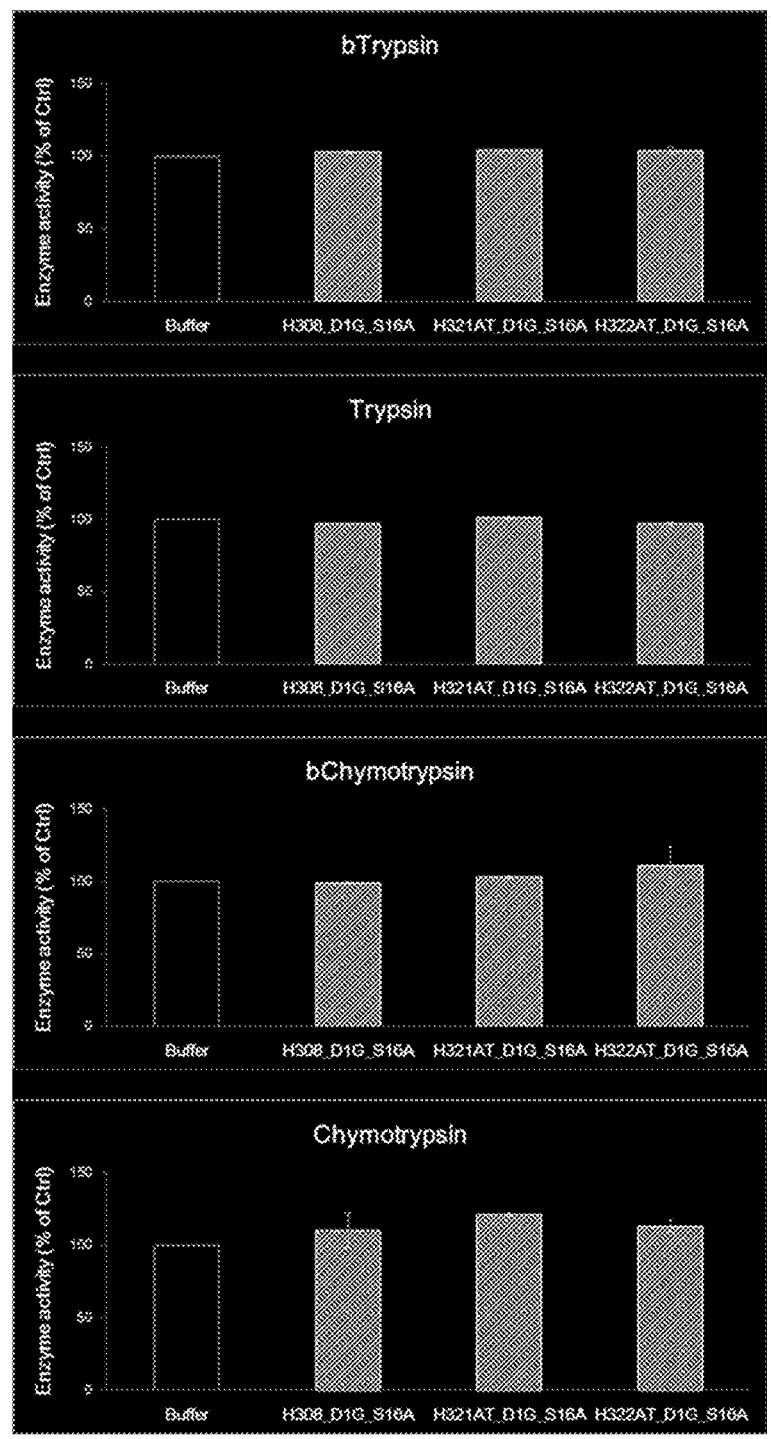
FIG. 68(A) is a diagram showing the results of evaluating the cross-reactivity of HTRA1-inhibiting peptides with each protease by using the decomposition of a peptide substrate as an indicator (part 1).
Figure 68B:
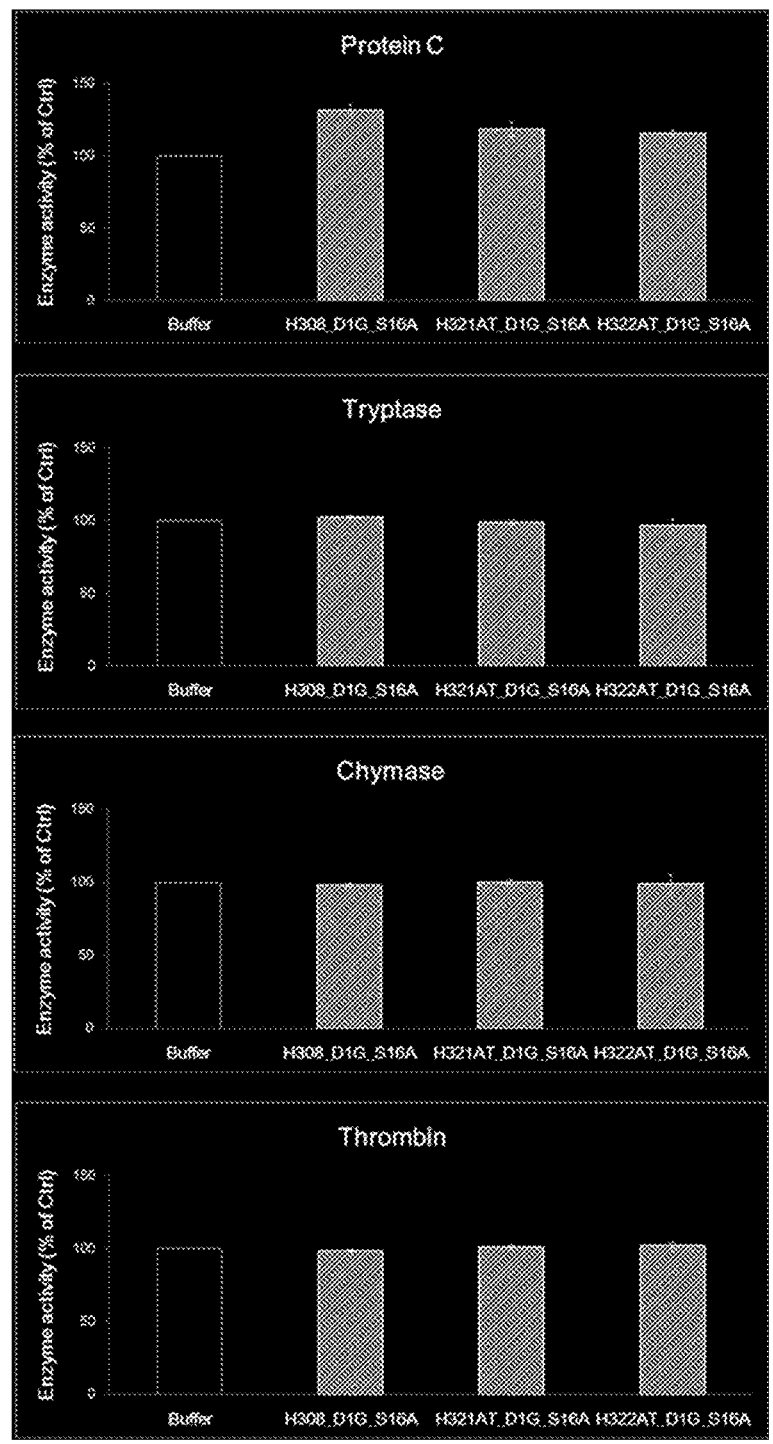
FIG. 68(B) is a diagram showing the results of evaluating the cross-reactivity of HTRA1-inhibiting peptides with each protease by using the decomposition of a peptide substrate as an indicator (part 2).
Figure 68C:
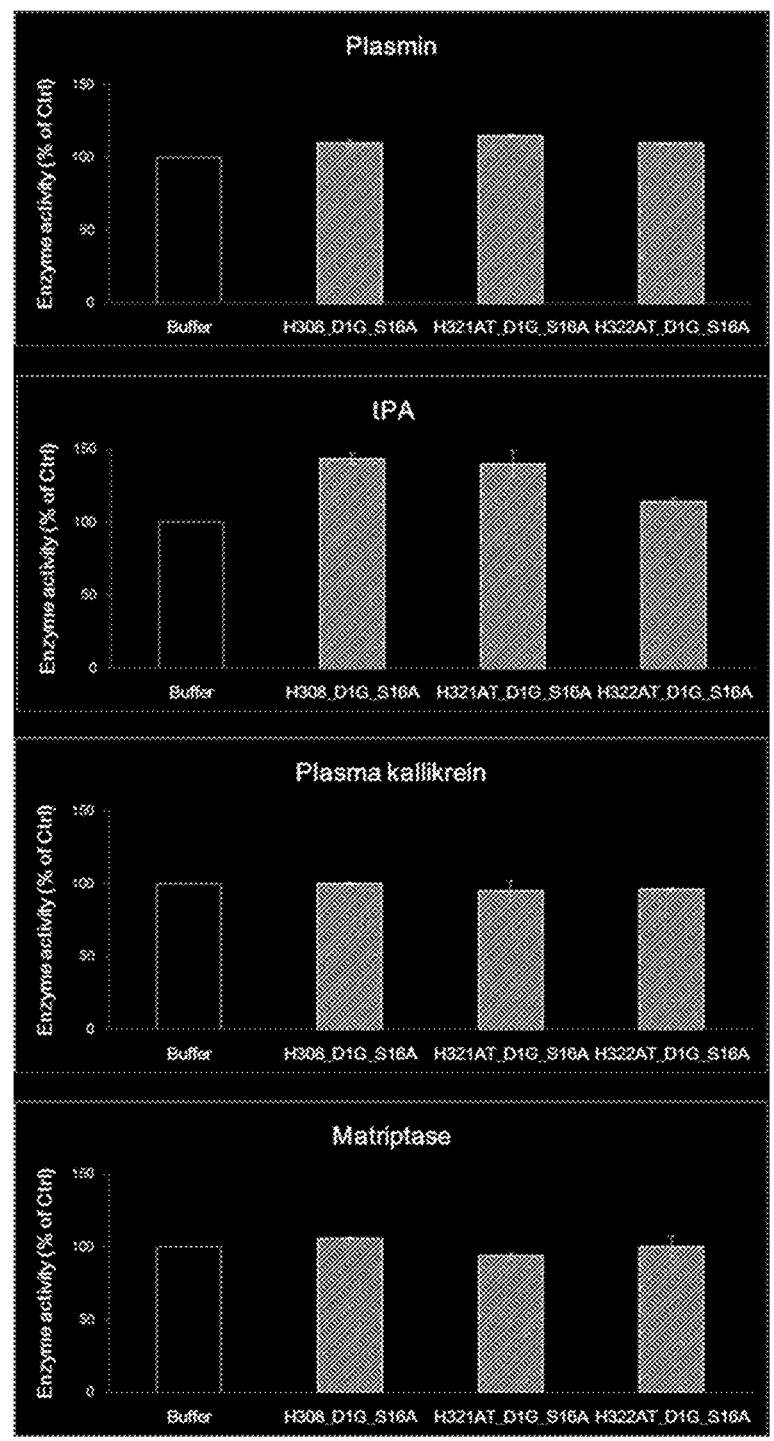
FIG. 68(C) is a diagram showing the results of evaluating the cross-reactivity of HTRA1-inhibiting peptides with each protease by using the decomposition of a peptide substrate as an indicator (part 3).
Figure 68D:
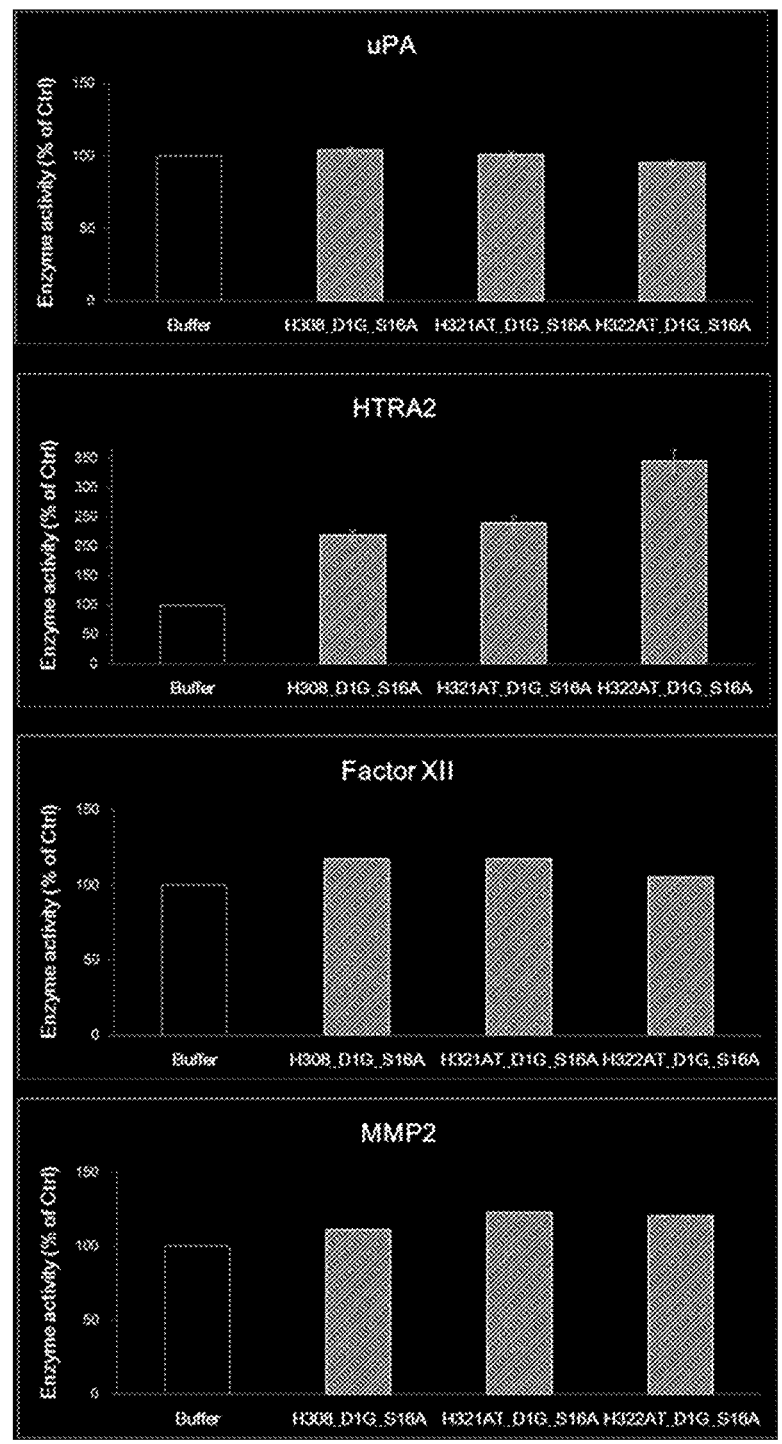
FIG. 68(D) is a diagram showing the results of evaluating the cross-reactivity of HTRA1-inhibiting peptides with each protease by using the decomposition of a peptide substrate as an indicator (part 4).
Figure 68E:
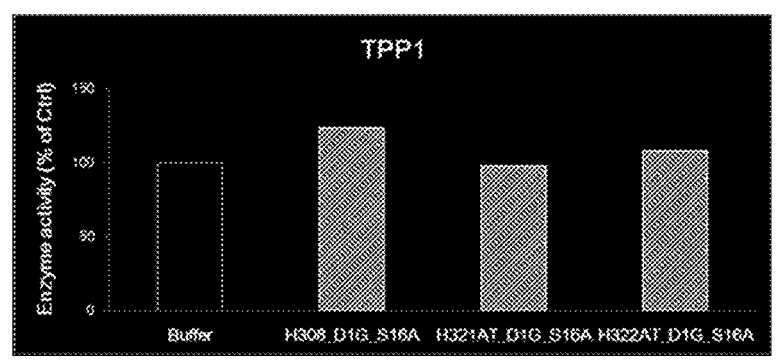
FIG. 68(E) is a diagram showing the results of evaluating the cross-reactivity of HTRA1-inhibiting peptides with each protease by using the decomposition of a peptide substrate as an indicator (part 5).

As in (8-1), the HTRA1-inhibiting peptides also strongly exhibited the inhibition of HTRA1 (cat) when human vitronectin was used as a substrate (FIG. 67).

(8-3) Evaluation of HTRA1-Inhibiting Peptide for Specificity

Specificity for other proteases was evaluated by using the cleavage of a substrate peptide as an indicator. The operation for bovine trypsin, bovine α-chymotrypsin, protein C, tryptase, chymase, thrombin, plasmin, tPA, plasma kallikrein, matriptase, uPA, and HTRA2 followed the method described in Example (3-3) (n=3). Procedures of measuring inhibitory activity against other proteases and combinations of the protease and the substrate were as follows.

PROTEOSAVE(R) SS96F black plate (Sumitomo Bakelite Co., Ltd.) was used in reaction and measurement. Each protease and each sample (final concentration: 1 μM) diluted with an assay buffer were mixed at 25 μL each and reacted at 37° C. for 20 minutes. Then, 50 μL of each substrate diluted with an assay buffer was added thereto. A fluorescent signal was measured using Enspire (PerkinElmer, Inc.).

Human trypsin inhibitory activity evaluation; 1 nM (final concentration) trypsin (Sigma-Aldrich Co. LLC; T6424) and 100 WM (final concentration) substrate peptide Boc-VPR-AMC Fluorogenic Peptide Substrate (R&D Systems, Inc.; ES011), fluorescent signal: excitation at 380 nm/emission at 460 nm.

Human chymotrypsin inhibitory activity evaluation; 10 nM (final concentration) chymotrypsin (Sigma-Aldrich Co. LLC; C8946) and 10 WM (final concentration) substrate peptide Suc-Leu-Leu-Val-Tyr-MCA (SEQ ID NO:67) (Peptide Institute, Inc.; 3120-v), fluorescent signal: excitation at 380 nm/emission at 460 nm.

Human factor XIIa inhibitory activity evaluation; 100 nM (final concentration) Factor Alpha-XIIa (Enzyme Research Laboratories Inc.) and 100 μM (final concentration) substrate peptide Pyr-Gly-Arg-MCA (Peptide Institute, Inc.; 3145-v), fluorescent signal: excitation at 380 nm/emission at 460 nm.

Human MMP-2 inhibitory activity evaluation; 1 nM (final concentration) MMP-2 (Calbiochem; PF023) and 100 μM (final concentration) substrate peptide MOCAx-KPLGL-A2pr(Dnp)-AR (SEQ ID NO:69) (Peptide Institute, Inc.; 3226-v), fluorescent signal: excitation at 328 nm/emission at 393 nm.

Human TPP1 inhibitory activity evaluation; 0.5 μg/mL (final concentration) TPP1 (Calbiochem; 2237-SE) and 200 M (final concentration) substrate peptide AAF-MCA (Peptide Institute, Inc.; 3201-v), fluorescent signal: excitation at 380 nm/emission at 460 nm.

Cross-reactivity with proteases other than HTRA1 was evaluated by using the decomposition of the peptide substrate as an indicator. Each HTRA1-inhibiting peptide did not suppress the protease activity of any of the proteases at a final concentration of 1 μM, indicating that the HTRA1-inhibiting peptide has a HTRA1-specific inhibitory effect (FIG. 68).

Example 9. Evaluation of HTRA1-Inhibiting Peptide for Binding Activity Against HTRA1 (Cat)

Binding activity was evaluated by the immunoprecipitation method according to the operation of Example 7 using three HTRA1-inhibiting peptides prepared in Example 6 and HTRA1 (cat) prepared in (2-1).

Figure 69:
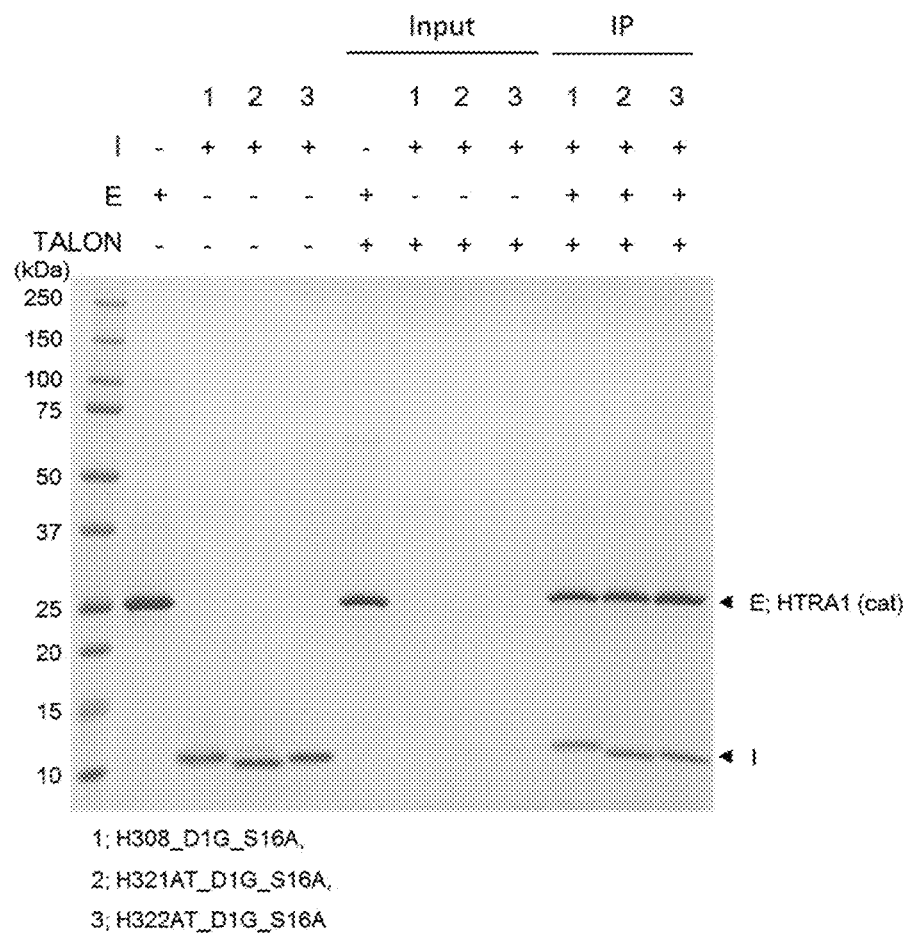
FIG. 69 is a diagram showing the results of evaluating the binding of three HTRA1-inhibiting peptides to HTRA1 (cat) by an immunoprecipitation method.
Figure 70A:
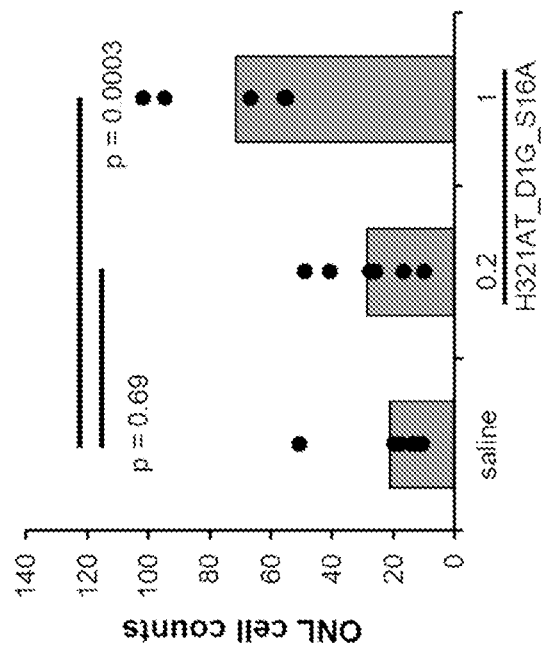
FIG. 70(A) is a diagram showing that a HTRA1-inhibiting peptide H308_D1G_S16A administration group of rat models of retinal damage induced by light exposure suppressed a decrease in nucleus count in an outer nuclear layer on a cross-section of the retina. n=6 for all groups. The dose of the HTRA1-inhibiting peptide H308_D1G_S16A was 0.2 and 1 μg/eye.
Figure 70B:
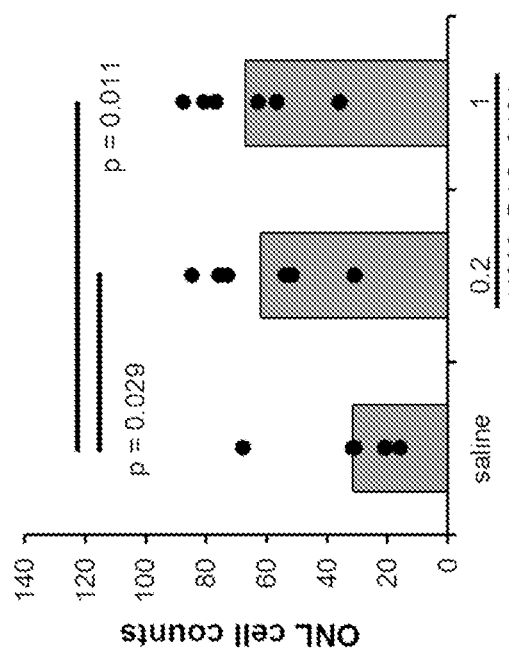
FIG. 70(B) is a diagram showing that a HTRA1-inhibiting peptide H321AT_D1G_S16A administration group of rat models of retinal damage induced by light exposure suppressed a decrease in nucleus count in an outer nuclear layer on a cross-section of the retina. n=6 for all groups. The dose of the HTRA1-inhibiting peptide H321AT_D1G_S16A was 0.2 and 1 μg/eye.
Figure 70C:
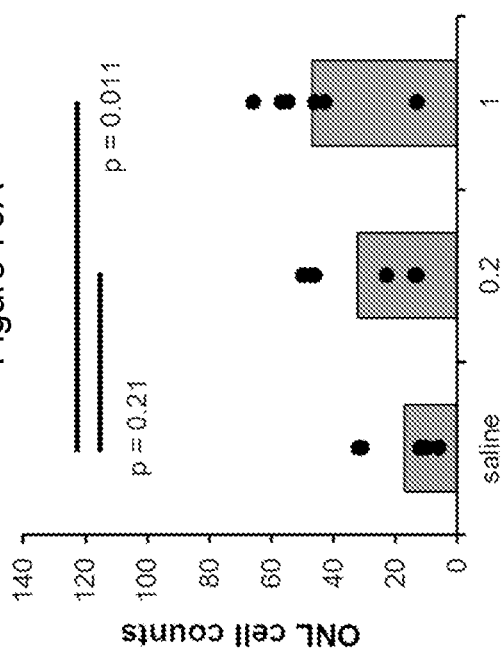
FIG. 70(C) is a diagram showing that a HTRA1-inhibiting peptide H322AT_D1G_S16A administration group of rat models of retinal damage induced by light exposure suppressed a decrease in nucleus count in an outer nuclear layer on a cross-section of the retina. n=6 for all groups. The dose of the HTRA1-inhibiting peptide H322AT_D1G_S16A was 0.2 and 1 μg/eye.

When each of the three HTRA1-inhibiting peptides or HTRA1 (cat) was reacted with TALON, the band of only His tag-fused HTRA1 (cat) was detected in an input lane. On the other hand, the band of each inhibiting peptide and the enzyme was detected only in an IP lane where the inhibiting peptide was reacted with HTRA1 (cat). Accordingly, each of the three HTRA1-inhibiting peptides was confirmed to bind to HTRA1 (cat) (FIG. 69).

Example 10. Retinal Protective Effect Brought about by Inhibition of HTRA1 in Rat Model of Retinal Damage Induced by Light Exposure (Part 2)

The retinal protective effects of three HTRA1-inhibiting peptides prepared in Example 6 were evaluated using the rat models of retinal damage induced by light exposure, constructed in Example (5-1). The operation followed Example 5. n=6 for all groups.

Figure 70:
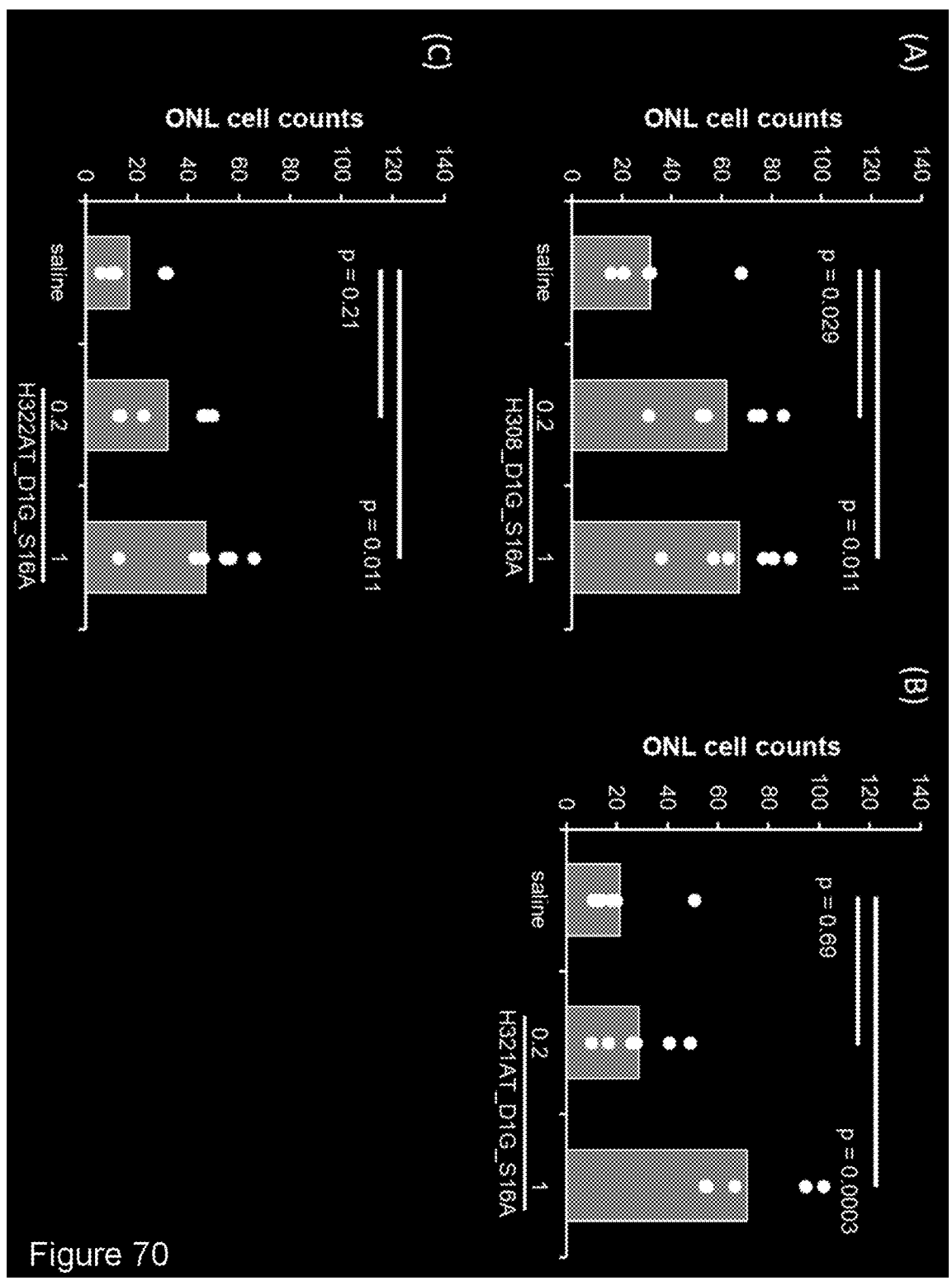
Figure 71:
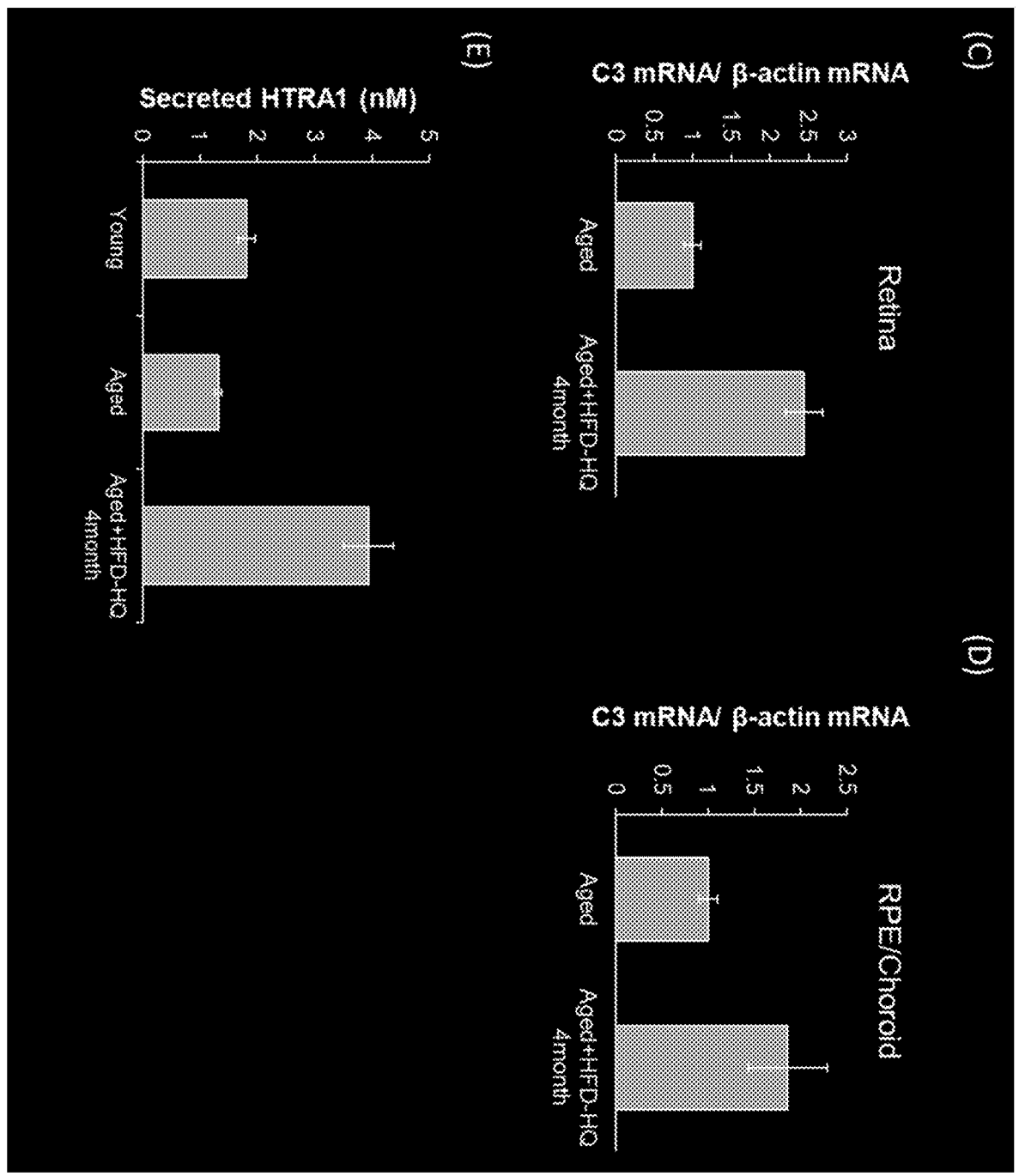

Results of pathologically evaluating the retina are shown in FIG. 70. The three HTRA1-inhibiting peptides exhibited a marked suppressive effect on the decrease in nucleus count in an outer nuclear layer caused by light exposure.

Example 11. Protective Effect on Retinal Pigment Epithelial Cells by Inhibition of HTRA1 in Rabbit Model of Retinal Damage Caused by Loading with High-Fat Diet Containing Hydroquinone (11-1) Preparation of Rabbit Retinal Damage Model by Loading with High-Fat Diet Containing Hydroquinone Retinal damage models prepared using high-fat diet (HFD) and hydroquinone (HQ) are models in which oxidative stress is induced by a pro-oxidant to cause retinal damage. These models have been reported only for mice (Diego G. Espinosa-Heidmann et al., (2006) Invest Ophthalmol Vis Sci., Vol. 47 (No. 2): p. 729-737). Accordingly, 3-year-old JW rabbits were fed for 4 months with RC4 (Oriental Yeast Co., Ltd.) diet containing 1.5% (W/V) coconut oil-0.25% (W/V) cholesterol-1.5% (W/V) peanut oil-2.4% (W/V) hydroquinone (HFD-HQ) to construct rabbit retinal damage models. After euthanasia, the eyeballs were excised, and the anterior segment of the eye was removed by an external incision of about 5 mm from the corneal limbus.

The vitreous body was further separated. Then, retina-choroid-sclera was fixed by dipping in 4% (W/V) paraformaldehyde fixative for 24 hours or longer. After the fixation, the choroid was separated and immunostained using as a primary antibody ZO-1 Monoclonal Antibody (ZO1-1A12) (Thermo Fisher Scientific Inc.; 33-9100) and as a secondary antibody Chicken anti-Mouse IgG (H+L) Cross-Adsorbed Secondary Antibody, Alexa Fluor 594 (Thermo Fisher Scientific Inc.; A-21201). The stained choroid was observed under a fluorescence microscope (BZ-9000; Keyence Corp.). The area of stained retinal pigment epithelial (RPE) cells was determined to evaluate RPE cell damage.

Figure 71:
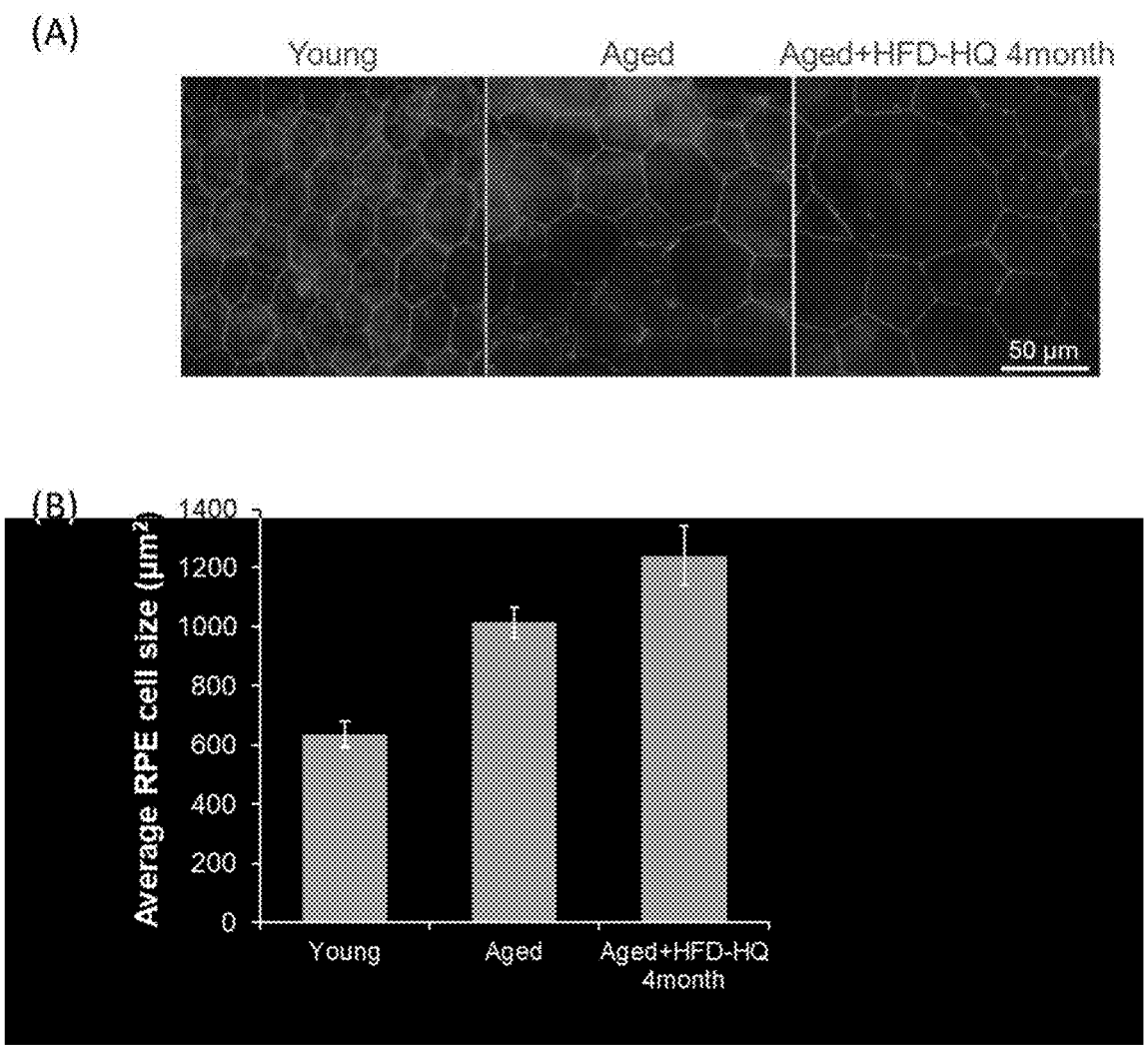
FIG. 71(A) is a diagram showing the results of immunostaining RPE cells in a 12-week-old rabbit, a 3-year-old rabbit, and a HFD-HQ-loaded 3-year-old rabbit with a ZO-1 antibody (Thermo Fisher Scientific Inc.).
FIG. 71(B) shows the average areas of RPE cells in a 12-week-old rabbit, a 3-year-old rabbit, and a HFD-HQ-loaded 3-year-old rabbit.
FIG. 71(C) is a diagram showing the increased expression of the mRNA of complement component 3 "C3", which is an AMD-related factor, in the retinal tissue of a HFD-HQ-loaded 3-year-old rabbit.
FIG. 71(D) is a diagram showing the increased expression of the mRNA of complement component 3 "C3", which is an AMD-related factor, in the RPE/choroid tissue of a HFD-HQ-loaded 3-year-old rabbit.
FIG. 71(E) is a diagram showing the results of measuring HTRA1 concentration in the vitreous humor of a 12-week-old rabbit, a 3-year-old rabbit, and a HFD-HQ-loaded 3-year-old rabbit by LC-MS/MS.

FIG. 71 shows stain images of the RPE cells of a 12-week-old rabbit, a 3-year-old rabbit and a HFD-HQ-loaded 3-year-old rabbit (FIG. 71(A)) and a graph of the average areas of the RPE cells (FIG. 71(B)). The RPE cells were confirmed to be more hypertrophied in the 3-year-old rabbit than in the 12-week-old rabbit and to be further hypertrophied by HFD-HQ loading. Damage was confirmed to appear in the RPE cells. Similar change has been observed in the eyeballs of age-related macular degeneration patients (Ding J D et al., (2011) Proc Natl Acad Sci USA., Vol. 108 (No. 28): p. 279-87).

(11-2) Increase in AMD-Related Factor C3 Expression Level at Time of Retinal Damage In order to evaluate the expression of an AMD-related factor, tissues were respectively collected from the retina and the RPE/choroid of the rabbit retinal damage models. mRNA was extracted using an RNeasy mini kit (Qiagen N.V.) and then subjected to a reverse transcription reaction using a TaqMan Gene Expression Master Mix (Thermo Fisher Scientific Inc.). The mRNA levels of complement component 3 (C3) and an internal standard β-actin were quantitatively analyzed by a TaqMan Gene Expression Assay (Oc03397832_g1 and Oc03824857_g1; Thermo Fisher Scientific Inc.) using 7900HT Fast Real-Time PCR System (Applied Biosystems, Inc.). The analysis was carried out at n=4 for 3-year-old rabbits and n=10 for HFD-HQ-loaded 3-year-old rabbits.

The C3 expression levels in the retina and in the RPE cells and the choroid are shown in FIGS. 71 (C) and (D). For both the tissues, the expression level of C3 was confirmed to be increased in the rabbit group given HFD-HQ.

(11-3) Increase in HTRA1 Protein Level at Time of Retinal Damage

In order to examine the involvement of HTRA1 in rabbit retinal damage models, vitreous humor was collected from the model rabbits prepared in (11-1), and enzymatically digested with Trypsin/Lys-C Mix (Promega Corp.). Then, a peptide fragment of HTRA1 was quantified using LC (EASY-nLC 1000; Thermo Fisher Scientific Inc.)-MS (TripleTOF 6600; AB Sciex Pte. Ltd). The HTRA1 protein level was found to be increased in the vitreous humor of the rabbits given HFD-HQ (FIG. 71(E)). From these results, the hypertrophy of RPE cells and the increased expression of the AMD-related factor C3 and HTRA1 were confirmed, indicating that the rabbit retinal damage models are useful in research on age-related retinal disease.

(11-4) Retinal Protective Effect of HTRA1 Inhibitor in Rabbit Retinal Damage Model The retinal protective effect of the HTRA1-inhibiting peptide H308 prepared in Example 1 was evaluated using the rabbit models. After 2 months from the start of feeding with HFD-HQ, 50 µL of a 40 mg/mL H308 solution was intravitreally administered to one eye under anesthesia. Normal saline was intravitreally administered to the fellow eye. n=5 for all groups.

After 4 months from the start of feeding, RPE cell hypertrophy in the model animals was evaluated. The results are shown in FIG. 72. The HTRA1 inhibitor exhibited a suppressive effect on the hypertrophy of RPE cells, as seen from both the indicators, i.e., the average area of RPE cells (FIG. 72(A)) and the number of hypertrophied RPE cells having a cell area of 1500 µm$^2$ or larger (FIG. 72(B)). As shown in FIG. 71(E), an increase in HTRA1 was confirmed in the vitreous humor of the models, suggesting the involvement of HTRA1 in the process of damage on RPE cells due to HFD-HQ. Thus, the HTRA1-inhibiting peptide is useful as an anti-age-related macular degeneration agent. This test indicated that the HTRA1-inhibiting peptide is useful in the prevention of dry age-related macular degeneration, in particular.

The presence of the HTRA1-inhibiting peptide was confirmed in the retina of a normal rabbit given the HTRA1-inhibiting peptide, indicating the high tissue penetration of the HTRA1-inhibiting peptide.

Example 12. Suppressive Effect of HTRA1-Inhibiting Peptide in VEGF mRNA Induction Test Using Human Retinal Pigment Epithelial Cells ARPE-19

ARPE-19 cells were cultured until confluent in 12 mm Transwell with 0.4 m Pore Polyester Membrane Insert, Sterile (Corning Inc.) under conditions of 37° C. and 5% $CO_2$ using a DMEM/F-12 medium (Wako Pure Chemical Industries, Ltd.) containing 10% fetal bovine serum (FBS) and penicillin-streptomycin (Thermo Fisher Scientific Inc.). Then, the cells were cultured in FBS-free DMEM/F-12 for 5 days. $H_2O_2$ (final concentration: 500 µM) was added to the upper and lower layers of the chamber, and normal human serum complement (Quidel Corp.) (final concentration: 25%) was added to the upper layer of the chamber. Each of HTRA1 (Example 2-2), inactive HTRA1 protease mutant HTRA1 (S328A) (Example 2-3), or HTRA1-inhibiting peptide H308_D1G_S16A (Example 6) was further added at a final concentration of 1 µM to the upper and lower layers of the chamber. Four hours later, the culture supernatant was removed, and the cells were washed with PBS. Then, mRNA was extracted using SuperPrep™ Cell Lysis & RT Kit for qPCR (Toyobo Co., Ltd.) and subjected to a reverse transcription reaction. The mRNA level of VEGF was quantitatively analyzed by TaqMan Gene Expression Assays (Hs000900055_m1 and Hs02786624_g1; Thermo Fisher Scientific Inc.) using a 7900HT Fast Real-Time PCR System (Applied Biosystems, Inc.). GAPDH was used in the correction of the mRNA level.

Figure 74:
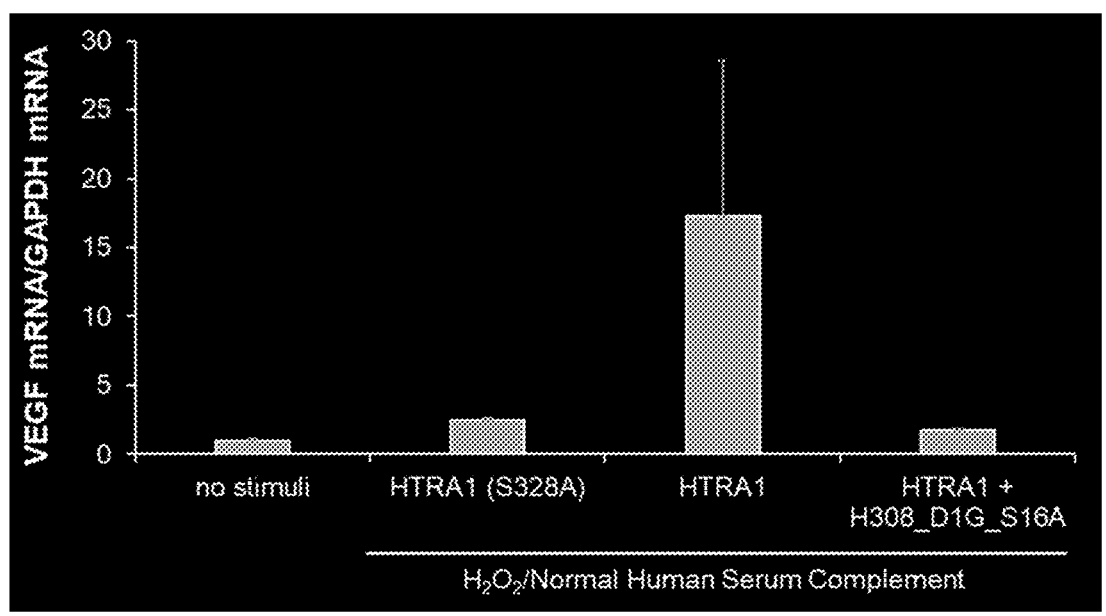
FIG. 74 is a diagram showing that a HTRA1-inhibiting peptide exhibited a suppressive effect on VEGF mRNA induced in a human retinal pigment epithelial cell line ARPE-19 by the addition of $H_2O_2$, normal human serum complement, and HTRA1.

The results are shown in FIG. 74. The addition of $H_2O_2$, normal human serum complement and HTRA1 markedly increased the mRNA level of VEGF as compared with the conditions involving adding $H_2O_2$, normal human serum complement and inactive HTRA1 mutant HTRA1 (S328A). The co-addition of the HTRA1-inhibiting peptide H308_D1G_S16A was confirmed to suppress the expression of VEGF. VEGF induction from retinal pigment epithelial cells was reportedly important for the pathogenesis of wet age-related macular degeneration (Klettner A. et al., (2009) Graefes Arch Clin Exp Ophthalmol., Vol. 247: p. 1487-1492). In addition, it is considered that such morbid VEGF induction is involved not only in the pathogenesis but in the maintenance of the pathological condition. Thus, the administration of a peptide of the present invention, such as HTRA1-inhibiting peptide H308_D1G_S16A, is effective for the prevention and treatment of wet age-related macular degeneration.

Example 13. Suppressive Effect of HTRA1-Inhibiting Peptide H308_D1G_S16A on Human Umbilical Vein Endothelial Cell (HUVEC) Migration (13-1) HUVEC Migration Test HUVEC (Kurabo Industries Ltd.) was cultured for 18 hours under conditions of 37° C. and 5% $CO_2$ in a medium (0.1% BSA-containing serum-free EGM) in which EBM™-2 basal medium (Lonza Walkersville, Inc.) containing 0.1% BSA was supplemented with an EGM™-2 SingleQuots™ additive factor set except for serum and VEGF. Then, the cells were adjusted to $4\times10^5$ cells/mL with 0.1% BSA-containing serum-free EGM. $4\times10^5$ cells/mL of the HUVEC suspension was added at 50 µL/well to the upper layer of a chamber of a Corning FluoroBlok HTS 96 Well Multiwell Permeable Support System with a 3.0 m High Density PET Membrane (Corning Inc.) having a gelatin-coated membrane. Then, each sample described below (medium 1, 2 or 3) was added at 210 µL/well to the lower layer of the chamber (n=3). 0.1% BSA-containing serum-free EGM was added at 50 L/well to the upper layer of a chamber without the addition of HUVEC, and 0.1% BSA-containing serum-free EGM was added at 210 µL/well to the lower layer of the chamber (n=3).

Medium 1; 0.1% BSA-containing serum-free EGM
Medium 2; EBM™-2 medium supplemented with all EGM™—2 SingleQuots™ additive factors (EGM growth medium) Medium 3; EGM growth medium containing 300 nM H308_D1G_S16A A FluoroBlok HTS 96 Well Multiwell Support System supplemented with the cells and the sample was incubated for 2 hours under conditions of 37° C. and 5% $CO_2$. HUVEC migrated to the lower layer was washed with PBS and then stained for 15 minutes with 0.1% BSA-containing serum-free EGM containing 4 µg/mL Calcein-AM (Thermo Fisher Scientific Inc.). Then, the medium was replaced with PBS. The fluorescence intensity (excitation wavelength/fluorescence wavelength: 485 nm/535 nm) of each well was measured using a plate reader (ARVO-MX, PerkinElmer, Inc.), and the migrated cells were counted for each well according to the following expression. Migrated cells=Mean fluorescence intensity of wells containing HUVEC (n=3)—Mean fluorescence intensity of blank wells (n=3).

Figure 75:
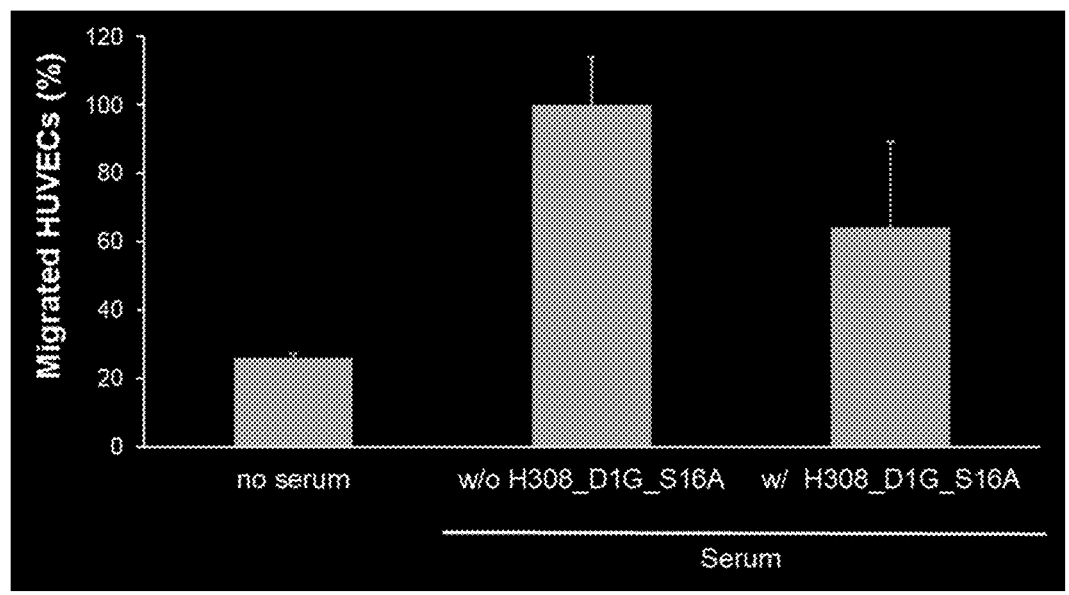
FIG. 75 is a diagram showing that a HTRA1-inhibiting peptide exhibited a suppressive effect on the migration of human umbilical vein endothelial cells (HUVEC) induced by serum.

The results are shown in FIG. 75. The HTRA1-inhibiting peptide H308_D1G_S16A was confirmed to have a suppressive effect on the migration of HUVEC induced in the serum-containing medium. Accordingly, the peptide of the present invention was found to exhibit a suppressive effect on angiogenesis, a feature of wet age-related macular degeneration.

Example 14. Retinal Protective Effect of HTRA1-Inhibiting Peptide in Rabbit Retinal Damage Model (Part 2)

HTRA1-inhibiting peptide H308 prepared in Example 1 or one of the three HTRA1-inhibiting peptides prepared in Example 6 is evaluated for its therapeutic effect on retinal damage using the rabbit retinal damage models prepared and evaluated in Examples (11-1) to (11-3). 50 µL of a 40 mg/mL inhibiting peptide solution is intravitreally administered to one eye of each model animal under anesthesia, and the animal is raised for 2 months. Normal saline is intravitreally administered to the fellow eye. n=5 for all groups.

Increase in RPE cell area or increase in RPE cell count should be found in the normal saline administration group, whereas the increase in RPE cell area or the increase in RPE cell count should be suppressed in the HTRA1-inhibiting peptide administration group. Thus, the HTRA1-inhibiting peptide can be confirmed to be useful as an anti-age-related macular degeneration agent. In this Example, the HTRA1-inhibiting peptide can be confirmed to be useful in the treatment of dry age-related macular degeneration, in particular.

Example 15. Study on Photoreceptor Cell Protective Effect of HTRA1-Inhibiting Peptide in Rd10 Retinitis Pigmentosa Model Mice (15-1) Rearing of Rd10 Mice The B6. CXB1-Pde6brd10/J (hereinafter Rd10) mouse has a mutation in the Pde6b gene, and is a model that spontaneously induces photoreceptor cell death. It is widely used as a model animal for retinitis pigmentosa (Chang B1, Hawes N L, Hurd R E, Davisson M T, Nusinowitz S, and Heckenlivery J R., Vision Res., February 2002, 42 (No. 4): p. 517-25). The mice were reared under normal rearing conditions.

(15-2) Administration of Test Substance to Mouse Vitreous Body at Both Postnatal Day 14 and 19

At P14 and 19, 0.5 µL of the liquid medicine was intravitreally administered using a 33G needle under ketamine anesthesia. PBS was administered to one eye, and the HTRA1-inhibiting peptide (H308_D1G_S16A: SEQ ID NO: 24, FIG. 36) was administered to the other eye.

(15-3) Evaluation and Analysis of Photoreceptor Cell Death

After euthanasia, the eyeballs were excised and fixed by dipping them in a 3.7% (W/V) formaldehyde-0.5 to 1% (W/V) methanol-0.2% (W/V) picric acid fixative for 24 hours or longer. After paraffin embedding, thin sliced sections were prepared. The photoreceptor cell protective effect was evaluated by staining the sections with hematoxylin-eosin, and by correcting the thickness of the outer nuclear layer (ONL layer) of the retinal slice with the thickness of the inner nuclear layer (INL layer). Two points, each 0.6 mm from and on either side of the papilla were measured as the central parts, and two points, each 1.8 mm from and on either side of the papilla were measured as the peripheral parts, then the average of the two central parts and the average value of the two peripheral parts were calculated. Student's paired-t test method was used for the statistical analysis.

(15-4) Results

Figure 78:
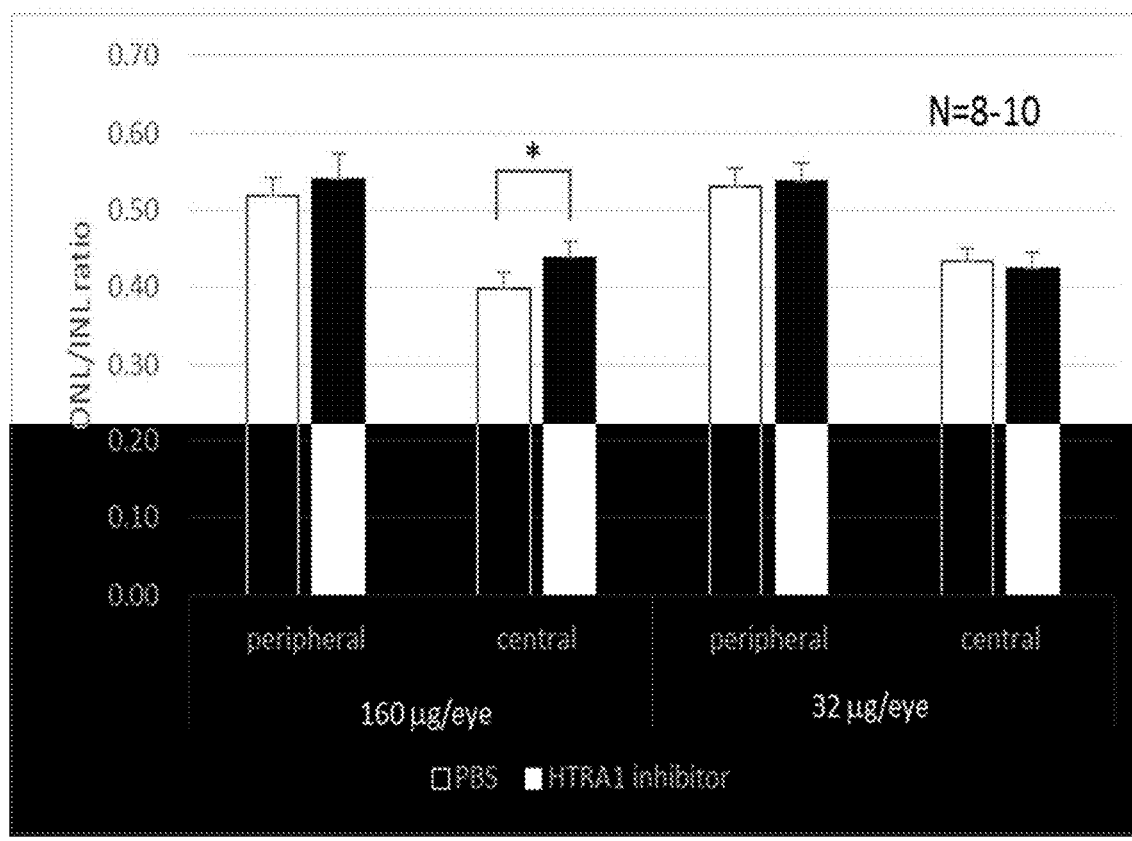
FIG. 78 is a diagram showing that the ONL/INL ratio was significantly increased in the central parts of the 160 μg/eye administration group as compared to in the control PBS group, and that the ONL/INL ratio also tended to increase in the peripheral parts as compared to in the control group when the HTRA1-inhibiting peptide was administered to Rd10 mice (B6·CXB1-Pde6b$^{rd10}$a/J). * indicates p<0.05 in Student's paired-t test. See Example 15.

The thickness of the outer nuclear layer (where the nuclei of photoreceptor cells are accumulated) of the eyes to which 160 µg/eye of the HTRA1-inhibiting peptide was administered was statistically significantly improved in the central parts as compared with the eyes to which PBS was administered. A similar medicinal effect was not observed in the eyes to which 32 µg/eye was administered, confirming dose-dependence (FIG. 78).

Example 16. Analysis of HTRA1 Expression in Mutant Rhodopsin Gene [P347L]-Introduced Rabbit (16-1) Analysis of HTRA1 mRNA Expression in Rabbit Retina RNA was extracted from the retinas of male 15-week-old wild-type (WT) and mutant rhodopsin gene [P347L]-introduced (Tg) rabbits using RNeasy Mini Kit (QIAGEN), and a High-Capacity cDNA Reverse Transcription Kit (Thermo Fisher) was used to reverse-transcribe it into cDNA. Then, the mRNA expression of HTRA1 was analyzed using a TaqMan probe (Thermo Fisher) and TaqMan Gene Expression Assays (Thermo Fisher).

(16-2) Site-Specific Analysis of HTRA1 mRNA Expression Using Laser Microdissection Retinas of male 24-week-old WT and Tg rabbits were fixed using 10% neutral buffered formalin. Paraffin-embedded specimens were prepared, then cut into thin slices and stained with Nissl. The ganglion cell layer, inner nuclear layer, and outer nuclear layer were excised from the stained sections using LMD6500 (Leica), and RNA was extracted using a QIAGEN RNeasy FFPE Mini Kit (QIAGEN). Then, a library was created for each using SMARTer Stranded Total RNA-Seq Kit-Pico Input Mammalian (Clontech). The sequences of the libraries were comprehensively analyzed using Nextseq (Illumina). It was confirmed that there was no problem with the excisions by analyzing the marker genes specifically expressed in each layer. The copy number of HTRA1 mRNA was calculated as a TPM (Transcript Per Million) value.

(16-3) Results (16-3-1)

At the age of 15 weeks, the retinas of the Tg rabbits expressed about 1.5 times more HTRA1 mRNA than the wild-type rabbits. In addition, photoreceptor cell degeneration occurred in the outer nuclear layer (the number of Tg rabbits was 5, and the number of wild-type rabbits was 4).

(16-3-2)

When site-specific analysis in wild-type rabbits and Tg rabbits was performed by the laser microdissection method at 24 weeks of age, (a) the TPM values in the ganglion cell layer were 11.76±1.47 and 9.99±3.94 respectively, (b) TPM values in the inner nuclear layer were 75.79±22.02 and 54.55±13.12 respectively, and (c) the TPM values in the outer nuclear layer were 6.21±3.33 and 25.37±6.45 respectively (there was a statistically significant difference between both values) (the number of cases was 3 to 6).

(16-3-3)

P347L transgenic rabbits carry the same rhodopsin gene mutation as human retinitis pigmentosa patients. Photoreceptor cell death is induced in the same manner as in human retinitis pigmentosa patients, and photoreceptor cell degeneration is observed at 15 to 24 weeks of age, which were the conditions used here (Kondo M1, Sakai T, Komeima K, Kurimoto Y, Ueno S, Nishizawa Y, Usukura J, Fujikado T, Tano Y, and Terasaki H., Invest Ophthalmol Vis Sci., May 2009, Vol. 50 (No. 3): p. 1371-7).

The outer nuclear layer is a site where the nuclei of photoreceptor cells are accumulated, and a correlation was observed between photoreceptor cell degeneration and increased HTRA1 gene expression, which, if taking the other disclosures of the present invention also into account, suggests that it will be a useful therapeutic drug for retinitis pigmentosa with a rhodopsin gene mutation, such as P347L.

Industrial Applicability

The peptide or a conjugate thereof provided by the present invention, and a pharmaceutical composition comprising the peptide or a conjugate thereof are useful in the treatment or prevention, etc. of retinitis pigmentosa, etc.

SEQUENCE LISTING FREE TEXT

SEQ ID NO: 1—Amino acid sequence of human SPINK2 (FIG. 13)
SEQ ID NO: 2—Nucleotide sequence encoding amino acid sequence of human SPINK2 (FIG. 14)
SEQ ID NO: 3—Amino acid sequence of peptide H218 (FIG. 15)
SEQ ID NO: 4—Nucleotide sequence encoding amino acid sequence of peptide H218 (FIG. 16)
SEQ ID NO: 5—Amino acid sequence of peptide H223 (FIG. 17)
SEQ ID NO: 6—Nucleotide sequence encoding amino acid sequence of peptide H223 (FIG. 18)
SEQ ID NO: 7—Amino acid sequence of peptide H228 (FIG. 19)
SEQ ID NO: 8—Nucleotide sequence encoding amino acid sequence of peptide H228 (FIG. 20)
SEQ ID NO: 9—Amino acid sequence of peptide H308 (FIG. 21)
SEQ ID NO: 10—Nucleotide sequence encoding amino acid sequence of peptide H308 (FIG. 22)
SEQ ID NO: 11—Amino acid sequence of peptide H321 (FIG. 23)
SEQ ID NO: 12—Nucleotide sequence encoding amino acid sequence of peptide H321 (FIG. 24)
SEQ ID NO: 13—Amino acid sequence of peptide H322 (FIG. 25)
SEQ ID NO: 14—Nucleotide sequence encoding amino acid sequence of peptide H322 (FIG. 26)
SEQ ID NO: 15—Amino acid sequence of peptide derivative H308AT (FIG. 27)
SEQ ID NO: 16—Nucleotide sequence encoding amino acid sequence of peptide derivative H308AT (FIG. 28)
SEQ ID NO: 17—Amino acid sequence of peptide derivative H321AT (FIG. 29)
SEQ ID NO: 18—Nucleotide sequence encoding amino acid sequence of peptide derivative H321AT (FIG. 30)
SEQ ID NO: 19—Amino acid sequence of peptide derivative H322AT (FIG. 31)
SEQ ID NO: 20—Nucleotide sequence encoding amino acid sequence of peptide derivative H322AT (FIG. 32)
SEQ ID NO: 21—Amino acid sequence of peptide M7 (FIG. 33)
SEQ ID NO: 22—Nucleotide sequence encoding amino acid sequence of peptide M7 (FIG. 34)
SEQ ID NO: 23—Amino acid sequence of peptide derivative H308_S16A (FIG. 35)
SEQ ID NO: 24—Amino acid sequence of peptide derivative H308_D1G_S16A (FIG. 36)
SEQ ID NO: 25—Amino acid sequence of peptide derivative H308_D1S_S16A (FIG. 37)
SEQ ID NO: 26—Amino acid sequence of peptide derivative H308_D1E_S16A (FIG. 38)
SEQ ID NO: 27—Amino acid sequence of peptide derivative H308_D1SLI_S16A (FIG. 39)
SEQ ID NO: 28—Amino acid sequence of peptide derivative H321AT_D1G_S16A (FIG. 40)
SEQ ID NO: 29—Amino acid sequence of peptide derivative H322AT_D1G_S16A (FIG. 41)
SEQ ID NO: 30—General formula of HTRA1-inhibiting peptide (FIG. 42)
SEQ ID NO: 31—Amino acid sequence consisting of S tag and linker (FIG. 43)

SEQ ID NO: 32—Amino acid sequence of C-terminal hexamer (FIG. 44)
SEQ ID NO: 33—Nucleotide sequence of primer 1 (FIG. 45)
SEQ ID NO: 34—Nucleotide sequence of primer 2 (FIG. 46)
SEQ ID NO: 35—Nucleotide sequence of primer 3 (FIG. 47)
SEQ ID NO: 36—Nucleotide sequence of primer 4 (FIG. 48)
SEQ ID NO: 37—Nucleotide sequence of primer 5 (FIG. 49)
SEQ ID NO: 38—Nucleotide sequence of primer 6 (FIG. 50)
SEQ ID NO: 39—Nucleotide sequence of primer 7 (FIG. 51)
SEQ ID NO: 40—Nucleotide sequence of primer 8 (FIG. 52)
SEQ ID NO: 41—Nucleotide sequence of primer 9 (FIG. 53)
SEQ ID NO: 42—Nucleotide sequence of primer 10 (FIG. 54)
SEQ ID NO: 43—Nucleotide sequence of primer 11 (FIG. 55)
SEQ ID NO: 44—Nucleotide sequence of primer 12 (FIG. 56)
SEQ ID NO: 45—Nucleotide sequence of primer 13 (FIG. 57)
SEQ ID NO: 46—Nucleotide sequence of primer 14 (FIG. 58)
SEQ ID NO: 47—Nucleotide sequence of primer 15 (FIG. 59)
SEQ ID NO: 48—Nucleotide sequence of primer 16 (FIG. 60)
SEQ ID NO: 49—Nucleotide sequence of primer 17 (FIG. 61)
SEQ ID NO: 50—Nucleotide sequence of primer 18 (FIG. 62)
SEQ ID NO: 51—Nucleotide sequence of primer 19 (FIG. 63)
SEQ ID NO: 52—Nucleotide sequence of primer 20 (FIG. 64)
SEQ ID NO: 53—Amino acid sequence of human HTRA1 (full) (FIG. 65)
SEQ ID NO: 54—Amino acid sequence of H2-Opt (FIG. 8)
SEQ ID NO: 55—Nucleotide sequence of primer 21 (FIG. 76)
SEQ ID NO: 56—Nucleotide sequence of primer 22 (FIG. 77)

The invention claimed is:

1. A method for the treatment of retinitis pigmentosa, hereditary diseases involving photoreceptor cell degeneration, and/or diseases associated with PDE6 protein dysfunction, comprising administering to a subject in need thereof a therapeutically effective amount of a SPINK2 mutant peptide which comprises the amino acid sequence shown in SEQ ID NO: 30 and which inhibits the protease activity of human HTRA1.

2. The method according to claim 1, wherein the first Xaa ($X_1$) is Asp, Glu, Ser, Gly, or Ile, the second Xaa ($X_2$) is Ala, Gly, Leu, Ser or Thr, the third Xaa ($X_3$) is Asp, His, Lys, Met or Gln, the fourth Xaa ($X_4$) is Asp, Phe, His, Ser or Tyr, the fifth Xaa ($X_5$) is Ala, Asp, Glu, Met or Asn, the sixth Xaa ($X_6$) is Met or Trp, the seventh Xaa ($X_7$) is Gln, Trp, Tyr or Val, the eighth Xaa ($X_8$) is Phe, Leu or Tyr, the ninth Xaa ($X_9$) is Phe or Tyr, the tenth Xaa ($X_{10}$) is Ala, Glu, Met or Val, and the eleventh Xaa ($X_{11}$) is Ala, Thr or Val in the amino acid sequence shown in SEQ ID NO: 30 comprised in the peptide.

3. The according to claim 1, wherein the peptide comprises an amino acid sequence shown in any one of SEQ ID NOs: 3, 5, 7, 9, 11, 13, 15, 17, 19, 21 and 23 to 29.

4. The method according to claim 1, wherein the peptide comprises an amino acid sequence prepared by the addition via a peptide bond of one to three amino acids at the amino-terminal side of the amino acid sequence shown in SEQ ID NO: 30.

5. The method according to claim 1, wherein the peptide comprises an amino acid sequence prepared by the addition via a peptide bond of one or two amino acids at the carboxyl-terminal side of the amino acid sequence shown in SEQ ID NO: 30.

6. The method according to claim 1, wherein the peptide has a three-dimensional structure characterized by having three disulfide bonds and comprising a loop structure, an α helix and a β sheet.

7. A method for the treatment of retinitis pigmentosa, hereditary diseases involving photoreceptor cell degeneration, and/or diseases associated with PDE6 protein dysfunction, comprising administering to a subject in need thereof a therapeutically effective amount of a polynucleotide comprising a nucleotide sequence encoding an amino acid sequence comprised in the peptide according to claim 1.

8. A method for the treatment of retinitis pigmentosa, hereditary diseases involving photoreceptor cell degeneration, and/or diseases associated with PDE6 protein dysfunction, comprising administering to a subject in need thereof a therapeutically effective amount of a vector comprising a nucleotide sequence encoding an amino acid sequence comprised in the peptide according to claim 1.

9. A method for the treatment of retinitis pigmentosa, hereditary diseases involving photoreceptor cell degeneration, and/or diseases associated with PDE6 protein dysfunction, comprising a cell producing the peptide according to claim 1.

10. The method according to claim 7, wherein administering the SPINK2 mutant peptide comprises administering a conjugate comprising the SPINK2 mutant peptide linked to an additional moiety.

11. The method according to claim 10, wherein the conjugate is a polypeptide.

12. The method according to claim 7 for the treatment of retinitis pigmentosa.

13. The method according to claim 7 for the treatment of hereditary diseases involving photoreceptor cell degeneration.

14. The method according to claim 13, wherein the hereditary disease involving photoreceptor cell degeneration is macular dystrophy.

15. The method according to claim 7 for the treatment of diseases associated with PDE6 protein dysfunction.

16. The method according to claim 15, wherein the disease associated with PDE6 protein dysfunction is achromatopsia or autosomal dominant congenital stationary night blindness.

17. The method according claim 1, comprising administering to the subject one or two or more additional medicaments.

18. A method for identifying a therapeutic drug or a prophylactic drug for retinitis pigmentosa, hereditary diseases involving photoreceptor cell degeneration, and/or diseases associated with PDE6 protein dysfunction, comprising the following steps 1 to 3:

[step 1] incubating a HTRA1 protease and a substrate in the presence and absence of a test substance, which is a SPINK2 mutant peptide comprising the amino acid sequence shown in SEQ ID NO: 30;

[step 2] detecting HTRA1 protease activity in the presence and absence of the test substance; and

[step 3] determining the test substance to be positive when the HTRA1 protease activity in the presence of the test substance is lower than the HTRA1 protease activity in the absence of the test substance.

19. The method according to claim 8 for the treatment of retinitis pigmentosa.

20. The method according to claim 8 for the treatment of hereditary diseases involving photoreceptor cell degeneration.

21. The method according to claim 1, wherein the hereditary disease involving photoreceptor cell degeneration is macular dystrophy.

22. The method according to claim 8 for the treatment of diseases associated with PDE6 protein dysfunction.

23. The method according to claim 22, wherein the disease associated with PDE6 protein dysfunction is achromatopsia or autosomal dominant congenital stationary night blindness.

24. The method according to claim 8, comprising administering to the subject one or two or more additional medicaments.

25. A method for the treatment of retinitis pigmentosa, hereditary diseases involving photoreceptor cell degeneration, and/or diseases associated with PDE6 protein dysfunction, comprising administering to a subject in need thereof a therapeutically effective amount of a polynucleotide comprising a nucleotide sequence encoding an amino acid sequence comprised in the peptide according to claim 3.

26. The method according to claim 25 for the treatment of retinitis pigmentosa.

27. The method according to claim 25 for the treatment of hereditary diseases involving photoreceptor cell degeneration.

28. The method according to claim 27, wherein the hereditary disease involving photoreceptor cell degeneration is macular dystrophy.

29. The method according to claim 25 for the treatment of diseases associated with PDE6 protein dysfunction.

30. The method according to claim 29, wherein the disease associated with PDE6 protein dysfunction is achromatopsia or autosomal dominant congenital stationary night blindness.

31. The method according to claim 25, comprising administering to the subject one or two or more additional medicaments.

32. A method for the treatment of retinitis pigmentosa, hereditary diseases involving photoreceptor cell degeneration, and/or diseases associated with PDE6 protein dysfunction, comprising administering to a subject in need thereof a therapeutically effective amount of a vector comprising a nucleotide sequence encoding an amino acid sequence comprised in the peptide according to claim 3.

33. The method according to claim 32 for the treatment of retinitis pigmentosa.

34. The method according to claim 32 for the treatment of hereditary diseases involving photoreceptor cell degeneration.

35. The method according to claim 34, wherein the hereditary disease involving photoreceptor cell degeneration is macular dystrophy.

36. The method according to claim 32 for the treatment of diseases associated with PDE6 protein dysfunction.

37. The method according to claim 36, wherein the disease associated with PDE6 protein dysfunction is achromatopsia or autosomal dominant congenital stationary night blindness.

38. The method according to claim 32, comprising administering to the subject one or two or more additional medicaments.

39. A method for the treatment of retinitis pigmentosa, hereditary diseases involving photoreceptor cell degeneration, and/or diseases associated with PDE6 protein dysfunction, comprising administering to a subject in need thereof a therapeutically effective amount of a cell producing the peptide according to claim 3.

40. The method according to claim 39 for the treatment of retinitis pigmentosa.

41. The method according to claim 39 for the treatment of hereditary diseases involving photoreceptor cell degeneration.

42. The method according to claim 41, wherein the hereditary disease involving photoreceptor cell degeneration is macular dystrophy.

43. The method according to claim 39 for the treatment of diseases associated with PDE6 protein dysfunction.

44. The method according to claim 43, wherein the disease associated with PDE6 protein dysfunction is achromatopsia or autosomal dominant congenital stationary night blindness.

45. The method according to claim 39, comprising administering to the subject one or two or more additional medicaments.

\* \* \* \* \*